US011834783B2

(12) United States Patent
Rowlands et al.

(10) Patent No.: US 11,834,783 B2
(45) Date of Patent: *Dec. 5, 2023

(54) INTEGRATED KRAFT PULP MILL AND THERMOCHEMICAL CONVERSION SYSTEM

(71) Applicants: Canfor Pulp Ltd., Burnaby (CA); Licella Pty Ltd., North Sydney (AU)

(72) Inventors: William Neil Rowlands, Alexandria (AU); Leonard James Humphreys, Roseville Chase (AU); Robert William Clayton Thew, Prince George (CA); James Allan Spankie, Prince George (CA); Victor Charles Uloth, Prince George (CA); Paul Andrew Watson, Cook Beach (NZ); Martin William Pudlas, Prince George (CA)

(73) Assignees: CANFOR PULP LTD., Burnaby (CA); LICELLA PTY LTD., North Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/710,543

(22) Filed: Mar. 31, 2022

(65) Prior Publication Data

US 2022/0396917 A1    Dec. 15, 2022

Related U.S. Application Data

(63) Continuation of application No. 15/519,171, filed as application No. PCT/CA2015/051037 on Oct. 14, 2015, now Pat. No. 11,306,435.

(Continued)

(30) Foreign Application Priority Data

Oct. 15, 2014  (AU) ................... 2014904129

(51) Int. Cl.
*D21C 11/00*    (2006.01)
*C10L 5/44*    (2006.01)
(Continued)

(52) U.S. Cl.
CPC .......... *D21C 11/0007* (2013.01); *C07C 29/88* (2013.01); *C07C 41/44* (2013.01);
(Continued)

(58) Field of Classification Search
CPC ..... D21C 11/0007; C07C 29/88; C07C 41/44; C07C 45/85; C10L 3/00; C10L 5/442;
(Continued)

(56) References Cited

U.S. PATENT DOCUMENTS 3,607,619 A * 9/1971 Hess ....................... C02F 11/10
                                                    162/34
4,347,220 A   8/1982 Nelson et al.
(Continued)

FOREIGN PATENT DOCUMENTS

CN    102352572 A    2/2012
EP    2449057 A1    5/2012
(Continued)

OTHER PUBLICATIONS

Apr. 30, 2020 Amendment in response dated Dec. 30, 2019 Office Action issued in connection with U.S. Appl. No. 15/519,171.
(Continued)

*Primary Examiner* — Ellen M McAvoy
*Assistant Examiner* — Ming Cheung Po
(74) *Attorney, Agent, or Firm* — Gary J. Gershik

(57) ABSTRACT

This disclosure pertains to the use of black liquors from kraft pulp mills as a source of catalysts for the thermochemical conversion of organic matter feedstocks to bio oils. More particularly, some embodiments pertain to integrated kraft pulp mill and thermochemical conversion systems, which
(Continued)

include: a Kraft pulp mill comprising a digester for digesting a lignocellulosic material with white liquor to produce pulp and black liquors; a thermochemical conversion subsystem comprising: at least one mixing tank for combining pulping liquors received from the pulp mill with an organic matter feedstock and water to produce a reaction mixture; a reactor vessel for treating the reaction mixture received from the mixing tank at a reaction temperature and pressure suitable for conversion of all or a portion of the organic matter in the reaction mixture into a product mixture comprising a bio-product and an aqueous stream containing both organic and inorganic compounds; and a depressurizer for depressurizing product mixture received from the reactor vessel; and one or more conveyors for conveying the pulping liquors from the pulp mill to the mixing tank.

20 Claims, 3 Drawing Sheets

Related U.S. Application Data

(60) Provisional application No. 62/156,737, filed on May 4, 2015.

(51) Int. Cl.
| | |
|---|---|
| *C10L 5/48* | (2006.01) |
| *D21C 3/02* | (2006.01) |
| *D21C 3/20* | (2006.01) |
| *C12P 7/08* | (2006.01) |
| *C10G 3/00* | (2006.01) |
| *C10G 1/08* | (2006.01) |
| *C10G 1/10* | (2006.01) |
| *C10L 1/02* | (2006.01) |
| *C10G 1/00* | (2006.01) |
| *C10G 1/04* | (2006.01) |
| *C10L 3/00* | (2006.01) |
| *C07C 29/88* | (2006.01) |
| *C07C 41/44* | (2006.01) |
| *C07C 45/85* | (2006.01) |

(52) U.S. Cl.
CPC ............... *C07C 45/85* (2013.01); *C10G 1/00* (2013.01); *C10G 1/04* (2013.01); *C10G 1/086* (2013.01); *C10G 1/10* (2013.01); *C10G 3/00* (2013.01); *C10L 1/02* (2013.01); *C10L 3/00* (2013.01); *C10L 5/442* (2013.01); *C10L 5/48* (2013.01); *C12P 7/08* (2013.01); *D21C 3/02* (2013.01); *D21C 3/20* (2013.01); *C10G 2300/1003* (2013.01); *C10G 2300/1014* (2013.01); *C10L 2200/0469* (2013.01); *C10L 2290/06* (2013.01); *C10L 2290/24* (2013.01); *C10L 2290/544* (2013.01); *C10L 2290/547* (2013.01); *Y02E 50/10* (2013.01); *Y02E 50/30* (2013.01); *Y02P 20/582* (2015.11); *Y02P 30/20* (2015.11)

(58) Field of Classification Search
CPC ......... C10L 2200/0469; C10L 2290/24; C10L 5/48; C10L 220/0469
See application file for complete search history.

(56) References Cited

U.S. PATENT DOCUMENTS

| | | | |
|---|---|---|---|
| 4,381,035 | A | 4/1983 | Hradel |
| 4,692,209 | A | 9/1987 | Santen et al. |
| 5,019,135 | A | 5/1991 | Sealock, Jr. et al. |
| 6,306,248 | B1 | 10/2001 | Eley |
| 7,262,331 | B2 | 8/2007 | van de Beld et al. |
| 8,003,833 | B2 | 8/2011 | Appel et al. |
| 2004/0079498 | A1 | 4/2004 | Haaslahti et al. |
| 2006/0096163 | A1 | 5/2006 | Dickinson et al. |
| 2011/0232162 | A1 | 9/2011 | Siskin et al. |
| 2011/0275869 | A1 | 11/2011 | Prochazka et al. |
| 2012/0152836 | A1 | 6/2012 | Powell et al. |
| 2017/0226695 | A1 | 8/2017 | Rowlands et al. |

FOREIGN PATENT DOCUMENTS

| | | | | |
|---|---|---|---|---|
| JP | S59199892 | A | 11/1984 | |
| JP | 2006-076979 | A | 3/2006 | |
| JP | 2007-038144 | A | 2/2007 | |
| WO | WO 99/07936 | | 2/1999 | |
| WO | WO 00/52256 | | 9/2000 | |
| WO | WO 02/20699 | | 2/2002 | |
| WO | WO 2004/087619 | | 10/2004 | |
| WO | WO 2006/053020 | | 5/2006 | |
| WO | WO 2009/028969 | | 3/2009 | |
| WO | WO 2010/037178 | | 4/2010 | |
| WO | WO 2011/138633 | | 11/2011 | |
| WO | WO 2012/000033 | | 1/2012 | |
| WO | WO 2012/047832 | | 4/2012 | |
| WO | WO/2012/175796 | | 12/2012 | |
| WO | WO-2012167794 | A2 * | 12/2012 | ............... C10G 1/00 |
| WO | WO-2012175796 | A1 * | 12/2012 | ............... C10G 1/02 |
| WO | WO 2016/058031 | | 4/2016 | |

OTHER PUBLICATIONS

Aug. 30, 2021 Notice of Allowance issued in connection with U.S. Appl. No. 15/519,171.
Dec. 11, 2020 Office Action issued in connection with U.S. Appl. No. 15/519,171.
Dec. 23, 2021 Notice of Allowance issued in connection with U.S. Appl. No. 15/519,171.
Dec. 30, 2019 Office Action issued in connection with U.S. Appl. No. 15/519,171.
Feb. 14, 2019 Amendment in response dated Oct. 18, 2018 Office Action issued in connection with U.S. Appl. No. 15/519,171.
Jul. 16, 2018 Communication in response to May 16, 2018 Office Action issued in connection with U.S. Appl. No. 15/519,171.
May 16, 2018 Office Action issued in connection with U.S. Appl. No. 15/519,171.
May 30, 2019 Office Action issued in connection with U.S. Appl. No. 15/519,171.
Nov. 11, 2020 Amendment in response dated Sep. 11, 2020 Office Action issued in connection with U.S. Appl. No. 15/519,171.
Nov. 26, 2019 Amendment in response dated May 30, 2019 Office Action issued in connection with U.S. Appl. No. 15/519,171.
Oct. 18, 2018 Office Action issued in connection with U.S. Appl. No. 15/519,171.
Sep. 11, 2020 Office Action issued in connection with U.S. Appl. No. 15/519,171.
International Search Report and the Written Opinion issued by the International Searching Authority (ISA/O.E.P.M.) dated Dec. 4, 2015 in connection with International Application No. PCT/CA2015/051037.

* cited by examiner

INTEGRATED KRAFT PULP MILL AND THERMOCHEMICAL CONVERSION SYSTEM

CROSS-REFERENCE TO RELATED APPLICATIONS

This application is a continuation of U.S. application Ser. No. 15/519,171, filed Apr. 14, 2017, now allowed, a § 371 national stage of PCT International Application No. PCT/CA2015/051037, filed Oct. 14, 2015, claiming priority of Australian Provisional Application No. 2014904129, filed Oct. 15, 2014, and claiming the benefit of U.S. Provisional Application No. 62/156,737, filed May 4, 2015, the contents of each of which are hereby incorporated by reference into the subject application.

This application claims priority to Australian Provisional Application No. 2014904129 filed Oct. 15, 2014, and to U.S. Provisional Application No. 62/156,737 filed May 4, 2015. Each of the aforementioned applications is incorporated herein in its entirety by reference.

BACKGROUND OF THE INVENTION

1. Field of Invention

The present disclosure relates generally to the generation of bio-products from organic matter feedstocks. More specifically, the present disclosure pertains to the use of pulping liquors in the hydrothermal/thermochemical conversion of lignocellulosic and/or fossilized organic feedstocks into biofuels (e.g. bio-oils) and/or chemical products (e.g. platform chemicals). This disclosure further pertains to methods and systems for the integration of a kraft pulp mill with a thermochemical conversion plant.

2. Description of Related Art

Kraft pulp mills convert wood chips to cellulose rich pulp fibres by selectively dissolving the wood extractives (resins and fatty acids), hemicelluloses and the lignin fractions of the woody matrix. In the process, several streams of organic waste are generated. The dissolved wood extractives, cellulose fragments and derived sugars, hemicelluloses and the lignin fractions organics are collectively referred to as black liquor. Black liquor is typically concentrated from 15% to about 70% solids by weight and then incinerated in a recovery furnace to recover heat and the inorganic cooking chemicals. Kraft pulp mills also produce primary sludge which is comprised largely of solid waste pulp fibres (cellulose) collected from various sewers, and this material is generally landfilled. Stripper condensate represents yet another organic-rich, lower volume, waste stream, and is rich in valuable methanol and mercaptans. Finally, pulp mills also produce on-site power through the combustion of hog fuel (e.g. bark and other low quality wood). The resultant ash contains approximately 50% carbon by weight. Converting the organic matter waste streams from kraft pulp mills into value added products, rather than simply burning them or directing them to landfill, remains a challenge.

Meanwhile, the global demand for energy continues to rise while reserves of conventional petroleum (e.g. oil, gas, and natural gas liquids) are in decline. This has led to increased focus and research into unconventional fuel resources (e.g. heavy oil, oil sands, oil shale) and other non-fossil sources of energy (e.g. lignocellulosic materials). A significant amount of research in the field of "alternative" energy production has focused on the generation of biofuels from lignocellulosic matter. This technology raises the prospect of a shift to an abundant and renewable feedstock for energy production as an alternative to the depleting reserves of hydrocarbon-based raw materials. The enrichment of low energy density fossil fuels (e.g. lignite, peat and oil shale) into high energy fuel products also represents an attractive alternative given the relative abundance of those resources.

In particular, the thermochemical conversion of biomass and other complex organic matter into biofuels and chemicals based on hydrothermal reactions has shown significant promise. Gasification processes are generally conducted at higher temperatures (e.g. 400° C.-700° C.) and can produce methane or hydrogen gases in high yields. Liquefaction processes are generally conducted at lower temperatures (e.g. 200° C.-400° C.) and produce liquid products referred to in the field as "bio-oil" or "bio-crude". To provide a viable replacement or supplement to existing fossil fuels, bio-oils generated from these and related technologies need characteristics (e.g. high energy/yield, low oxygen/water content, reduced viscosity) approximating those of crude oils. Additionally, it is highly important for processes of this nature to be cost-efficient for economic feasibility.

Numerous modifications to improve thermochemical processes for bio-oil production have been developed. For example, the prior removal of hemicellulose under mild conditions from plant materials can improve the production of bio-oils from lignocellulosic feedstocks (see PCT publication No. WO 2010/037178). It has also been demonstrated that rather than gradually heating feedstock slurry to reaction temperature, contacting the slurry with an already supercritical solvent can provide advantageous effects in bio-oil production (see PCT publication No. WO 2012/000033). Incorporating oil into a feedstock slurry, which may also be a recycled bio-oil product, has been shown to improve process efficiency and product characteristics (see PCT publication No. WO 2012/092644). The inclusion of a solid substrate in organic matter feedstock used in thermochemical conversion processes has been shown to reduce scaling and/or reduce the development of pressure differentials during treatment (see PCT application No. PCT/AU2014/00601). Despite these advances, new modifications to thermochemical processes capable of increasing process efficiency, lowering costs and/or improving product characteristics are still desirable.

Many if not most processes for the thermochemical conversion of biomass into biofuels utilize catalysts to increase process efficiency and/or improve product characteristics. A wide range of catalysts have been used in these processes (see, for example, PCT publication No. WO 2011/123897) and the identification of appropriate catalyst combinations and/or alternative sources of catalysts provides an opportunity to improve existing bio-oil production methods.

SUMMARY

This disclosure relates to the discovery that pulping liquors can be used as an effective source of catalysts to facilitate the efficient thermochemical conversion of biomass into biofuels. In view of their organic content (e.g. ligno-cellulosic matter) black liquors may also provide a source of additional feedstock material capable of conversion into bio-products, which can in turn provide a cost benefit by reducing the amount of feedstock material required. A major advantage of using black liquor is that the biocrude product does not require production of in intermediate lignin solid as per other known processes, which reduces operational expenses and avoids significant technical issues associated with handling and selling lignin powder, which is friable, hydrophobic, explosive, and corrosive. This discovery presents a number of opportunities for the integration of Kraft pulp mills with systems for the thermochemical conversion of biomass into biofuels.

The present disclosure relates to the unexpected discovery that pulping liquors such as black liquor can be used as an effective source of catalysts to facilitate the efficient thermochemical conversion of biomass into biofuels. In view of its organic content (e.g. cellulosic matter) pulping liquors also provide a source of additional feedstock material capable of conversion into bio-products, which can in turn provide a cost benefit by reducing the amount of feedstock material required.

The present disclosure provides a method for producing a bio-product from organic matter feedstock, the method comprising: providing a reaction mixture comprising the organic matter feedstock, a solvent, and pulping liquor; treating the reaction mixture in a reactor vessel at a reaction temperature and pressure suitable for conversion of all or a portion of the organic matter feedstock into a product mixture comprising the bio-product; and depressurising and cooling the product mixture; wherein the reaction mixture and product mixture move in continuous flow through reactor vessel during said treating.

In various embodiments, the organic matter feedstock is lignocellulosic feedstock. In various embodiments, the organic matter feedstock is coal feedstock (e.g. lignite feedstock). In various embodiments, the organic matter feedstock and the pulping liquor are both black liquor. In various embodiments, the pulping liquor is black liquor and the organic matter feedstock is not a pulping liquor. In various embodiments, the organic matter feedstock and the pulping liquor both comprise or consist of black pulping liquor (black liquor). In various embodiments, the pulping liquor comprises or consists of black liquor and the organic matter feedstock does not comprise or consist of pulping liquor.

In various embodiments, the pulping liquor is black liquor. The black liquor may have been separated from pulp following a chemical pulping process in which a wood feedstock has been digested with pulping chemicals under heat and pressure. The black liquor may comprise between about 2.5 and 7.0 weight % sodium hydroxide (NaOH) on dry black liquor solids (DBLS), between about 0.06 and 3.0 wt. % sodium sulfide ($Na_2S$), between about 4.5 and about 16.0 wt. % sodium carbonate ($Na_2CO_3$), between about 0.5 g/l and about 5 g/l sodium sulfite ($Na_2SO_3$), between about 1.9 and about 16.6 wt. % sodium sulfate ($Na_2SO_4$), between about 2.4 and about 7.5 wt. % sodium thiosulfate ($Na_2S_2O_3$), and between about 50 and about 70 wt. % organic solids on dry black liquor solids.

The black liquor may comprise between about 1.0 g/l and 2.0 g/l sodium hydroxide (NaOH), between about 3.5 g/l and 5.5 g/l sodium sulfide ($Na_2S$), between about 6.5 g/l and about 9.0 g/l sodium carbonate ($Na_2CO_3$), between about 1.0 g/l and about 3.0 g/l sodium sulfite ($Na_2SO_3$), between about 2.0 g/l and about 4 g/l sodium sulfate ($Na_2SO_4$), between about 2.0 g/l and about 4.5 g/l sodium thiosulfate ($Na_2S_2O_3$), and between about 20 g/l and about 50 g/l organic solids.

The black liquor may comprise between about 4 wt % and 10 wt % sodium hydroxide (NaOH), between about 10 wt % and 30 wt % sodium sulfide ($Na_2S$), between about 25 wt % and about 50 wt % sodium carbonate ($Na_2CO_3$), between about 5 wt % and about 15 wt % sodium sulfite ($Na_2SO_3$), between about 8 wt % and about 20 wt % sodium sulfate ($Na_2SO_4$), between about 10 wt % and about 25 wt % sodium thiosulfate ($Na_2S_2O_3$), and between about 10 wt % and about 90 wt % organic solids or between about 30% and about 70% organic solids.

The black liquor may comprise between about 5 wt % and 9 wt % sodium hydroxide (NaOH), between about 15 wt % and 25 wt % sodium sulfide ($Na_2S$), between about 25 wt % and about 45 wt % sodium carbonate ($Na_2CO_3$), between about 5 wt % and about 15 wt % sodium sulfite ($Na_2SO_3$), between about 10 wt % and about 15 wt % sodium sulfate ($Na_2SO_4$), between about 13 wt % and about 20 wt % sodium thiosulfate ($Na_2S_2O_3$), and between about 40 wt % and about 90 wt % organic solids or between about 50% and about 80% organic solids, or between about 60% and about 75% organic solids.

The black liquor may comprise any one or more of inorganic elements, dissolved wood substances, acetic acid, formic acid, sugars, caboxylic acids, xylans, and methanol.

In various embodiments, the pulping liquor is a green pulping liquor (green liquor). The green liquor may be obtained by processing the black liquor. The green liquor may be obtained by burning the black liquor in an oxygen deficient environment and dissolving the resultant material in a solvent (e.g. water). The concentration of organic solids in the black liquor may be increased prior to burning the black liquor in the oxygen deficient environment to obtain the green liquor. Concentration of the organic solids in the black liquor may be achieved by evaporation.

The green liquor may comprise between about 9 g/l and 20 g/l sodium hydroxide (NaOH), between about 25 g/l and 55 g/l sodium sulfide ($Na_2S$), between about 80 g/l and about 145 g/l sodium carbonate ($Na_2CO_3$), between about 4.0 g/l and about 8.0 g/l sodium sulfite ($Na_2SO_3$), between about 6.0 g/l and about 15.0 g/l sodium sulfate ($Na_2SO_4$), and between about 3.0 g/l and about 9.0 g/l sodium thiosulfate ($Na_2S_2O_3$).

The green liquor may comprise between about 13 g/l and 18 g/l sodium hydroxide (NaOH), between about 30 g/l and 45 g/l sodium sulfide ($Na_2S$), between about 95 g/l and about 120 g/l sodium carbonate ($Na_2CO_3$), between about 5.0 g/l and about 7.0 g/l sodium sulfite ($Na_2SO_3$), between about 9.0 g/l and about 13.0 g/l sodium sulfate ($Na_2SO_4$), and between about 4.0 g/l and about 7.0 g/l sodium thiosulfate ($Na_2S_2O_3$).

The green liquor may comprise between about 4 wt % and 12 wt % sodium hydroxide (NaOH), between about 15 wt % and 25 wt % sodium sulfide ($Na_2S$), between about 50 wt % and about 70 wt % sodium carbonate ($Na_2CO_3$), between about 1 wt % and about 7 wt % sodium sulfite ($Na_2SO_3$), between about 2 wt % and about 10 wt % sodium sulfate ($Na_2SO_4$), and between about 1 wric. and about 5 wt % sodium thiosulfate ($Na_2S_2O_3$).

The green liquor may comprise between about 5 wt % and 10 wt % sodium hydroxide (NaOH), between about 17 wt % and 23 wt % sodium sulfide ($Na_2S$), between about 55 wt % and about 65 wt % sodium carbonate ($Na_2CO_3$), between about 1 wt % and about 4 wt % sodium sulfite ($Na_2SO_3$), between about 3 wt % and about 9 wt % sodium sulfate ($Na_2SO_4$), and between about 1 wr/c, and about 5 wt % sodium thiosulfate ($Na_2S_2O_3$).

In various embodiments, the pulping liquor is a white pulping liquor (white liquor). The white liquor may be obtained by processing the green liquor. The white liquor may be obtained by reacting the green liquor with lime or a derivative thereof (e.g. calcium oxide (CaO), calcium hydroxide (CaOH)). The white liquor may comprise between about 70 g/l and 110 g/l sodium hydroxide (NaOH), between about 30 g/l and 55 g/l sodium sulfide ($Na_2S$), between about 18 g/l and about 40 g/l sodium carbonate ($Na_2CO_3$), between about 3.0 g/l and about 6.0 g/l sodium sulfite ($Na_2SO_3$), between about 6.0 g/l and about 15.0 g/l sodium sulfate ($Na_2SO_4$), and between about 3.0 g/l and about 9.0 g/l sodium thiosulfate ($Na_2S_2O_3$). The white liquor may comprise between about 85 g/l and 105 g/l sodium hydroxide (NaOH), between about 32 g/l and 43 g/l sodium sulfide ($Na_2S$), between about 20 g/l and about 30 g/l sodium carbonate ($Na_2CO_3$), between about 3.5 g/l and about 5.5 g/l sodium sulfite ($Na_2SO_3$), between about 8.0 g/l and about 10.0 g/l sodium sulfate ($Na_2SO_4$), and between about 4.5 g/l and about 7.5 g/l sodium thiosulfate ($Na_2S_2O_3$). The white liquor may comprise between about 40 wt % and 65 wt % sodium hydroxide (NaOH), between about 10 wt % and 30 wt % sodium sulfide ($Na_2S$), between about 8 wt % and about 22 wt % sodium carbonate ($Na_2CO_3$), between about 1 wt % and about 6 wt % sodium sulfite ($Na_2SO_3$), between about 2 wt % and about 10 wt % sodium sulfate ($Na_2SO_4$), and between about 1 wt % and about 5 wt % sodium thiosulfate ($Na_2S_2O_3$). The white liquor may comprise between about 45 wt % and 60 wt % sodium hydroxide (NaOH), between about 15 wt % and 25 wt % sodium sulfide ($Na_2S$), between about 10 wt % and about 20 wt % sodium carbonate ($Na_2CO_3$), between about 2 wt % and about 5 wt % sodium sulfite ($Na_2SO_3$), between about 2 wt % and about 7 wt % sodium sulfate ($Na_2SO_4$), and between about 1.5 wrio and about 4 wt % sodium thiosulfate ($Na_2S_2O_3$).

In various embodiments, the treating comprises treating the reaction mixture at a temperature of between 250° C. and 450° C., and a pressure of between 100 bar and 300 bar. The treating may comprise heating the slurry to a temperature selected from the group consisting of at least about 250° C., at least about 300° C., at least about 350° C., at least about 370° C., at least about 390° C., at least about 400° C., between about 200° C. and about 400° C., between about 200° C. and about 400° C., between about 300° C. and about 400° C., between about 350° C. and about 400° C., and between about 370° C. and about 450° C. The treating may comprise pressurizing the reaction mixture at a pressure of between about 100 bar and about 400 bar, between about 150 bar and about 400 bar, between about 200 bar and about 400 bar, between about 150 bar and about 350 bar, between about 180 bar and about 350 bar, between about 150 bar and about 300 bar, between about 150 bar and about 280 bar, between about 150 bar and about 270 bar, or between about 200 bar and about 300 bar. The treating may comprise treating the reaction mixture at a temperature of between 310° C. and 360° C., and a pressure of between 160 bar and 250 bar. The treating may comprise treating the reaction mixture at a temperature of between 320° C. and 360° C., and a pressure of between 220 bar and 250 bar. The treating may comprise treating the reaction mixture at: (i) a temperature of between 200° C. and 450° C., and a pressure of between 100 bar and 300 bar; (ii) a temperature of between 250° C. and 350° C., and a pressure of between 140 bar and 240 bar.

In various embodiments, the method comprises preparing a slurry comprising the organic matter and the pulping liquor, generating subcritical or supercritical steam independently of the slurry, and contacting the slurry with the subcritical or supercritical steam in at least one vessel or chamber of said reactor vessel. The slurry may comprise lignocellulosic feedstock, coal (e.g. lignite), or a combination thereof. The slurry may be at ambient or near ambient temperature and pressure prior to the contacting with the subcritical or supercritical steam. The treating may comprise heating the slurry to a temperature selected from the group consisting of at least about 100° C., at least about 150° C., at least about 200° C., at least about 250° C., at least about 300° C., at least about 350° C., between about 200° C. and about 250° C., between about 200° C. and about 400° C., between about 250° C. and about 400° C., between about 250° C. and about 350° C., and between about 250° C. and about 350° C.; generating subcritical or supercritical steam independently of the slurry; and contacting the slurry with the subcritical or supercritical steam in at least one vessel or chamber of the reactor vessel. The slurry may be pressurised prior to and/or after said contacting.

In various embodiments, the method comprises preparing a slurry comprising the organic matter, heating the slurry to a temperature of between at least about 100° C., at least about 150° C., at least about 200° C., at least about 250° C., at least about 300° C., at least about 350° C., between about 200° C. and about 250° C., between about 200° C. and about 400° C., between about 250° C. and about 400° C., between about 250° C. and about 350° C., and between about 250° C. and about 350° C.; mixing the pulping liquor with the slurry after heating the slurry to said temperature; and contacting the slurry comprising the lignocellulosic feedstock and black liquor with subcritical or supercritical steam in at least one vessel or chamber of the reactor vessel, wherein the subcritical or supercritical steam is generated independently of the slurry. The slurry may comprise lignocellulosic feedstock, coal (e.g. lignite), or a combination thereof.

In various embodiments, the method comprises a first preheating stage in which the reaction mixture is heated to a temperature that is below the reaction temperature, and a second heating stage in which the reaction mixture is heated to the reaction temperature. The second heating stage may comprise contacting the reaction mixture with subcritical or supercritical steam. In various embodiments, the pulping liquor is mixed with the feedstock and/or solvent prior to the treating.

In various embodiments the pulping liquor is added to the reaction mixture after the reaction mixture reaches said reaction temperature and pressure.

In various embodiments the reaction mixture comprises between 1% and 30%, between 5% and 30%, between 10% and 30%, between 5% and 30%, between 5% and 20%, between 5% and 15%, between 10% and 30%, between 10% and 30%, between 10% and 15%, less than 20%, less than 30%, less than 25%, less than 15%, less than 10%, or less than 5%, of the pulping liquor by weight.

In various embodiments the reaction mixture comprises between 1% and 100%, between 90% and 100%, between 95% and 100%, between 50% and 100%, between 50% and 90%, between 50% and 95%, between 50% and 95%, between 50% and 80%, between 50% and 70%, between 50% and 60%, between 30% and 90%, between 40% and 90%, or between 20% and 75%, of the pulping liquor by weight.

In various embodiments, the reaction mixture comprises less than 20%, less than 30%, less than 35%, less than 40%, less than 40%, less than 70%, less than 80%, less than 90%, less than 95%, between 10% and 95%, between 30% and 95%, between 50% to 70%, or between 60% to 80%, of the solvent by weight.

In various embodiments, the solvent is an aqueous solvent, an oil solvent, or a mixture of an aqueous solvent and an oil solvent. The oil solvent or the mixture of the aqueous solvent and the oil solvent may comprise crude tall oil, distilled tall oil, or a combination thereof. The aqueous solvent may comprise water, water only, or water and an alcohol. The aqueous solvent may comprise water and an alcohol, and the alcohol may be selected from ethanol, methanol, or a combination of methanol and ethanol.

The reaction mixture may comprise a percentage by weight of the alcohol of more than 3%, more than 5%, more than 10%, more than 15%, more than 20%, more than 25%, more than 30%, less than 30%, less than 25%, less than 20%, less than 15%, less than 10%, less than 5%, or less than 3%.

In various embodiments, the lignocellulosic feedstock may be lignocellulosic matter comprising at least 10% lignin, at least 35% cellulose, and at least 20% hemicellulose. The lignocellulosic feedstock may comprise more than about 10% of each of lignin, cellulose, and hemicellulose.

In various embodiments, the reaction mixture comprises more than 10%, more than 15%, more than 20%, more than 30%, more than 35%, or more than 40%, of the organic matter by weight. The organic matter may be lignocellulosic feedstock, coal (e.g. lignite), or a combination thereof.

In various embodiments, the reaction mixture comprises less than 10%, less than 15%, less than 20%, less than 30%, less than 35%, less than 40%, less than 50%, between 5% and 40%, between 10% to 35%, or between 15% and 30%, of the organic matter by weight. The organic matter may be lignocellulosic feedstock, coal (e.g. lignite), or a combination thereof.

In various embodiments, the organic matter is provided in the form of a slurry comprising some or all of the solvent. The organic matter may be lignocellulosic feedstock, coal (e.g. lignite), or a combination thereof. The organic matter may be provided in the form of a slurry comprising some or all of the solvent and/or some or all of the pulping liquor.

The treating may comprise treating the organic matter, the solvent, and the pulping liquor in the form of a slurry with a flow velocity of above 0.01 cm/s, above 0.05 cm/s, above 0.5 cm/s, above 0.1 cm/s, above 1.5 cm/s, or above 2.0 cm/s.

In various embodiments, the reaction mixture is subjected to: (a) heating and pressurization to a target temperature and pressure, (b) treatment at target temperature(s) and pressure(s) for a defined time period (i.e. the "retention time"), and (c) cooling and de-pressurization, under continuous flow conditions.

In various embodiments, the treating is for a time period of between about 20 minutes and about 30 minutes.

In various embodiments, the method comprises the step of heating the organic matter feedstock (e.g. lignocellulosic feedstock, coal (e.g. lignite), or a combination thereof) and solvent to the temperature in a time period of less than about 2 minutes, prior to the treating.

In various embodiments, the method comprises the step of heating and pressurizing the organic matter feedstock (e.g. lignocellulosic feedstock, coal (e.g. lignite), or a combination thereof) and solvent to the temperature and pressure in a time period of less than about 2 minutes, prior to the treating.

In various embodiments, the method comprises the steps of: (i) cooling the product mixture to a temperature of between about 160° C. and about 200° C. in a time period of less than about 30 seconds after said treating; and (ii) depressurization and cooling the product mixture to ambient temperature by release through a pressure let down device.

The pressure let down device may be enveloped in ambient temperature water. The depressurizing and cooling of the product mixture may occur simultaneously. The depressurizing and cooling of the product mixture may occur separately.

In various embodiments the lignocellulosic feedstock is wood.

In various embodiments, the reaction mixture further comprises a solid substrate, wherein the solid substrate is solid or substantially solid at the reaction temperature and pressure, sequesters organic and/or inorganic matter that de-solubilises within the reaction mixture or the product mixture; and/or alters one or more flow characteristics of the reaction mixture and/or the product mixture in the reactor vessel. The organic matter may be lignocellulosic feedstock, coal (e.g. lignite), or a combination thereof. The solid substrate may inhibit scaling in the reactor vessel. The solid substrate may inhibit development of a pressure gradient in the reactor vessel during the conversion of the organic matter feedstock into the bio-product.

The depressurizing may be facilitated by a pressure let down device in the reactor vessel.

The reaction mixture may be pressurized to a maximum pressure prior to or during the treating.

Prior to the depressurizing facilitated by the pressure let down device, the product mixture may be pressurized at less than 98%, less than 95%, less than 90%, less than 85%, less than 80%, less than 75%, less than 70%, less than 65%, less than 60%, less than 55%, or less than 50%, of the maximum pressure.

The solid substrate may generate additional metal surface area within the reactor vessel by an abrasive action, to thereby provide additional metal surface area for provision of additional heterogeneous catalysts to the reaction mixture.

The solid substrate may be inert or substantially inert at the reaction temperature and pressure.

The solid substrate may be chemically inert or substantially chemically inert at the reaction temperature and pressure.

The solid substrate may be a carbonaceous material comprising at least 50%, at least 60%, at least 70%, at least 80%, or at least 90% by weight carbon.

In various embodiments, the solid substrate may be selected from the group consisting of: coals, anthracitic coal, meta-anthracite, anthracite semianthracite, bituminous coal, subbituminous coal, lignite (i.e. brown coal), coking coal, coal tar, coal tar derivatives, coal char, coke, high temperature coke, foundry coke, low and medium temperature coke, pitch coke, petroleum coke, coke oven coke, coke breeze, gas coke, brown coal coke, semi coke, charcoal, pyrolysis char, hydrothermal char, carbon black, graphite fine particles, amorphous carbon, carbon nanotubes, carbon nanofibers, vapor-grown carbon fibers, and any combination thereof.

In various embodiments, the solid substrate may be a non-carbonaceous material comprising no more than 10%, no more than 5%, no more than 1%, or no carbon.

The solid substrate may be selected from the group consisting of fly ash, a mineral, calcium carbonate, calcite, a silicate, silica, quartz, an oxide, a metal oxide, an insoluble or substantially insoluble metal salt, iron ore, a clay mineral, talc, gypsum, and any combination thereof. The solid substrate may be selected from the group consisting of carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof. The solid substrate may be provided in the form of a powder, or a slurry comprising the powder. The solid substrate may be present in the reaction mixture at a concentration of more than 0.5%, more than 1%, more than 3%, more than 5%, more than 10%, more than 25%, or more than 30% by weight. The solid substrate is may be present in the reaction mixture at a concentration of less than 0.5%, less than 1%, less than 3%, less than 5%, less than 10%, less than 25%, or less than 50% by weight. Organic and/or inorganic matter may be sequestered by the solid substrate by adsorbing the organic matter and/or inorganic matter onto a surface of the solid substrate or into the solid substrate.

In various embodiments, the reaction mixture comprises the organic matter feedstock (e.g. lignocellulosic matter) and the solid substrate at a ratio of about 1:1, about 3:2, about 2:1, about 3:1, about 4:1, about 5:1, about 6:1 about 8:1, about 10:1, about 20:1, or about 30:1.

In various embodiments, the solid substrate constitutes: at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, between 1 wt % and 20%, between 1°A) and 10%, between 1% and 5%, between 5% and 10%, between 5% and 15%, between 5% and 20%, between 20% and 40%, between 20% and 50%, between 20% and 30%, between 30% and 40%, or between 40% and 50% of the total combined mass of the solid substrate and organic matter feedstock (e.g. lignocellulosic matter) in the reaction mixture.

In various embodiments, the method further comprises separating the solid substrate from the product mixture after the depressurizing and cooling, and recycling the solid substrate into a second slurry or second reaction mixture comprising organic matter feedstock.

In various embodiments, the solid substrate is made from residue obtained by distillation or pyrolysis of the bio-product.

In various embodiments, the reaction mixture further comprises an oil additive. The oil additive may be mixed with the feedstock and/or solvent prior to the treating. The reaction mixture may comprise between 5% and 60%, between 5% and 50%, between 5% and 40%, between 5% and 30%, between 5% and between 20%, more the 5%, more than 10%, more than 15%, more than 20%, more than 30%, less than 20%, less than 15% or less than 10% of the oil additive by weight. The oil additive may be selected from the group consisting of paraffinic oil, gas-oil, crude oil, synthetic oil, coal-oil, bio-oil, shale oil, kerogen oil, mineral oil, white mineral oil, aromatic oil, tall oil, distilled tall oil, plant or animal oils, fats and their acidic forms and esterified forms, and any combination thereof.

In various embodiments the solvent is a mixed solvent comprising an aqueous solvent component and an oil solvent component, wherein the two components are substantially immiscible or partly miscible at ambient temperature. The oil component may be crude tall oil, distilled tall oil or a combination thereof.

In various embodiments, the solvent comprises water and oil in a ratio of about 1:1 by mass, of about 1:2 by mass, of about 2:1 by mass, of about 3:1 by mass, of about 1:3 by mass, of about 1:4 by mass, of about 4:1 by mass, of about 1:5 by mass, of about 5:1 by mass, of about 1:6 by mass, of about 6:1 by mass, of about 1:7 by mass, of about 7:1 by mass, of about 1:8 by mass, of about 8:1 by mass, of about 1:9 by mass, of about 9:1 by mass, of about 1:10 by mass, or of about 10:1 by mass.

In various embodiments, the method further comprises separating oil from the product and recycling the oil into a second slurry or second reaction mixture comprising organic matter feedstock.

In various embodiments, the method further comprises separating the solid substrate and oil from the product, and recycling the solid substrate and the oil into a second slurry or second reaction mixture comprising organic matter feedstock.

In various embodiments, the oil solvent is recycled from a bio-product produced according to the method.

In various embodiments, the solid substrate is recycled from a bio-product produced according to the method.

In various embodiments, the oil solvent and solid substrate are recycled in a mixture from a bio-product produced according to the method, and the mixture of recycled oil and recycled substrate is solid at ambient temperature.

In various embodiments, the bio-product comprises a compound selected from the group consisting of: waxes; aldehydes; carboxylic acids; carbohydrates; phenols; furfurals; alcohols; ketones; resins; resin acids; compounds structurally related to resin acids; alkanes; alkenes; fatty acids; fatty acid esters; sterols; sterol-related compounds; furanic oligomers; cyclopentanones; cyclohexanones; alkyl- and alkoxy-cyclopentanones; alkyl- and alkoxy-cyclohexanones; cyclopenteneones; alkyl- and alkoxy-cyclopentenones; aromatic compounds; naphthalenes; alkyl- and alkoxy-substituted naphthalenes; cresols; alkyl- and alkoxy-phenols; alkyl- and alkoxy-catechols; alkyl- and alkoxy-dihydroxybezenes; alkyl- and alkoxy-hydroquinones; indenes; indene-derivatives, and any combination thereof.

In various embodiments, the bio-product comprises an oil component having a gross calorific value of at least 30 MJ/kg, at least 32 MJ/kg, at least 35 MJ/kg, or at least 36 MJ/kg.

In various embodiments, the bio-product comprises an oil component having a gross calorific value of at least 30 MJ/kg, at least 32 MJ/kg, at least 35 MJ/kg, or at least 36 MJ/kg, and a mixed substrate and oil component having a gross calorific value of at least 26 MJ/kg, at least 28 MJ/kg, at least 30 MJ/kg, at least 32 MJ/kg, or at least 33 MJ/kg.

In a second aspect, the present invention provides a bio-product obtained by the method of the first aspect.

The bio-product may be a bio-oil.

Further disclosed herein is an integrated Kraft pulp mill and thermochemical conversion system. The system comprises a Kraft pulp mill comprising a digester for digesting a lignocellulosic material with white liquor to produce pulp and black liquors. The system further comprises a thermochemical conversion subsystem that includes: at least one mixing tank for combining pulping liquors received from the pulp mill with an organic matter feedstock and water to produce a reaction mixture; a reactor vessel for treating the reaction mixture received from the mixing tank at a reaction temperature and pressure suitable for conversion of all or a portion of the organic matter in the reaction mixture into a product mixture comprising a bioproduct and an aqueous stream containing both organic and inorganic compounds; and a depressurizer for depressurizing product mixture received from the reactor vessel; The system yet further includes one or more conveyors for conveying the pulping liquors from the pulp mill to the mixing tank.

The pulp mill may include an evaporator for concentrating weak black liquor received from the digester to produce strong black liquor and condensates. The condensates may be organics-enriched condensates. The organics-enriched condensates may include methanol, ethanol, an organic and/or reduced sulphur species, or any combination thereof. The organic or reduced sulphur species may include methyl mercaptan, hydrogen sulphide, dimethyl mercaptan, dimethyl disulfide, or a combination thereof.

The one or more conveyors may include a weak liquor conveyor for conveying weak liquor to the mixing tank, a strong black liquor conveyor for conveying strong black liquor from the evaporators to the mixing tank, a heavy black liquor conveyor for conveying heavy black liquor from a concentrator to the mixing tank, or a combination thereof.

A portion of the black liquors may be entrained in tall oil soap that collects at a surface of the weak black liquor. Accordingly, the system may also include a tall oil soap conveyor for conveying tall oil soap skimmed from the surface of the weak black liquor to the mixing tank.

The system may include at least one water conveyor for conveying water from at least one source of water in the pulp mill to the mixing tank. The at least one source of water in the pulp mill may include: mill water; weak filtrate from brownstock washing; bleaching effluent; clean condensates; dirty condensates; foul condensates; combined condensates; stripper condensates; digester condensates; evaporator condensates; or any combination thereof.

The system may further include at least one steam conveyor for conveying steam from at least one steam source associated with the pulp mill to the reactor vessel. The steam from the at least one steam source associated with the pulp mill may be conveyed to the reactor vessel or the feedstock slurry indirectly via at least one heat exchanger. The at least one steam source may be: a hog fuel boiler; a recovery boiler; a package boiler; a blow tank; a turbine; a condensing turbine; flash steam from the reactor vessel; or any combination thereof.

The thermochemical conversion subsystem may include a separator for separating the reaction product into the bioproduct and separated water. Accordingly, the system may further include at least one separated water conveyor for conveying separated water to the pulp mill or a wastewater water treatment system associated with the pulp mill. The at least one separated water conveyor may be for conveying the separated water to an air or steam stripper for organics removal, a distillation column for organics removal, brownstock washing, a bleach plant, a recausticizer, the wastewater treatment system, or any combination thereof.

The system may further include a steam conveyor for conducting steam from the depressurizer to the pulp mill.

The system may further include at least one organic matter conveyor for conveying organic matter from at least one organic matter source in the pulp mill to the mixing tank to form at least a portion of the reaction mixture. The at least one organic matter source may be: weak black liquor; strong black liquor; condensates; tall oil soap; tall oil; crude sulphate turpentine; knots; screening rejects; black liquor fiber rejects; primary sludge from the wastewater treatment system; secondary sludge from a wastewater treatment plant; hog fuel; wood chips; sawdust; ground wood meal; or any combination thereof.

The system of any one of claims 1 to 16, further comprising one or more detectors for detecting the rate at which the mixing tank receives black liquors, organic matter, condensates, or any combination thereof from the pulp mill.

The system may include an adjustor for adjusting the rate at which organic material is added to the mixing tank and reactor in response to a change in the detected rate at which the mixing tank receives black liquors, organic matter, condensates, or any combination thereof from the pulp mill.

The system may include at least one aqueous stream conveyor for conveying an aqueous stream from the thermochemical conversion subsystem to the pulp mill.

The system may include at least one ash conveyor for conveying ash from at least one ash source in the pulp mill to the mixing tank, wherein the at least one ash source is hog fuel boiler ash, fly ash, or both.

The system may include a dregs conveyor for conveying dregs from green liquor clarifier to the mixing tank for reduction of solids buildup in the bioproduct reactor.

The system may include a non-condensable gas (NCG) conveyor for conveying NCG from the depressurizer to a recovery boiler, a lime kiln, a hog fuel boiler, an NCG incinerator, or any combination thereof, for recovery or destruction of sulphur in the NCG.

The system may include a chlor-alkali plant for provision of caustic and chlorine for digestion and/or bleaching and hydrogen that can go to the hydrotreater in the thermochemical conversion system). Alternatively, the system may include a sodium chlorate plant for provision of chlorine dioxide to a bleaching plant of the pulp mill and hydrogen to a hydrotreater of the thermochemical conversion system. Alternatively, the system may include a hydrogen peroxide plant for supplying hydrogen to a hydrotreater of the thermochemical conversion system. Yet alternatively, the system may include any combination thereof.

Also disclosed herein are methods of producing a bioproduct. The methods comprise digesting a lignocellulosic material with white liquor to produce pulp and black liquor. The method further includes conveying at least a portion of the black liquor to a thermochemical conversion system for combination with an organic matter feedstock and water. The method further includes combining the portion of the black liquor with the organic matter feedstock and water to produce a reaction mixture. The method includes treating the reaction mixture at a reaction temperature and pressure suitable for conversion of all or a portion of the organic matter in the reaction mixture into a product mixture comprising the bioproduct and an aqueous stream. The method may include depressurizing the product mixture.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DEFINITIONS

Figure 1:
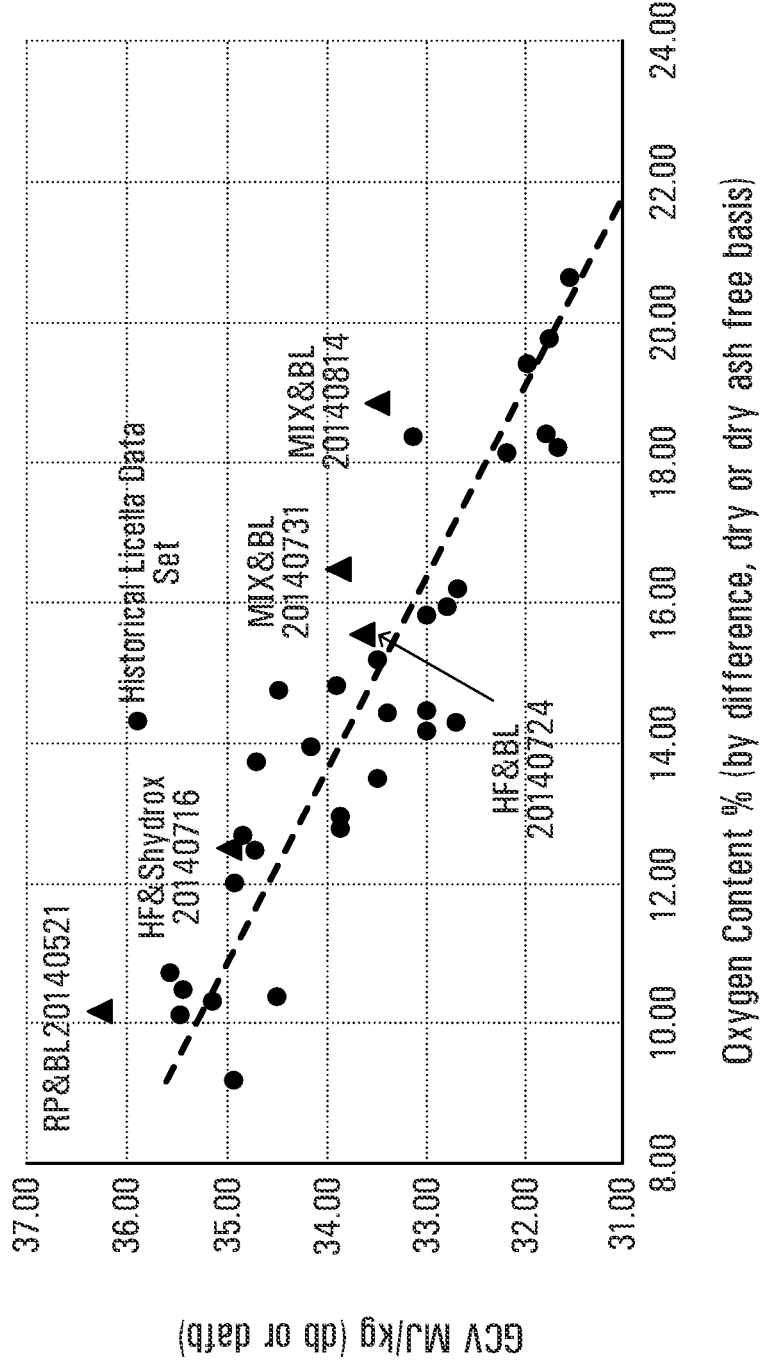
FIG. 1 shows gross calorific value (GCV) vs oxygen content in biocrudes generated from Radiata Pine plus sodium hydroxide (circles), and from hog fuel and black liquor feeds (triangles—as labelled), in accordance with methods of the present invention.

As used in this application, the singular form "a", "an" and "the" include plural references unless the context clearly dictates otherwise.

As used herein, the term "comprising" means "including." Thus, for example, a reaction mixture "comprising" water may include condensates that contain additional components such as dissolved organic matter.

As used herein, a "conveyor" broadly refers to any structure that transports, conducts, or carries matter, whether actively or passively.

As used herein, the terms "organic matter" and "organic materials" have the same meaning and encompass any material comprising carbon including both fossilised and non-fossilised materials. Non-limiting examples of organic matter include renewable sources of biomass (e.g. lignocellulosic matter), as well as hydrocarbon-containing materials (e.g. lignite, oil shale and peat) which may be non-renewable.

As used herein the term "bio-product" encompasses any product that can be obtained by the treatment of organic matter in accordance with the methods disclosed herein. Non-limiting examples of bio-products include biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

As used herein, the term "biofuel" refers to an energy-containing material derived from the treatment of organic matter in accordance with the methods disclosed herein. Non-limiting examples of biofuels include bio-oils, char products (e.g. upgraded pulvarised coal injection (PCI) equivalent products and fuels for direct injection carbon engines (DICE)), and gaseous products (a gaseous product comprising methane, hydrogen, carbon monoxide and/or carbon dioxide).

As used herein the term "bio-oil" refers to a complex mixture of compounds derived from the treatment of organic matter in accordance with the methods disclosed herein. The bio-oil may comprise compounds including, but not limited to, any one or more of alkanes, alkenes, aldehydes, carboxylic acids, carbohydrates, phenols, furfurals, alcohols, and ketones. The bio-oil may comprise multiple phases including, but not limited to, a water-soluble aqueous phase which may comprise, compounds including, but not limited to, any one or more of carbohydrates, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives; and a water-insoluble phase which may comprise, compounds including, but not limited to, any one or more of waxes, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

As used herein, the term "lignocellulosic" encompasses any substance comprising lignin, cellulose, and hemicellulose.

As used herein, the term "fossilized organic matter" encompasses any organic material that has been subjected to geothermal pressure and temperature for a period of time sufficient to remove water and concentrate carbon to significant levels.

As used herein, the term "pulping liquor" will be understood to encompass "black liquor", "green liquor", "white liquor", and any combination thereof.

As used herein, the term "black liquor" refers to an alkaline aqueous solution arising from the treatment of lignocellulosic matter (e.g. pulpwood) into paper pulp using pulping chemicals (e.g. alkaline solution of soda and/or sulfate) which act to free the cellulose fibers from the wood. Black liquor comprises a mixture of dissolved organics (e.g. lignin residues, hemicellulose), inorganic chemicals, and water. Black liquor can be separated from the generated pulp using conventional techniques and may optionally be concentrated by removal of water. "Weak black liquor" may typically be 12%-20% solids by weight. "Strong black liquor" obtained from multiple effect evaporators as described herein may typically be 46-57% solids by weight. "Heavy black liquor" obtained from a concentrator as described herein may be 63%-80% solids by weight. The precise chemical makeup of black liquor will depend on the type of lignocellulosic material subjected to the pulping process, the concentration/make-up of pulping chemicals in the white liquor, and so on. By way of non-limiting example, weak black liquor may comprise 12%-20% solids (50%-70% organics, 20%-40% inorganics), 5-10% NaOH, 15%-30% $Na_2S$, 30%-40% $Na_2CO_3$, 5%-15% $Na_2SO_3$, 8%18% $Na_2SO_4$, and/or 10%-20% $Na_2S_2O_3$. The compositions of weak black liquor sampled from four exemplary kraft pulp mills is summarized in Table 42. The compositions of heavy black liquor sampled from four exemplary kraft pulp mills is summarized in Table 43.

As used herein, the term "green liquor" refers to an aqueous solution of black liquor smelt comprising sodium carbonate. The black liquor smelt may arise from the incineration of black liquor that has been concentrated by the evaporation of water (for example, to over 60% solids content). The precise mechanical make-up of green liquor will depend on factors such as the chemical make-up and degree of solids content of the black liquor material from which it is derived, specifics of the incineration process to produce black liquor smelt, and so on. way of non-limiting example, green liquor may comprise NaOH (5%-10%), $Na_2S$ (15%-25%%), $Na_2CO_3$ (55%-65%), $Na_2SO_3$ (1%-6%), Na2SO4 (3070-90.0)5/and $Na_2S_2O_3$ (1%-6%). The composition of unclarified green liquor sampled from four exemplary kraft pulp mills is summarized in Table 44. The compositions of clarified green liquor sampled from four exemplary kraft pulp mills are summarized in Table 45.

As used herein, the term "white liquor" refers to an alkaline aqueous solution comprising sodium hydroxide and sodium sulfide, and other sodium salts, such as sodium sulfate ($Na_2SO_4$) and sodium carbonate ($Na_2CO_3$) and small amounts of sulfites and chlorides. White liquor may arise from treatment of green liquor with lime ($CaO/Ca(OH)_2$). The green liquor may optionally be clarified to remove insoluble materials (e.g. calcium compounds, unburned carbon, metals) prior to treatment with the lime. The precise chemical makeup of white liquor will depend on factors such as the specific reaction conditions used to prepare it from green liquor, and the nature of the green liquor from which it is derived. By way of non-limiting example, white liquor may comprise between about 48 wt % and 58 wt % sodium hydroxide (NaOH), between about 15 wt % and 25 wt % sodium sulfide ($Na_2S$), between about 10 wt % and about 20 wt % sodium carbonate ($Na_2CO_3$), between about 1 wt % and about 5 wt % sodium sulfite ($Na_2SO_3$), between about 2 wt % and about 7 wt % sodium sulfate ($Na_2SO_4$), and between about 1.5 wt % and about 4 wt % sodium thiosulfate ($Na_2S_2O_3$). The compositions of white liquor sampled from four exemplary kraft pulp mills are summarized in Table 46.

As used herein, the term "solvent" includes an aqueous solvent or an "oil solvent".

As used herein, the term "aqueous solvent" refers to a solvent comprising at least one percent water based on total weight of solvent. An "aqueous solvent" may therefore comprise between one percent water and one hundred percent water based on total weight of solvent. An "aqueous solvent" will also be understood to include within its scope "aqueous alcohol", "aqueous ethanol", and "aqueous methanol". As used herein, the term "aqueous alcohol" refers to a solvent comprising at least one percent alcohol based on total weight of solvent. As used herein, the term "aqueous ethanol" refers to a solvent comprising at least one percent ethanol based on total weight of solvent. As used herein, the term "aqueous methanol" refers to a solvent comprising at least one percent methanol based on total weight of solvent.

As used herein, the term "oil solvent" refers to a solvent comprising any suitable oil, non-limiting examples of which include paraffinic oil, gas-oil, crude oil, synthetic oil, coal-oil, bio-oil, shale oil/kerogen oil, aromatic oils (i.e. single or multi-ringed components or mixtures thereof), tall oils, triglyceride oils, fatty acids, ether extractables, hexane extractables, and any mixture of any of the previous components, and in which the oil constitutes at least one percent of the solvent based on total solvent weight.

As used herein the term "oil additive" refers to any suitable oil component for inclusion in a feedstock, solvent and/or reaction mixture according to the present invention, non-limiting examples of which include paraffinic oil, gas-oil, crude oil, synthetic oil, coal-oil, bio-oil, shale oil/kerogen oil, aromatic oils (i.e. single or multi-ringed components or mixtures thereof), tall oils, triglyceride oils, fatty acids, ether extractables, hexane extractables, and any mixture of any of the previous components. The oil additive may constitute at least one percent portion of the feedstock, solvent and/or reaction mixture to which it is added, based on total weight of the feedstock, solvent and/or reaction mixture.

As used herein, a "supercritical" substance (e.g. a supercritical solvent) refers to a substance that is heated above its critical temperature and pressurised above its critical pressure (i.e. a substance at a temperature and pressure above its critical point).

As used herein, a "subcritical" substance (e.g. a subcritical solvent) refers to a substance at a temperature and/or pressure below the critical point of the substance. Accordingly, a substance may be "subcritical" at a temperature below its critical point and a pressure above its critical point, at a temperature above its critical point and a pressure below its critical point, or at a temperature and pressure below its critical point.

As used herein, a "solid substrate" is a component that is solid or substantially solid at a reaction temperature and pressure used in accordance with the methods of the present invention. The solid substrate may be capable of sequestering organic and/or inorganic matter that de-solubilizes within the reaction mixture and/or a product mixture produced from the reaction mixture. Additionally or alternatively, the solid substrate may be capable of altering the flow characteristics of the reaction mixture or the product mixture in a reactor vessel.

Solid substrates encompass both carbonaceous and non-carbonaceous materials, non-limiting examples of which include coals, anthracitic coal, meta-anthracite, anthracite semianthracite, bituminous coal, subbituminous coal, lignite (i.e. brown coal), coking coal, coal tar, coal tar derivatives, coal char, coke, high temperature coke, foundry coke, low and medium temperature coke, pitch coke, petroleum coke, coke oven coke, coke breeze, gas coke, brown coal coke, semi coke, charcoal, pyrolysis char, hydrothermal char, carbon black, graphite fine particles, amorphous carbon, carbon nanotubes, carbon nanofibers, vapor-grown carbon fibers, fly ash, a mineral, calcium carbonate, calcite, a silicate, silica, quartz, an oxide, a metal oxide, an insoluble or substantially insoluble metal salt, iron ore, a clay mineral, talc, gypsum, carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof.

As used herein, the term "continuous flow" refers to a process wherein a slurry comprising lignocellulosic feedstock and any one or more of: a solvent, solid substrate, pulping liquor, and/or oil additive, is subjected to:
  (a) heating and pressurization to a target temperature and pressure,
  (b) treatment at target temperature(s) and pressure(s) for a defined time period (a "retention time"), and
  (c) cooling and de-pressurization;
during which the slurry is maintained in a stream of continuous movement along the length (or partial length) of a given surface of a reactor vessel. It will be understood that "continuous flow" conditions as contemplated herein are defined by a starting point of heating and pressurization (i.e. (a) above) and by an end point of cooling and de-pressurization (i.e. (c) above). Continuous flow conditions as contemplated herein imply no particular limitation regarding flow velocity of the slurry provided that it is maintained in a stream of continuous movement.

As used herein, the terms "reactor", "reactor apparatus", and "reactor vessel" are used interchangeably and have the same meaning. Each term encompasses any apparatus suitable for performing the methods of the present invention including, for example, continuous flow reactors and batch reactors.

As used herein a "substantially solid" substrate refers to a substrate that is predominantly solid at a specified reaction temperature and/or pressure in that at least 50%, at least 60%, at least 70%, at least 80%, at least 90%, preferably at least 95%, and more preferably at least 98% of the substrate is in a solid form.

As used herein, a "substantially insoluble" substance is one that is predominantly insoluble at a specified reaction temperature and/or pressure in that at least 90%, preferably at least 95%, and more preferably at least 98% of the substrate is not solubilized.

As used herein, an "inert" or "chemically inert" solid substrate is one that does not chemically react with other components in a reaction mixture or catalyse reactions between components in a reaction mixture, at a specified reaction temperature and pressure or at a range of reaction temperatures and pressures.

As used herein, a "substantially inert" or "substantially chemically inert" solid substrate one that does not to any significant degree chemically react with other components in a reaction mixture or catalyze reactions between components in a reaction mixture, at a specified reaction temperature and pressure or at a range of reaction temperatures and pressures. A "substantially inert" or "substantially chemically inert" solid substrate will be understood to react with any other component in a given reaction mixture, or catalyze a reaction between any given components in a reaction mixture, on less than 5%, less than 4%, less than 3%, less than 2%, or less than 1%, of interaction events with the component(s). It will be understood that use of the term "about" herein in reference to a recited numerical value (e.g. a temperature or pressure) includes the recited numerical value and numerical values within plus or minus ten percent of the recited value.

It will be understood that use of the term "between" herein when referring to a range of numerical values encompasses the numerical values at each endpoint of the range. For example, a temperature range of between 10° C. and 15° C. is inclusive of the temperatures 10° C. and 15° C.

DETAILED DESCRIPTION

Black liquor is a waste product of the kraft pulping process in which lignocellulosic matter (e.g. pulpwood) is dissolved under heat and pressure using pulp chemicals. The treatment of the wood in this manner results in a mixture containing pulp and black liquor, a diverse mixture of reacted pulping chemicals/inorganic elements, and dissolved wood substances including acetic acid, formic acid, carboxylic acids, sugars, xylans, and/or methanol. Despite the complex chemical makeup of black liquor and its derivatives, the inventors have discovered that it is a suitable substitute for conventional catalysts used for the thermochemical processing of lignocellulosic matter into bio-oils and related bio-products. Moreover, black liquor contains a significant amount of cellulosic fibers capable of conversion into bio-products via thermochemical processes. Accordingly, the present disclosure provides a means of increasing the cost-efficiency of thermochemical processes for producing bio-products from organic matter feedstocks.

The present disclosure relates to methods for producing bio-products by treating organic matter feedstock with various solvents and in the presence of pulping liquor at increased temperature and pressure. The present disclosure further relates to bio-products generated by the methods described herein.

The present disclosure provides methods for the conversion of organic matter feedstock into bio-products (e.g. biofuels including bio-oils; chemical products etc.).

No limitation exists regarding the particular type of organic matter feedstocks utilised in the methods disclosed herein, although it is contemplated that the use of a solid substrate in accordance with the methods of the present invention may be more beneficial during the conversion of non-fossilized forms of organic matter (e.g. lignocellulosic matter) compared to fossilized forms of organic matter. In preferred embodiments, organic matter utilised in the methods of the invention is or comprises lignocellulosic matter. Lignocellulosic matter as contemplated herein refers to any substance comprising lignin, cellulose and hemicellulose.

The organic material used in the methods described herein may comprise a mixture of two or more different types of lignocellulosic matter, including any combination of the specific examples provided above. The relative proportion of lignin, hemicellulose and cellulose in a given sample will depend on the specific nature of the lignocellulosic matter.

By way of example only, the proportion of hemicellulose in a woody or fibrous plant used in the methods of the invention may be between about 15% and about 40%, the proportion of cellulose may be between about 30% and about 60%, and the proportion of lignin may be between about 5% and about 40%. Preferably, the proportion of hemicellulose in the woody or fibrous plant may be between about 23% and about 32%, the proportion of cellulose may be between about 38% and about 50%, and the proportion of lignin may be between about 15% and about 25%.

In some embodiments, lignocellulosic matter used in the methods of the invention may comprise between about 2% and about 35% lignin, between about 15% and about 45% cellulose, and between about 10% and about 35% hemicellulose.

In other embodiments, lignocellulosic matter used in the methods of the invention may comprise between about 20% and about 35% lignin, between about 20% and about 45% cellulose, and between about 20% and about 35% hemicellulose.

In some embodiments, the lignocellulosic matter may comprise more than about 5%, 10%, 15%, 20%, 25%, 30%, 35%, 40%, 45%, or 50% lignin.

In some embodiments, the lignocellulosic matter may comprise more than about 5%, 10%, 15%, 20%, 25%, 30%, 35%, 40%, 45%, or 50% cellulose.

In some embodiments, the lignocellulosic matter may comprise more than about 5%, 10%, 15%, 20%, 25%, 30%, 35%, 40%, 45%, or 50% hemicellulose.

The skilled addressee will recognize that the methods described herein are not constrained by the relative proportions of lignin, hemicellulose and cellulose in a given source of lignocellulosic matter.

In certain embodiments of the invention, a mixture of organic material comprising lignite (brown coal) and lignocellulosic matter may be utilised as organic matter feedstock in the methods of the invention. The lignocellulosic matter of the mixture may, for example, comprise woody plant material and/or fibrous plant material. The proportion of lignite in the mixture may be greater than about 20%, 40%, 60% or 80%. Alternatively, the proportion of lignocellulosic matter in the mixture may be greater than about 20%, 40%, 60% or 80%.

In some preferred embodiments, organic matter utilised in the methods of the invention comprises carbon-containing polymeric materials, non-limiting examples of which include rubbers (e.g. tyres), plastics and polyamides (e.g. nylons).

Non-limiting examples of suitable rubbers include natural and synthetic rubbers such as polyurethanes, styrene rubbers, neoprenes, polybutadiene, fluororubbers, butyl rubbers, silicone rubbers, plantation rubber, acrylate rubbers, thiokols, and nitrile rubbers.

Non-limiting examples of suitable plastics include PVC, polyethylene, polystyrene, terephtalate, polyethylene and polypropylene.

Organic matter feedstocks utilised in the methods of the invention may comprise carbon-containing wastes such as sewage, manure, or household or industrial waste materials.

Pre-Treatment of Organic Matter

Organic matter utilised in the methods of the present invention may optionally be pre-treated prior converting it into bio-product(s). No strict requirement exists to perform a pre-treatment step when using the methods described herein. For example, pre-treatment of the organic matter may not be required if it is obtained in the form of a liquid or in a particulate form. However, it is contemplated that in many cases pre-treatment of the organic matter may be advantageous in enhancing the outcome of the methods described herein.

In general, pre-treatment may be used to break down the physical and/or chemical structure of the organic matter making it more accessible to various reagents utilized in the methods of the invention (e.g. oil-based solvent, catalysts and the like) and/or other reaction parameters (e.g. heat and pressure). In certain embodiments, pre-treatment of organic matter may be performed for the purpose of increasing solubility, increasing porosity and/or reducing the crystallinity of sugar components (e.g. cellulose). Pre-treatment of the organic matter may be performed using an apparatus such as, for example, an extruder, a pressurized vessel, or batch reactor.

Pre-treatment of the organic matter may comprise physical methods, non-limiting examples of which include grinding, chipping, shredding, milling (e.g. vibratory ball milling), compression/expansion, agitation, and/or pulse-electric field (PEF) treatment.

Additionally or alternatively, pre-treatment of the organic matter may comprise physio-chemical methods, non-limiting examples of which include pyrolysis, steam explosion, ammonia fiber explosion (AFEX), ammonia recycle percolation (ARP), and/or carbon-dioxide explosion. Pre-treatment with steam explosion may additionally involve agitation of the organic matter.

Additionally or alternatively, pre-treatment of the organic matter may comprise chemical methods, non-limiting examples of which include ozonolysis, acid hydrolysis (e.g. dilute acid hydrolysis using $H_2SO_4$ and/or HCl), alkaline hydrolysis (e.g. dilute alkaline hydrolysis using sodium, potassium, calcium and/or ammonium hydroxides), oxidative delignification (i.e. lignin biodegradation catalyzed by the peroxidase enzyme in the presence of $H_2O_2$), and/or the organosolvation method (i.e. use of an organic solvent mixture with inorganic acid catalysts such as $H_2SO_4$ and/or HCl to break lignin-hemicellulose bonds).

Additionally or alternatively, pre-treatment of the organic matter may comprise biological methods, non-limiting examples of which include the addition of microorganisms (e.g. rot fungi) capable of degrading/decomposing various component(s) of the organic matter.

In some embodiments, organic matter used in the methods described herein is lignocellulosic matter which may be subjected to an optional pre-treatment step in which hemicellulose is extracted. Accordingly, the majority of the hemicellulose (or indeed all of the hemicellulose) may be extracted from the lignocellulosic matter and the remaining material (containing predominantly cellulose and lignin) used to produce a biofuel by the methods of the invention. However, it will be understood that this pretreatment is optional and no requirement exists to separate hemicellulose from lignocellulosic matter when performing the methods of the present invention. Suitable methods for the separation of hemicellulose from lignocellulosic matter are described, for example, in PCT publication number WO/2010/034055, the entire contents of which are incorporated herein by reference.

For example, the hemicellulose may be extracted from lignocellulosic matter by subjecting a slurry comprising the lignocellulosic matter (e.g. 5%-15% w/v solid concentration) to treatment with a mild aqueous acid (e.g. pH 6.5-6.9) at a temperature of between about 100° C. and about 250° C., a reaction pressure of between about 2 and about 50 atmospheres, for between about 5 and about 20 minutes. The solubilised hemicellulose component may be separated from the remaining solid matter (containing predominantly cellulose and lignin) using any suitable means (e.g. by use of an appropriately sized filter). The remaining solid matter may be used directly in the methods of the invention, or alternatively mixed with one or more other forms of organic matter (e.g. lignite) for use in the methods of the invention.

Slurry Characteristics

Organic matter feedstock utilized in accordance with the methods of the present invention is preferably treated in the form of a slurry. Accordingly, the reaction mixture may be in the form of a slurry.

The slurry may comprise the organic matter in combination with a solvent (e.g. an aqueous solvent, an aqueous alcohol solvent, an aqueous ethanol solvent, an aqueous methanol solvent) optionally in combination with pulping liquor, solid substrate, a catalyst additive, and/or an oil additive. The slurry may be generated, for example, by generating a particulate form of the organic matter (e.g. by physical methods such as those referred to above and/or by other means) and mixing with the solvent.

No particular limitation exists regarding the relative proportions of solvent, feedstock, oil additive and/or solid substrate in the slurry. Non-limiting examples of potential quantities of these various components are described in the sections below.

Organic Matter Feedstock Component

A slurry for use in accordance with the methods described herein will generally comprise organic matter feedstock.

In certain embodiments of the invention, the concentration of organic matter in the slurry may be less than about 85 wt %, less than about 75 wt %, or less than about 50 wt %. Alternatively, the concentration of organic matter may be more than about 10 wt %, more than about 20 wt %, more than about 30 wt %, more than about 40 wt %, more than about 50 wt %, or more than about 60 wt %.

In some embodiments the slurry may comprise between about 35 wt % and about 45 wt % of an oil additive. In other embodiments, the slurry may comprise about 40 wt % oil or 39.5 wt % of an oil additive.

The optimal particle size of solid components of the organic matter feedstock and the optimal concentration of those solids in the slurry may depend upon factors such as, for example, the heat transfer capacity of the organic matter utilized (i.e. the rate at which heat can be transferred into and through individual particles), the desired rheological properties of the slurry and/or the compatibility of the slurry with component/s of a given apparatus within which the methods of the invention may be performed (e.g. reactor tubing). The optimal particle size and/or concentration of solid components of the organic matter components in a slurry used for the methods of the present invention can readily be determined by a person skilled in the art using standard techniques. For example, a series of slurries may be generated, each sample in the series comprising different particle sizes and/or different concentrations of the solid organic matter components compared to the other samples. Each slurry can then be treated in accordance with the methods of the invention under a conserved set of reaction conditions. The optimal particle size and/or concentration of solid organic matter components can then be determined upon analysis and comparison of the products generated from each slurry using standard techniques in the art.

In certain embodiments of the invention, the particle size of solid organic matter components in the slurry may be between about 10 microns and about 10,000 microns. For example, the particle size may be more than about 50, 100, 500, 750, 1000, 2000, 3000, 4000, 5000, 6000, 7000, 8000 or 9000 microns. Alternatively, the particle size may less than about 50, 100, 500, 750, 1000, 2000, 3000, 4000, 5000, 6000, 7000, 8000 or 9000 microns. In some embodiments, the particle size is between about 10 microns and about 50 microns, between about 10 microns and about 100 microns, between about 10 microns and about 200 microns, between about 10 microns and about 500 microns, between about 10 microns and about 750 microns, or between about 10 microns and about 1000 microns. In other embodiments, the particle size is between about between about 100 microns and about 1000 microns, between about 100 microns and about 750 microns, between about 100 microns and about 500 microns, or between about 100 microns and about 250 microns.

Pulping Liquor Component

A slurry for use in accordance with the methods of the present invention will generally comprise a pulping liquor component. The pulping liquor may be included in the slurry prior to heating and/or pressurizing the slurry to target reaction conditions. Additionally or alternatively, the pulping liquor may be included in the slurry while the slurry is undergoing heating and/or pressurizing to target reaction conditions. Additionally or alternatively, the pulping liquor may be included in the slurry after it has undergone heating and/or pressurizing to target reaction conditions.

In some embodiments the slurry may comprise pulping liquor (black liquor, green liquor, white liquor, or any combination thereof).

For example, the slurry may comprise between about 1% and about 100%, between about 90% and about 100%, between about 95% and about 100%, between about 50% and about 100%, between about 50% and about 90%, between about 50% and about 95%, between about 50% and about 95%, between about 50% and about 80%, between about 50% and about 70%, between about 50% and about 60%, between about 30% and about 90%, between about 40% and about 90%, or between about 20% and about 75%, of the pulping liquor by weight.

For example, the slurry may comprise between about 60 wt % and about 100 wt % of the pulping liquor, between about 5 wt % and about 60 wt %, between about 1 wt % and about 50 wt %, between about 1 wt % and about 40 wt %, between about 1 wt % and about 30 wt %, between about 1 wt % and about 20 wt %, between about 1 wt % and about 15 wt %, between about 1 wr/o and about 10 wt %, between about 1 wt % and about 5 wt %, between about 2 wt % and about 20 wt %, between about 2 wt % and about 10 wt %, between about 3% and about 20 wt %, between about 3 wt % and about 10 wt %, between about 0.5 wt % and about 5 wt %, between about 2 wt % and about 8 wt %, between about 3 wt % and about 5 wt %, or between about 5 wt % and about 15 wrio of the pulping liquor.

In some embodiments, the pulping liquor (black liquor, green liquor, white liquor, or any combination thereof) may be used in an amount of between about 0.1% and about 10% w/v pulping liquor, between about 0.1% and about 7.5% w/v pulping liquor, between about 0.1% and about 5% w/v pulping liquor, between about 0.1% and about 2.5% w/v pulping liquor, between about 0.1% and about 1% w/v pulping liquor, or between about 0.1% and about 0.5% w/v pulping liquor (in relation to the solvent).

Solvent Component

A slurry for use in accordance with the methods described herein will generally comprise a solvent component. The solvent may be an aqueous solvent, an oil solvent, or a combination thereof.

The solvent may comprise or consist of water.

In certain embodiments, the concentration of water in the slurry may be above about 80 wt %, above about 85 wt %, or above about 90 wt %. Accordingly, the concentration of water may be above about 75 wt %, above about 70 wt %, above about 60 wt %, above about 50 wt %, above about 40 wt %, or above about 30 wt %. In some embodiments, the concentration of water is between about 90 wt % and about 95 wt %.

In some embodiments the slurry comprises between about 10 wt % and about 30 wt % water. In other preferred embodiments, the slurry comprises about 20 wt % oil or about 15 wt % water.

In some embodiments, the water is recycled from the product of the process. For example, a portion water present following completion of the reaction may be taken off as a side stream and recycled into the slurry.

The solvent may comprise or consist of one or more aqueous alcohol/s. For example, it may be suitable or preferable to use an aqueous alcohol as the solvent when the lignocellulosic feedstock used in the methods consists of or comprises a significant amount of lignocellulosic material and/or other materials such rubber and plastics due to the stronger chemical bonds in these types of lignocellulosic feedstock. Suitable alcohols may comprise between one and about ten carbon atoms. Non-limiting examples of suitable alcohols include methanol, ethanol, isopropyl alcohol, isobutyl alcohol, pentyl alcohol, hexanol and iso-hexanol.

The slurry may comprise more than about 5 wt %, 10 wt %, 15 wt %, 20 wt %, 25 wt %, 30 wt %, 35 wt %, 40 wt %, 45 wt % or 50 wt % alcohol aqueous alcohol.

In certain embodiments, the solvent comprises a mixture of two or more aqueous alcohols.

Preferably, the alcohol is ethanol, methanol or a mixture thereof.

Solid Substrate Component

A slurry for use in accordance with the methods described herein may comprise a solid substrate component as described herein.

Favourable characteristics of the solid substrate may include any one or more of the following: it remains inert or substantially inert at the reaction temperature and pressure used; it remains unaltered or substantially unaltered upon completion of the process; it remains as a solid or substantially solid at the reaction temperatures and pressures used; it is of low or moderate hardness so that it does not induce substantial abrasion or erosive corrosion in reactors (e.g. continuous flow reactors); it has a high internal or external specific surface area so that it can adsorb and/or absorb large quantities of bio-products and/or other precipitates during the conversion process.

The solid substrate may be a carbonaceous material. By way of non-limiting example only, the solid substrate may be a carbonaceous material comprising at least 50%, at least 60%, at least 70%, at least 80%, at least 90%, or at least 95% by weight carbon.

Non-limiting examples of suitable carbonaceous materials for use as the solid substrate include coals (e.g. anthracitic coals such as meta-anthracite, anthracite and semianthracite; bituminous coals, subbituminous coals, lignite (i.e.

brown coal), coking coal, coal tar, coal tar derivatives, coal char); cokes (e.g. high temperature coke, foundry coke, low and medium temperature coke, pitch coke, petroleum coke, coke oven coke, coke breeze, gas coke, brown coal coke, semi coke); charcoal; pyrolysis char; hydrothermal char; carbon black; graphite fine particles; amorphous carbon; carbon nanotubes; carbon nanofibers; vapor-grown carbon fibers; and any combination thereof.

In some preferred embodiments described herein the solid substrate may be a carbon rich char made from the previous processing of organic matter according to the present invention followed by a thermal treatment in the substantial absence of oxygen to remove volatile materials (e.g. by pyrolysis or vacuum distillation at temperatures in the range of 200° C. to 800° C.).

The solid substrate may be a non-carbonaceous material. By way of non-limiting example only, the solid substrate may be a non-carbonaceous material comprising less than 20%, less than 10%, less than 5%, less than 3%, less than 2%, or less than 1°/o, by weight carbon, or comprise no carbon.

Non-limiting examples of suitable non-carbonaceous materials for use as the solid substrate include ash (e.g. fly ash); minerals (e.g. calcium carbonate, calcite, silicates, silica, quartz, oxides including iron ore, clay minerals, talc, gypsum); an insoluble or substantially insoluble metal salt; and any combination thereof.

Further non-limiting examples of suitable materials for use as the solid substrate include carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof.

In certain embodiments of the present invention, the concentration of solid substrate in the slurry may be less than about 20 wt %, less than about 15 wt %, or less than about 10 wt %. Alternatively, the concentration of solid substrate may be more than about 0.5 wt %, more than about 1 wt %, more than about 3 wt %, more than about 5 wt %, more than about 50 8 wt %, or more than about 10 wt %.

The optimal particle size and optimal concentration of the solid substrate may depend upon factors such as, for example, the heat transfer capacity of the organic matter utilised (i.e. the rate at which heat can be transferred into and through individual particles), the desired rheological properties of the slurry and/or the compatibility of the slurry with component/s of a given apparatus within which the methods of the invention may be performed (e.g. reactor tubing). The optimal particle size and/or concentration of the solid substrate component in a slurry used for the methods of the invention can readily be determined by a person skilled in the art using standard techniques. For example, a series of slurries may be generated, each sample in the series comprising a specific solid substrate of different size and/or different concentration to those of other samples. Each slurry can then be treated in accordance with the methods of the invention under a conserved set of reaction conditions. The optimal solid substrate size and/or concentration can then be determined upon analysis and comparison of the products generated from each slurry using standard techniques in the art.

In certain embodiments of the invention, the size of a solid substrate component in the slurry may be between about 10 microns and about 10,000 microns. For example, the size may be more than about 50, 100, 500, 750, 1000, 2000, 3000, 4000, 5000, 6000, 7000, 8000 or 9000 microns. Alternatively, the size may less than about 50, 100, 500, 750, 1000, 2000, 3000, 4000, 5000, 6000, 7000, 8000 or 9000 microns. In some embodiments, the size is between about 10 microns and about 50 microns, between about 10 microns and about 100 microns, between about 10 microns and about 200 microns, between about 10 microns and about 500 microns, between about 10 microns and about 750 microns, or between about 10 microns and about 1000 microns. In other embodiments, the size is between about between about 100 microns and about 1000 microns, between about 100 microns and about 750 microns, between about 100 microns and about 500 microns, or between about 100 microns and about 250 microns.

In some embodiments of the invention, the particle size distributions and particle surface charge characteristics of the organic matter component of the slurry and/or the solid substrate component of the slurry may be optimized in order to provide desirable slurry characteristics when mixed, for example, to obtain minimum viscosity for a given solids content. The optimal particle size and/or particle surface charge of solid components in a given slurry used can readily be determined by a person skilled in the art using standard techniques. For example, a series of slurries may be generated, each sample in the series comprising different particle sizes and/or different concentrations of solid components compared to the other samples. Each slurry can then be treated in accordance with the methods of the invention under a conserved set of reaction conditions. The optimal particle size and/or particle surface charge of solid organic matter components can then be determined upon analysis and comparison of the products generated from each slurry using standard techniques known in the art.

Catalysts

Although the present invention contemplates the use of pulping liquors as an adequate source of catalysts for converting organic matter into bio-products using the methods described herein, intrinsic catalysts and/or additional catalysts may be employed if so desired.

An "intrinsic catalyst" is catalyst that is innately present in a given reaction component such as, for example, any one or more of organic matter feedstock, an aqueous solvent, and/or vessel walls of a reactor apparatus, or, a catalyst that form in situ during the treatment process.

As used herein, a "additional catalysts" is a catalyst incorporated into a feedstock slurry and/or reaction mixture that is supplementary to catalytic compounds present in pulping liquor included in the feedstock slurry, and supplementary to catalytic compounds intrinsically present in organic matter feedstock treated in accordance with the methods of the invention, catalytic compounds intrinsically present in any solvent used in accordance with the methods of the invention, catalytic compounds intrinsically present in a solid substrate used to perform the methods of the invention, and/or catalytic compounds intrinsically present in the walls of a reactor apparatus used to perform the methods of the invention.

Although the use of additional catalyst additive/s (i.e. beyond those in intrinsic catalysts) may be advantageous in certain circumstances, the skilled addressee will recognise that the methods of the invention may be performed without using them.

A catalyst additive as contemplated herein may be any catalyst that enhances the formation of biofuel from organic matter (e.g. lignocellulosic feedstock and/or coals such as lignite) using the methods of the invention, non-limiting examples of which include base catalysts, acid catalysts, alkali metal hydroxide catalysts, transition metal hydroxide catalysts, alkali metal formate catalysts, transition metal formate catalysts, reactive carboxylic acid catalysts, transition metal catalysts, sulphide catalysts, noble metal catalysts, water-gas-shift catalysts, and combinations thereof. Suitable catalysts are described, for example, in United States of America patent publication number 2012-0311658 A1 entitled "Methods for biofuel production", the entire contents of which are incorporated herein by reference.

In certain embodiments, an additional catalyst or combination of additional catalysts may be used in an amount of between about 0.1% and about 10% w/v catalysts, between about 0.1% and about 7.5% w/v catalysts, between about 0.1% and about 5% w/v catalysts, between about 0.1% and about 2.5% w/v catalysts, between about 0.1% and about 1% w/v catalysts, or between about 0.1% and about 0.5% w/v catalysts (in relation to the solvent).

Table 1 below provides a summary of various exemplary additional catalysts that may be employed in the methods of the invention and the corresponding reactions that they may catalyze.

TABLE 1

Summary catalysts and corresponding reactions

| Reaction Type | Catalyst Family | Catalyst Family Member | Specific example(s) | Preferred catalysts/comments |
|---|---|---|---|---|
| Hydrolysis | Base catalysts | Sub/super-critical water | Hydroxide ion in sub/super-critical water | |
| | | All alkali and transition metal salts, both cations and anions can contribute. Include all common inorganic anions | M = any alkali or transition metal A = anions, including: aluminate, sulfate, sulfite, sulfide phosphate, phosphite nitrate, nitrite silicate hydroxide alkoxide carbonate oxide | M = Na, K, Fe, Ca, Ba A = aluminate, phosphate, silicate, hydroxide, methoxide, ethoxide carbonate sulphate sulphide disulphide (FeS$_2$) oxide |
| | | Any organic ammonia, base pyridine, etc. | | |
| Hydrolysis | Acid catalysts (slower) | Sub/super-critical water | Hydronium ion in sub/super-critical water | |
| | | Any liquid mineral or organic acid | HA, where A = anions, including: aluminate, sulfate, sulfite, sulfide phosphate, phosphite nitrate, nitrite silicate hydroxide alkoxide carbonate carboxy group | Acids may form from the in-situ formation of carboxylic acids, phenolics and the presence of minerals |
| Dehydration (elimination) | Acid catalysts | Sub/super-critical water | Hydronium ion in sub/super-critical water | |
| | | Any liquid mineral or organic acid | HA, where A = anions, including: aluminate, sulfate, sulfite, sulfide phosphate, phosphite nitrate, nitrite silicate | Acids may form from the in-situ formation of carboxylic acids, phenolics and the presence of minerals. zeolites or alumino-silicates in general may be added |

TABLE 1-continued

Summary catalysts and corresponding reactions

| Reaction Type | Catalyst Family | Catalyst Family Member | Specific example(s) | Preferred catalysts/comments |
|---|---|---|---|---|
| | | | hydroxide alkoxide carbonate carboxy group | |
| Transfer Hydrogenation or in-situ $H_2$ generation | Transfer hydrogenation catalysts | All alkali and transition metal hydroxides and formates | M = any alkali or transition metal | M = Na, K |
| | | All reactive carboxylic acids | A hydroxide, formate | A = hydroxide, formate formic, acetic |
| | | All transition and noble metals | All transition and noble metals | M = Fe, Pd, Pd, Ni Ru Rh |
| Decarboxylation | Largely thermal | Acid and transition (noble) metal cats have been reported to aid the process | All transition and noble metals supported on solid acids | $Pt/Al_2O_3/SiO_2$ $Pd/Al_2O_3/SiO_2$ $Ni/Al_2O_3/SiO_2$ |
| Decarbonylation | Largely thermal | As for decarboxylation | As for decarboxylation | As for decarboxylation |
| In-situ gasification | Largely thermal | Transition metals | supported transition metals sulfides | $Pt/Al_2O_3/SiO_2$ $Pd/Al_2O_3/SiO_2$ $Ni/Al_2O_3/SiO_2$ Fe $Fe_xS_y$ $FeS/Al_2O_3$ $FeS/SiO_2$ $FeS/Al_2O_3/SiO_2$ |
| Water-Gas Shift | WGS catalysts | Standard WGS catalysts | As per literature | As per literature |
| Direct Hydrogenation with $H_2$ | Transition metals | Zero valent metals Sulfides | | Fe, Pt, P, Ni as zero valent FeS, $Fe_xSy$ |
| Hydrode-oxygenation | Combined acid and hydrogenation catalyst | Transition metal and solid acid | M = transition metal A = acidic solid | $Pt/Al_2O_3/SiO_2$ $Pd/Al_2O_3/SiO_2$ $Ni/Al_2O_3/SiO_2$ $NiO/MoO_3$ $CoO/MoO_3$ $NiO/WO_2$ zeolites loaded with noble metals, e.g. ZSM-5, Beta, ITQ-2 |

Additional catalysts for use in the methods of the invention may be produced using chemical methods known in the art and/or purchased from commercial sources.

No particular limitation exists regarding the timing at which the additional catalysts may be applied when performing the methods of the invention. For example, the catalyst additive(s) may be added to the organic matter, solvent, pulping liquor, solid substrate, oil additive, or a mixture of one or more of these components (e.g. a slurry) before heating/pressurization to target reaction temperature and pressure, during heating/pressurization to target reaction temperature and pressure, and/or after reaction temperature and pressure are reached. The timing at which the additional catalyst is applied may depend on the reactivity of the feedstock utilized. For example, highly reactive feedstocks may benefit from applying the additional catalyst close to or at the target reaction temperature and pressure, whereas less reactive feedstocks may have a broader process window for applying the additional catalyst (i.e. the catalysts may be added prior to reaching target reaction temperature and pressure).

The additional catalysts may be included in a reaction mixture used for treatment according to the present invention prior to heating and/or pressurizing the reaction mixture, during heating and/or pressurizing of the reaction mixture, and/or after the reaction mixture reaches a desired reaction temperature and/or reaction pressure.

Oil Component

In some preferred embodiments described herein, the slurry, the reaction mixture, or both comprises organic matter mixed with an oil additive. The oil additive may act as an oil-solvent in the reaction. The oil may be any suitable oil, non-limiting examples of which include paraffinic oil, gas-oil, crude oil, synthetic oil, coal-oil, bio-oil, shale oil/kerogen oil, aromatic oils (i.e. single or multi-ringed components or mixtures thereof), tall oils, triglyceride oils, fatty acids, ether extractables, hexane extractables and any mixture of any of the previous components. The oil may be incorporated into the slurry mixture at any point before target reaction temperature and/or pressure are reached. For example, the oil may be added to the slurry in a slurry mixing tank. Additionally or alternatively, the oil may be added to the slurry en route to a reactor and/or during heating/pressurization of the slurry.

In particularly preferred embodiments, the oil is a bio-oil product recycled from the process. For example, a portion of the bio-oil produced may be taken off as a side stream and recycled into the slurry, reaction mixture, or both.

In some preferred embodiments, the bio-oil is recycled in combination with solid substrate, each being a component of the bio-product. For example, a portion of the bio-oil produced mixed with solid substrate may be taken off as a side stream and recycled into the slurry, reaction mixture, or both.

No particular limitation exists regarding the proportion of oil additive in a slurry comprising organic matter treated in accordance with the methods of the present invention. For example, the slurry may comprise more than about 2 wt % oil, more than about 5 wt % oil, more than about 10 wt % oil, or more than about 20, 30, 40, 50, 60 or 70 wt % oil. Alternatively, the slurry may comprise less than about 98 wt % oil, less than about 95 wt % oil, less than about 90 wt % oil, or less than about 80, 70, 60, 50, 40 or 30 wt % oil.

In some preferred embodiments the slurry comprises between about 10 wt % and about 30 wt % organic matter, between about 2 wt % and about 15 wt % solid substrate, and between about 50 wt % and about 90 wt % solvent where the solvent is a mixture of oil and aqueous phase in any proportion.

In some preferred embodiments, the slurry comprises between about 40 wt % and about 50 wt % oil. In other preferred embodiments, the slurry comprises about 45 wt % oil.

In other preferred embodiments the slurry comprises a feedstock to oil ratio of 0.51.2:1. The oil may be paraffinic oil.

Reaction Conditions

In accordance with the methods of the present invention, organic matter feedstock (e.g. lignocellulosic matter and/or coal such as lignite) may be treated with a solvent in the presence of pulping liquor as described herein, and optionally in the presence of an oil additive, solid substrate, and/or additive catalysts, under conditions of increased temperature and pressure to produce bio-products.

The specific conditions of temperature and pressure used when practicing the methods of the invention may depend on a number different factors including, for example, the type of solvent used, the type of organic matter feedstock under treatment, the physical form of the organic matter feedstock under treatment, the relative proportions of components in the reaction mixture (e.g. the proportion of solvent, pulping liquor, organic matter feedstock, and optionally additive oil, catalyst additives, and/or any other additional component/s), the types of additive catalyst(s) utilized (if present), the retention time, and/or the type of apparatus in which the methods are performed. These and other factors may be varied in order to optimize a given set of conditions so as to maximize the yield and/or reduce the processing time. In preferred embodiments, all or substantially all of the organic material used as a feedstock is converted into bio-product(s).

Desired reaction conditions may be achieved, for example, by conducting the reaction in a suitable apparatus (e.g. a sub/supercritical reactor apparatus) capable of maintaining increased temperature and increased pressure.

Temperature and Pressure

According to the methods of the present invention a reaction mixture is provided and treated at a target temperature and pressure for a fixed time period ("retention time") facilitating the conversion of organic matter feedstock (e.g. lignocellulosic matter and/or coal such as lignite) into bio-product(s). The temperature and/or pressure required to drive conversion of organic feedstock into biofuel using the methods of the invention will depend on a number of factors including the type of organic matter under treatment and the relative proportions of components in the reaction (e.g. the proportion of solvent, pulping liquor, organic matter feedstock, and optionally additive oil, catalyst additives, and/or any other additional component/s), the type and amount of pulping liquor used, the retention time, and/or the type of apparatus in which the methods are performed. Based on the description of the invention provided herein the skilled addressee could readily determine appropriate reaction temperature and pressure for a given reaction mixture. For example, the optimal reaction temperature and/or pressure for a given feedstock slurry may be readily determined by the skilled addressee by preparing and running a series of reactions that differ only by temperature and/or pressure utilized and analyzing the yield and/or quality of the target bio-product(s) produced. Proportions of relative components in the reaction mixture can be varied and the same tests conducted again at the same of different temperatures and/or pressures.

The skilled addressee will also recognize that the pressure utilized is a function of the slurry components and pressure drop, induced by the slurry, and strongly dependent on any particular reactor design (e.g. pipe diameter and/or length etc).

In certain embodiments, treatment of organic matter feedstock to produce a bio-product using the methods of the invention may be conducted at temperature(s) of between about 150° C. and about 550° C. and pressure(s) of between about 10 bar and about 400 bar. Preferably, the reaction mixture is maintained at temperature(s) of between about 150° C. and about 500° C. and pressure(s) of between about 80 bar and about 350 bar. More preferably the reaction mixture is maintained at temperature(s) of between about 180° C. and about 400° C. and pressure(s) of between about 100 bar and about 330 bar. Still more preferably the reaction mixture is maintained at temperature(s) of between about 200° C. and about 380° C. and pressure(s) of between about 120 bar and about 250 bar.

In preferred embodiments, the reaction mixture is maintained at temperature(s) of between about 200° C. and about 400° C., and pressure(s) of between about 100 bar and about 300 bar.

In other preferred embodiments, the reaction mixture is maintained at temperature(s) of between about 250° C. and about 380° C., and pressure(s) of between about 50 bar and about 300 bar.

In other preferred embodiments, the reaction mixture is maintained at temperature(s) of between about 320° C. and about 360° C. and pressure(s) of between about 150 bar and about 250 bar. In other preferred embodiments, the reaction mixture is maintained at temperature(s) of between about 330° C. and about 350° C. and pressure(s) of between about 230 bar and about 250 bar. In another particularly preferred embodiment, the reaction mixture is maintained at temperature(s) of about 340° C. and pressure(s) of between about 240 bar.

In other preferred embodiments, the reaction mixture is maintained at temperature(s) of between about 320° C. and about 360° C., and pressure(s) of between about 220 bar and about 250 bar.

In certain embodiments, the reaction mixture is maintained at temperature(s) of above about 180° C. and pressure(s) above about 150 bar. In other embodiments, the reaction mixture is maintained at temperature(s) of above about 200° C. and pressure(s) above about 180 bar. In additional embodiments, reaction mixture is maintained at temperature(s) of above about 250° C. and pressure(s) above about 200 bar. In other embodiments, reaction mixture is maintained at temperature(s) of above about 300° C. and pressure(s) above about 250 bar. In other embodiments, reaction mixture is maintained at temperature(s) of above about 350° C. and pressure(s) above about 300 bar.

It will be understood that in certain embodiments a solvent used in the methods of the present invention may be heated and pressurized beyond its critical temperature and/or beyond its critical pressure (i.e. beyond the 'critical point' of the solvent). Accordingly, the solvent may be a 'supercritical' solvent if heated and pressurized beyond the 'critical point' of the solvent.

In certain embodiments a solvent used in the methods of the present invention may be heated and pressurized to level(s) below its critical temperature and pressure (i.e. below the 'critical point' of the solvent). Accordingly, the solvent may be a 'subcritical' solvent if its maximum temperature and/or maximum pressure is below that of its 'critical point'. Preferably, the 'subcritical' solvent is heated and/or pressurized to level(s) approaching the 'critical point' of the solvent (e.g. between about 10° C. to about 50° C. below the critical temperature and/or between about 10 atmospheres to about 50 atmospheres below its critical pressure).

In some embodiments, a solvent used in the methods of the present invention may be heated and pressurized to levels both above and below its critical temperature and pressure (i.e. heated and/or pressurized both above and below the 'critical point' of the solvent at different times). Accordingly, the solvent may oscillate between 'subcritical' and 'supercritical' states when performing the methods.

Retention Time

The specific time period over which the conversion of organic matter feedstock (e.g. lignocellulosic matter and/or coals such as lignite) may be achieved upon reaching a target temperature and pressure (i.e. the "retention time") may depend on a number different factors including, for example, the type of organic matter under treatment and the relative proportions of components in the reaction (e.g. the proportion of solvent, pulping liquor, organic matter feedstock, and optionally additive oil, catalyst additives, and/or any other additional component/s), and/or the type of apparatus in which the methods are performed. These and other factors may be varied in order to optimize a given method so as to maximize the yield and/or reduce the processing time. Preferably, the retention time is sufficient to convert all or substantially all of the organic material used as a feedstock into bio-product(s).

In certain embodiments, the retention time is less than about 60 minutes, 45 minutes, 30 minutes, 25 minutes, 20 minutes, 15 minutes, 10 minutes or less than about 5 minutes. In certain embodiments, the retention time is more than about 60 minutes, 45 minutes, 30 minutes, 25 minutes, 20 minutes, 15 minutes, 10 minutes or more than about 5 minutes. In other embodiments, the retention time is between about 1 minute and about 60 minutes. In additional embodiments, the retention time is between about 5 minutes and about 45 minutes, between about 5 minutes and about 35 minutes, between about 10 minutes and about 35 minutes, or between about 15 minutes and about 30 minutes. In further embodiments, the retention time is between about 20 minutes and about 30 minutes.

The optimal retention time for a given set of reaction conditions as described herein may be readily determined by the skilled addressee by preparing and running a series of reactions that differ only by the retention time, and analyzing the yield and/or quality of bio-product(s) produced.

Heating/Cooling, Pressurization/De-Pressurization

A reaction mixture (e.g. in the form of a slurry) comprising organic matter feedstock (e.g. lignocellulosic matter and/or coals such as lignite), solvent, pulping liquor, and optionally one or more catalyst additives as defined herein may be brought to a target temperature and pressure (i.e. the temperature/pressure maintained for the "retention time") over a given time period.

Reaction mixes that do not contain a significant proportion of oil additive may require a very fast initial conversion to generate some solvent in-situ. However, the incorporation of oil into the reaction mixture as described herein allows the oil to act as an additional solvent thus alleviating the requirement for rapid heating/pressurization.

In some embodiments, the reaction mix undergoes a separate pre-heating stage prior to reaching reaction temperature. The pre-heating stage may be performed on a feedstock slurry prior to the full reaction mix being formed. Alternatively the preheating stage may be performed on a slurry comprising all components of the reaction mixture. In some embodiments, the pre-heating stage raises the temperature of the feedstock slurry or reaction mixture to a maximum temperature of about: 120° C., 130° C., 140° C., 150° C., 160° C., 170° C., 180° C., 190° C., or 200° C. In other embodiments, the temperature is raised to less than about: 120° C., 130° C., 140° C., 150° C., 160° C., 170° C., 180° C., 190° C., or 200° C. In still other embodiments the temperature is raised to between about 100° C. and about 200° C., between about 100° C. and about 180° C., between about 100° C. and about 160° C., between about 120° C. and about 180° C., or between about 120° C. and about 160° C.

In continuous flow systems, pressure will generally change from atmospheric to target pressure during the time it takes to cross the pump (i.e. close to instantaneous) whereas in a batch system it may mirror the time that it takes to heat the mixture up.

In some embodiments, the reaction mixture may be brought to a target temperature and/or pressure in a time period of between about 30 seconds and about 30 minutes.

In some embodiments, the reaction mixture may be brought to a target temperature and/or pressure in a time period less than about 15 minutes, less than about 10 minutes, less than about 5 minutes, or less than about 2 minutes.

In certain embodiments, the reaction mixture may be brought to a target pressure substantially instantaneously and brought to a target temperature in less than about 20 minutes, less than about 10 minutes, or less than about 5 minutes. In other embodiments, the reaction mixture may be brought to a target pressure substantially instantaneously and brought to a target temperature in less than about two minutes. In other embodiments, the reaction mixture may be brought to a target pressure substantially instantaneously and brought to a target temperature in between about 1 and about 2 minutes.

Additionally or alternatively, following completion of the retention time period the product mixture generated may be cooled to between about 150° C. and about 200° C., between about 160° C. and about 200° C., preferably between about 170° C. and about 190° C., and more preferably about 180° C., in a time period of less than about 10 minutes, preferably less than about 7 minutes, more preferably less than about 6 minutes, preferably between about 4 and about 6 minutes, and more preferably about 5 minutes. Following the initial cooling period, the temperature may further reduced to ambient temperature with concurrent de-pressurization by fast release into a cool aqueous medium (e.g. cooled water).

The processes of heating/pressurization and cooling/de-pressurization may be facilitated by performing the methods of the present invention in a continuous flow system (see section below entitled "Continuous flow").

Continuous Flow

Bio-product generation from organic matter feedstocks (e.g. lignocellulosic matter and/o coals such as lignite) using the methods of the present invention may be assisted by performing the methods under conditions of continuous flow.

Although the methods need not be performed under conditions of continuous flow, doing so may provide a number of advantageous effects. For example, continuous flow may facilitate the accelerated implementation and/or removal of heat and/or pressure applied to the slurry. This may assist in achieving the desired rates of mass and heat transfer, heating/cooling and/or pressurization/de-pressurization. Continuous flow may also allow the retention time to be tightly controlled. Without limitation to a particular mode of action, it is postulated that the increased speed of heating/cooling and/or pressurization/de-pressurization facilitated by continuous flow conditions along with the capacity to tightly regulate retention time assists in preventing the occurrence of undesirable side-reactions (e.g. polymerization) as the slurry heats/pressurizes and/or cools/de-pressurizes. Continuous flow is also believed to enhance reactions responsible for conversion of organic matter to biofuel by virtue of generating mixing and shear forces believed to aid in emulsification which may be an important mechanism involved in the transport and "storage" of the oils generated away from the reactive surfaces of the feedstock as well as providing interface surface area for so-called 'on-water catalysis'.

Accordingly, in preferred embodiments the methods of the present invention are performed under conditions of continuous flow. As used herein, the term "continuous flow" refers to a process wherein organic matter feedstock mixed with a solvent and pulping liquor in the form of a slurry (which may further comprise any one or more of a solid substrate, an oil additive and/or a catalyst additive) is subjected to:
  (a) heating and pressurization to a target temperature and pressure,
  (b) treatment at target temperature(s) and pressure(s) for a defined time period (i.e. the "retention time"), and
  (c) cooling and de-pressurization,
while the slurry is maintained in a stream of continuous movement along the length (or partial length) of a given surface. It will be understood that "continuous flow" conditions as contemplated herein are defined by a starting point of heating and pressurization (i.e. (a) above) and by an end point of cooling and de-pressurization (i.e. (c) above).

Continuous flow conditions as contemplated herein imply no particular limitation regarding flow velocity of the slurry provided that it is maintained in a stream of continuous movement.

Preferably, the minimum (volume-independent) flow velocity of the slurry along a given surface exceeds the settling velocity of solid matter within the slurry (i.e. the terminal velocity at which a suspended particle having a density greater than the surrounding solution moves (by gravity) towards the bottom of the stream of slurry).

For example, the minimum flow velocity of the slurry may be above about 0.01 cm/s, above about 0.05 cm/s, preferably above about 0.5 cm/s and more preferably above about 1.5 cm/s. The upper flow velocity may be influenced by factors such as the volumetric flow rate and/or retention time. This in turn may be influenced by the components of a particular reactor apparatus utilized to maintain conditions of continuous flow.

Continuous flow conditions may be facilitated, for example, by performing the methods of the invention in a suitable reactor apparatus. A suitable reactor apparatus will generally comprise heating/cooling, pressurizing/de-pressuring and reaction components in which a continuous stream of slurry is maintained.

The use of a suitable flow velocity (under conditions of continuous flow) may be advantageous in preventing scale-formation along the length of a particular surface that the slurry moves along (e.g. vessel walls of a reactor apparatus) and/or generating an effective mixing regime for efficient heat transfer into and within the slurry.

Bio-Products

The methods disclosed herein may be used to produce bio-product(s) from organic matter feedstocks (e.g. ligno-cellulosic matter and/or coals such as lignite). The nature of the bio-product(s) may depend on a variety of different factors including, for example, the organic matter feedstock treated, and/or the reaction conditions/reagents utilized in the methods.

In certain embodiments, the bio-product(s) may comprise one or more biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

In general, bio-product(s) produced in accordance with the methods of the present invention comprise or consist of a bio-oil. The bio-oil may comprise compounds including, but not limited to, any one or more of alkanes, alkenes, aldehydes, carboxylic acids, carbohydrates, phenols, furfurals, alcohols, and ketones. The bio-oil may comprise compounds including but not limited to aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

The bio-oil may comprise multiple phases, including but not limited to a water-soluble aqueous phase which may comprise, compounds including, but not limited to, any one or more of carbohydrates, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives; and a water-insoluble phase which may comprise, compounds including, but not limited to, any one or more of waxes, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

Other non-limiting examples of the bio-products include oil char (e.g. carbon char with bound oils), char, and gaseous product (e.g. methane, hydrogen, carbon monoxide and/or carbon dioxide, ethane, ethene, propene, propane).

In some embodiments, a biofuel may be produced from organic matter comprising lignocellulosic matter. The biofuel may comprise a liquid phase comprising bio-oil.

Biofuels (e.g. bio-oils) produced in accordance with the methods of the invention may comprise a number of advantageous features, non-limiting examples of which include reduced oxygen content, increased hydrogen content, increased energy content and increased stability. In addition, bio-oils produced by the methods of the invention may comprise a single oil phase containing the liquefaction product. The product may be separated from the oil phase using, for example, centrifugation eliminating the need to evaporate large amounts of water.

A bio-oil bio-product produced in accordance with the methods of the invention may comprise an energy content of greater than about 25 MJ/kg, greater than about 30 MJ/kg, more preferably greater than about 32 MJ/kg, more preferably greater than about 35 MJ/kg, still more preferably greater than about 37 MJ/kg, 38 MJ/kg or 39 MJ/kg, and most preferably above about 41 MJ/kg. The bio-oil product may comprise less than about 20% oxygen, preferably less than about 15% wt db oxygen, more preferably less than about 10% wt db oxygen, still more preferably less than about 8% wt db oxygen, still more preferably less than about 7% wt db oxygen, and most preferably less than about 5% wt db oxygen. The bio-oil product may comprise greater than about 6% wt db hydrogen, preferably greater than about 7% wt db hydrogen, more preferably greater than about 8% wt db hydrogen, and still more preferably greater than about 9% wt db hydrogen. The molar hydrogen:carbon ratio of a bio-oil of the invention may be less than about 1.5, less than about 1.4, less than about 1.3, less than about 1.2, or about 1.0.

A bio-oil produced in accordance with the methods of the invention may comprise, for example, any one or more of the following classes of compounds: phenols, aromatic and aliphatic acids, ketones, aldehydes, hydrocarbons, alcohols, esters, ethers, furans, furfurals, terpenes, polycyclics, oligo- and polymers of each of the aforementioned classes, plant sterols, modified plant sterols, asphaltenes, pre-asphaltenes, and waxes.

A char or oil char bio-product produced in accordance with the methods of the invention may comprise an energy content of greater than about 20 MJ/kg, preferably greater than about 25 MJ/kg, more preferably greater than about 30 MJ/kg, and still more preferably greater than about 31 MJ/kg, 32 MJ/kg, 33 MJ/kg or 34 MJ/kg. The char or oil char product may comprise less than about 20% wt db oxygen, preferably less than about 15% wt db oxygen, more preferably less than about 10% wt db oxygen and still more preferably less than about 9% wt db oxygen. The char or oil char product may comprise greater than about 2% wt db hydrogen, preferably greater than about 3% wt db hydrogen, more preferably greater than about 4% wt db hydrogen, and still more preferably greater than about 5% wt db hydrogen. The molar hydrogen:carbon ratio of a char or oil char product of the invention may be less than about 1.0, less than about 0.9, less than about 0.8, less than about 0.7, or less than about 0.6.

An oil char bio-product produced in accordance with the methods of the invention may comprise, for example, any one or more of the following classes of compounds: phenols, aromatic and aliphatic acids, ketones, aldehydes, hydrocarbons, alcohols, esters, ethers, furans, furfurals, terpenes, polycyclics, oligo- and polymers of each of the aforementioned classes, asphaltenes, pre-asphaltenes, and waxes.

A char bio-product (upgraded PCI equivalent coal) produced in accordance with the methods of the invention may comprise, for example, a mixture of amorphous and graphitic carbon with end groups partially oxygenated, giving rise to surface carboxy- and alkoxy groups as well as carbonyl and esters.

Bio-products produced in accordance with the methods of the present invention may comprise one or more biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

Bio-products produced in accordance with the methods of the present invention may be cleaned and/or separated into individual components using standard techniques known in the art.

For example, solid and liquid phases of biofuel products (e.g. from the conversion of coal) may be filtered through a pressure filter press, or rotary vacuum drum filter in a first stage of solid and liquid separation. The solid product obtained may include a high carbon char with bound oils. In certain embodiments, the oil may be separated from the char, for example, by thermal distillation or by solvent extraction. The liquid product obtained may contain a low percentage of light oils, which may be concentrated and recovered though an evaporator.

Bio-products produced in accordance with the methods of the present invention may be used in any number of applications. For example, biofuels may be blended with other fuels, including for example, ethanol, diesel and the like. Additionally or alternatively, the biofuels may be upgraded into higher fuel products. Additionally or alternatively, the biofuels may be used directly, for example, as petroleum products and the like.

Figure 2A:
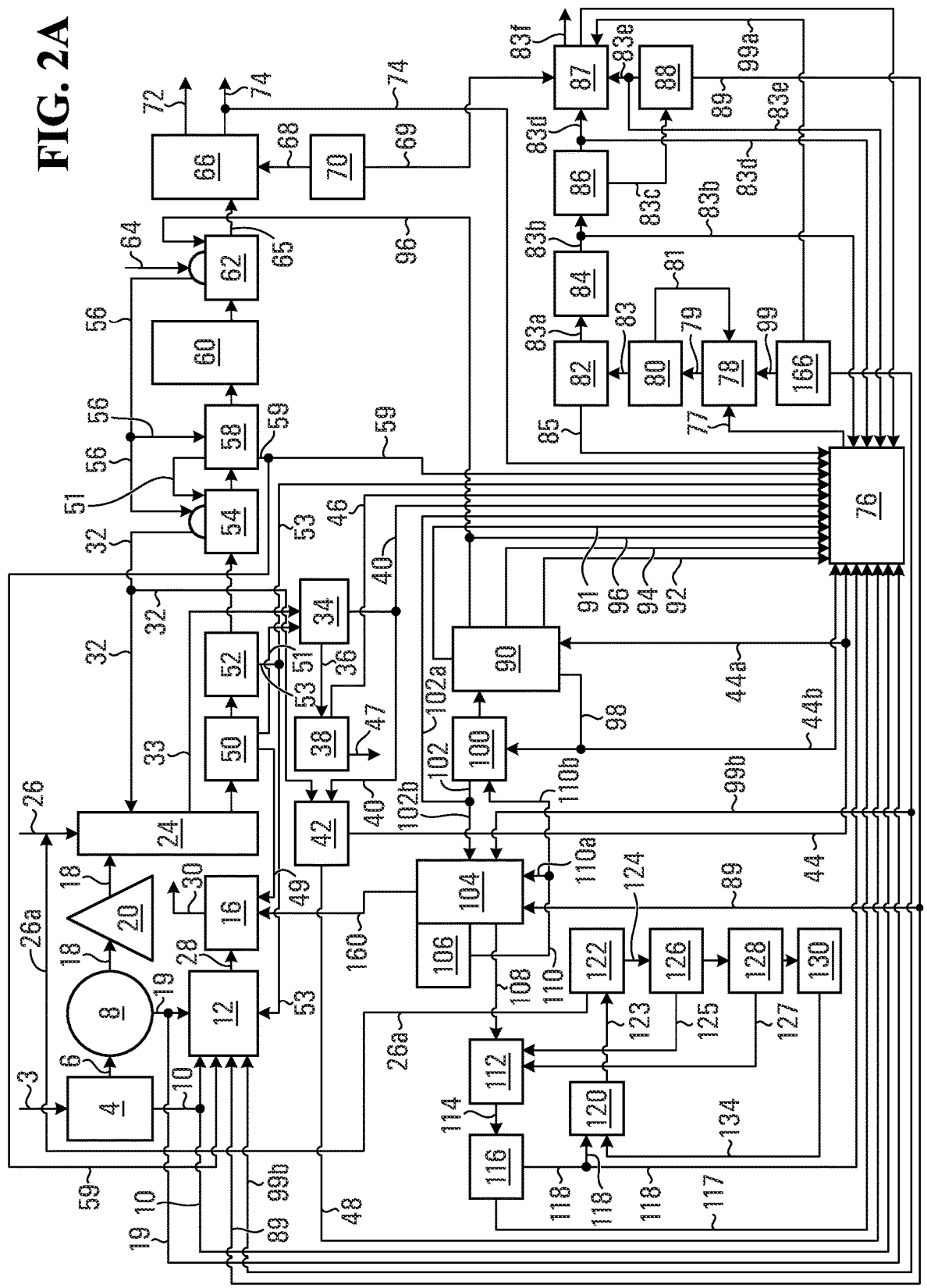
FIG. 2A is a schematic drawing of an integrated pulp mill and thermochemical conversion system according to an embodiment of the invention.

Referring to FIG. 2A, an integrated pulp mill and thermochemical conversion system according to one embodiment of the invention is shown generally at 1. System 1 may be considered as a combination of several subsystems, including a wood handling subsystem, digester subsystem, a bleach plant subsystem, a chemical recovery subsystem, a thermochemical conversion subsystem, and a waste water treatment subsystem.

The digester subsystem is responsible for the chemical digestion of lignocellulosic materials with caustic white liquor under pressure and temperature to produce wood pulp consisting of almost pure cellulose fibres. The combined liquids following digestion, known as black liquor, contain lignin fragments, carbohydrates from the breakdown of cellulose and hemicelluloses, extractives including hydrolyzed resin and fatty acids, sodium sulphate, and other inorganic materials. For the purposes of this disclosure, subsequent washing steps and equipment therefor are considered to form part of the digester subsystem.

Pulp generated in the digester subsystem is conveyed to the bleach plant subsystem where further chemical processing with chlorine dioxide, sodium hydroxide and peroxide is carried out on pulp to remove the residual lignin and chromophores to increase its brightness. Effluent from the bleach plant may be conveyed to a waste water treatment subsystem. As the bleach plant effluent is a source of organic matter, it may be desirable to convey bleach plant effluent to a thermochemical conversion subsystem as described further below. However, the presence of corrosive chlorides in the bleach plant effluent makes this unlikely.

Black liquor from the digester subsystem is conveyed to the chemical recovery subsystem in which condensates are recovered from the black liquor, black liquor is burned to generate high pressure steam for use elsewhere in the mill, and white liquor is regenerated for reintroduction into the digester for further pulping.

Pulping liquors from the digester subsystem or chemical recovery subsystem can also be conveyed to the thermochemical conversion subsystem for use in the production of bio-products. The thermochemical conversion system may also receive effluent from the bleach plant subsystem. Condensates and steam produced by the thermochemical conversion system can also be redirected to any of the aforementioned subsystems.

Digester Subsystem

Referring again to FIG. 2, lignocellulosic material is introduced to the system 1 as, for example, wood 3. Wood 3 is conveyed to a de-barker 4 where it is debarked. Debarked wood 6 is conveyed to a wood chipper 8, whereas bark 10 is conveyed to a hog fuel boiler 12. A portion of bark 10 may also be conveyed to mixing tank 76 of the thermochemical conversion subsystem. Wood chips 18 produced by wood chipper 8 may be conveyed to a chip bin 20, whereas chipping fines 19 are conveyed to hog fuel boiler 12. Hog fuel boiler 12 generates high pressure steam 28 which is fed to turbines, e.g. turbine 16, to reduce the steam pressure for use elsewhere in the mill and/or the thermochemical conversion subsystem, and also generate electricity for use elsewhere in the mill and/or the thermochemical conversion subsystem. For example, this, steam may be directed to the digesters, the evaporators and concentrators, pulp dryers and paper machine dryer sections, and/or thermochemical conversion subsystem for heating as may be required.

From chip bin 20, wood chips 18 may be conveyed to kraft digester 24 where they are mixed with caustic white liquor 26 and cooked at high temperature and pressure (using, for example, steam originating from turbine 16) to produce delignified pulp and black liquors. Hot, pressurized black liquors 33 are removed from digester 24 and conveyed to a flash tank 34. Cooked pulp, on the other hand, is conveyed to a blow tank 50 where the pressure is reduced to atmospheric pressure to release steam and volatiles. Volatiles 51 from the blow tank 50 are condensed and conveyed to a turpentine decanter 38.

The mixture of depressurized black liquors 33 are flashed to atmospheric pressure in flash tank 34, releasing steam, entrained Total-Reduced Sulfur compounds (TRS), methanol, and turpentine. The volatiles pass through a condenser and are then conveyed to turpentine decanter 38, where turpentine 46 may be recovered as overflow and foul condensates 47 may be recovered as underflow. Turpentine 46 may be transported offsite, or used as fuel within the pulp mill. Alternatively, turpentine 46 may be conveyed to mixing tank 76 to be used as an organic matter feedstock for thermochemical conversion to a bio-product.

Foul condensates 47 are conveyed to a stripper to remove TRS, which are typically burned within the mill. The resulting aqueous stream typically includes organics such as methanol, and thus could be directed from the stripper to mixing tank 76 as a source of water and organic matter. Alternatively, a portion of the foul condensates 47 themselves could be conveyed to mixing tank 76 as a source of water and organic matter. One advantage of using foul condensates themselves in the thermochemical conversion subsystem is that it may reduce the amount of TRS generated in the pulp mill that must be processed, and thus free capacity to treat the significant amounts of TRS that are produced in the thermochemical conversion subsystem.

Weak black liquor 40 is recovered from the flash tank 34 and conveyed to weak black liquor storage tank 42. Alternatively, weak black liquor 40 may be conveyed to mixing tank 76. Conveying at least a portion of the weak black liquor directly to the thermochemical conversion subsystem rather than to evaporator will reduce the load on the chemical recovery subsystem of the pulp mill and may thereby increase the amount of wood chips 18 that can be pulped in digester 24. For every 1% of black liquor solids diverted from the chemical recovery subsystem, as much as one extra tonne of fully bleached pulp may be manufacture per day. In the weak black liquor storage tank 42, tall oil soap 48 may be skimmed from the weak black liquor 40 and processed to tall oil and/or conveyed to mixing tank 76. Alternatively, tall oil soap 48 may skimmed from weak black liquor storage and conveyed directly to mixing tank 76. Conveying skimmed tall oil soap directly from weak black liquor storage to mixing tank 76 would reduce the cost of processing the tall oil soap to tall oil for shipment.

The cooked pulp recovered from the digester, also referred to as brown stock pulp, is conveyed from blow tank 50 to knotter 52 where undigested knots 53 are screened from the brown stock pulp and conveyed to hog fuel boiler 12. Alternatively, knots 53 may be conveyed to mixing tank 76 of the thermochemical conversion subsystem for use as an organic matter feedstock.

The de-knotted brown stock pulp is conveyed from knotter 52 to brown stock washers 54 where residual black liquor is separated from cellulose fibre by washing with water. A person skilled in the art will understand that a pulp mill will typically have several brown stock washers arranged in series, with wash water moving countercurrent to the direction that the pulp is moving through the washers. A portion of the brown stock washer filtrate 32, which includes a mixture of wash water and black liquors removed from the brown stock pulp, is typically conveyed from through brown stock washers 54 to the digester 24 for mixing with the cooking liquors, washing the pulp, and removal of black liquor at high temperature and pressure. Alternatively, the other portion or all of the brown stock washer filtrate 32 may be directed to the weak black liquor storage tank 42, and/or to the thermochemical conversion subsystem (e.g. mixing tank 76).

From brown stock washers 54, brown stock pulp is conveyed to screen room 58 where shives, fines, dirt and other debris may be removed (collectively, "fines 59) and conveyed to hog fuel boiler 12 or mixing tank 76. Screened brown stock pulp is then conveyed to oxygen delignification 60 to remove residual lignin. The oxygen-delignified pulp is then conveyed to post-oxygen washers 62 for further washing. A person skilled in the art will again understand that multiple post-oxygen washers may be arranged in series with wash water moving countercurrent to the direction that the pulp is moving through the washers. Wash water 64 is typically introduced to the digester subsystem at post-oxygen washers 62. Brown stock wash water 56 is conveyed from post-oxygen washers 62 to brown stock washers 54. A portion of brown stock wash water 56 may also be conveyed to screen room 58 before being re-directed to brown stock washers 54. Alternatively, brown stock wash water 56 may be conveyed to mixing tank 76 of the thermochemical conversion subsystem.

Bleach Plant Subsystem

From the screen room 58 or the post-oxygen washers 62, screened brown stock or oxygen-delignified pulp 65 is conveyed to bleach plant 66 for further delignification and brightening. Bleaching agents including chlorine dioxide, ozone, peroxide and further caustic are provided to bleach plant 66 for bleaching of the brown or oxygen-delignified pulp 65. For example, chlorine dioxide 68 may be produced by a sodium chlorate plant 70 and conveyed to bleaching plant 66. Hydrogen 69 produced as a by-product of the sodium chlorate production process may be conveyed from sodium chlorate plant 70 to hydrotreater 87 of the thermochemical conversion subsystem for use in cracking bioproduct.

Pulp exits the bleach plant as bleached market pulp 72. Bleach plant effluent 74, which includes caustics, organic molecules, and chloride, may be forwarded to the waste water treatment subsystem.

Chemical Recovery Subsystem

From weak black liquor storage tank 42, weak black liquor 44 may be conveyed to the thermochemical conversion subsystem (e.g. mixing tank 76) for use as a source of catalyst and/or organic matter. Otherwise, weak black liquor 44 is conveyed to multiple effect evaporators 90 where it is concentrated. During this concentration process, the partially concentrated black liquor (at a solids concentration between 25 and 40%) is directed to an evaporator skim tank where tall oil soap 91 rises to the surface of the liquor where it is skimmed and then processed to tall oil and/or conveyed to mixing tank 76. Again, conveying skimmed tall oil soap directly from evaporators 90 to mixing tank 76 would reduce the cost of processing the tall oil soap to tall oil for shipment. A portion of the partially concentrated, skimmed black liquor may also be conveyed to mixing tank 76 for use as a catalyst and organic matter.

From evaporators 90, strong black liquor 98 is conveyed to concentrator 100 where the black liquor is further concentrated to heavy black liquor 102 that is conveyed to recovery boiler 104. A portion of strong black liquor 98 may also be conveyed to mixing tank 76 for use as a source of catalysts and organic matter. Similarly, a portion of heavy black liquor 102 may be conveyed to mixing tank 76.

Multiple effect evaporators 90 also produce several condensate streams including clean condensates 92, foul condensates 94, and combined condensates 96. Clean condensates 92 are typically conveyed to polishers or to post-oxygen washers 62, or to cool other streams (and thereby become heated). Combined condensates 96 may be conveyed to post-oxygen washers 62. Foul condensates 94 may be conveyed to a stripper before re-use and/or sewered. However, any of the condensates streams 92, 94 and 96 may be conveyed to mixing tank 76.

In an exemplary system of multiple effect evaporators, weak black liquor (e.g. at 19% solids by weight at 91° C.) may be received in the evaporators at a rate of 1,215 kg solids per minute. For heating, steam (e.g. 550 kPa at 156° C.) may be received by the evaporators at a rate of 75,100 kg/h. Stripper steam (e.g. 550 kPa at 156° C.) may be received by the evaporators at a rate of 4,100 kg/h. Cooling water (e.g. at 15° C.) for the condensers may be received by the evaporators at a rate of 27,000 kg/min). In total, the evaporators may process 1750 tonnes (3.85 million pounds) of black liquor solids per day. As outputs, the evaporators may produce strong black liquor (e.g. at 19% solids by weight at 91° C.) at a rate of 1,215 kg solids per minute. Clean condensates (e.g. at 143° C.) may be produced at about 1,250 kg/min for conveyance to, for example, polishing. Foul condensates (e.g. at 79° C.) may be produced at about 1,875 kg/min for conveyance to, for example, polishing. Combined condensates (e.g. at 83° C.) may be produced at about 2,670 kg/min for conveyance to brown stock washers (e.g. 2,120 kg/min) or sewers (e.g. 520 kg/min). Warmed water from the condensers (e.g. $37^2$C) may be produced at about 27,000 kg/min and conveyed to a warm water tank.

The portion of heavy black liquor 102 that is conveyed to recovery boiler 104 is burned to recover inorganic chemicals for reuse in the pulping process. The higher concentration of solids in the heavy black liquor 102 (between about 65% and 80% solids by weight) increases the energy and chemical efficiency of the recovery cycle. Smelt 108 produced in the recovery boiler is conveyed to dissolving tank 112 where it is dissolved in a process water known as "weak wash" to produce "green liquor".

Recovery boiler 104 also generates high pressure steam may be fed to turbine 16. Fly ash 110 may be conveyed from precipitator 106 back to recovery boiler 104 to increase sodium and sulfur recovery. Alternatively, fly ash may be conveyed to concentrator 100 for mixing with strong black liquor 98, and/or to the thermochemical conversion subsystem for use as a source of organic matter.

Green liquor 114 is conveyed from dissolving tank 112 to green liquor clarifier 116. Clarified green liquor 118 is generally conveyed to the causticizers 120 where it is mixed with calcium oxide (i.e. lime) to produce white liquor. White liquor 123 is then conveyed to white liquor clarifier 122. Clarified white liquor 26a is conveyed to digester 24 for use in pulping. Alternatively, white liquor 26a may be conveyed to mixing tank 76 for use as a source of catalyst.

Residual lime mud 124 is conveyed from white liquor clarifier 122 to lime mud washer 126, which may typically be a clarifier. Washed lime mud is conveyed to a lime mud precoat (LMPC) filter 128 whereas weak wash 125 is conveyed from lime mud washer 126 to dissolving tank 112 for mixing with smelt 108. Lime cake is then conveyed from LMPC filter 128 to lime kiln 130, whereas weak wash 127 is conveyed from LMPC filter 128 to dissolving tank 112. Lime mud is burnt in the lime kiln 130 to produce reburnt lime 134, which is conveyed to the causticizers 120 for recausticizing green liquor 118 to white liquor 26a.

Thermochemical Conversion Subsystem

Referring now to the thermochemical conversion subsystem, an organic matter feedstock may be received with water and a source of catalyst in mixing tank 76 to produce a reaction mixture.

The organic matter feedstock may include one or more of weak black liquor 44, strong black liquor 98, heavy black liquor 102, tall oil soap 91, tall oil, foul condensates 92, clean condensates 96, combined condensates 94, bleach plant effluent 74, brown stock washer filtrate 32, bark 10, knots 53, fines 59, wood chips 18, hog fuel 19, sawdust, and ground wood meal. Larger lignocellulosic materials such as knots, wood chips, bark, hog fuel, fines and other screening rejects may need to be comminuted prior to introduction to mixing tank 76. A general guideline is that up to an including 6 mm diameter particles currently may provide the optimum maximum size for commercial Cat-HTR applications. However, particles with larger dimensions (e.g. up to the sizes of typical wood chips) may be used, provided that the reaction mixture can be pumped as a slurry. Further organic matter pre-treatment steps such as low temperature (soft) hydrothermal pre-treatment can increase the amount of solids that can be pumped as slurries.

The catalyst may be provided from one or more sources of pulping liquors in the pulp mill, including weak black liquor 44, white liquor 26a, green liquor 118, strong black liquor 98, heavy black liquor 102, tall oil soap 91, tall oil, brownstock wash filtrate 32, brownstock wash water 56, and purchased caustic soda.

The water may be provided by one or more of mill water, weak black liquor 44, white liquor 26a, green liquor 118, strong black liquor 98, heavy black liquor 102, tall oil soap 91, tall oil, foul condensates 92, clean condensates 96, combined condensates 94, brown stock wash filtrate 32, stripper condensates, and digester condensates. Bleach plant effluent 74 may also be a possible source of water depending on the chlorine and chloride content.

The components of the reaction mixture may be batched into mixing tank 76 by conventional bulk solids handling techniques (e.g. load cells to monitor mass of bulker bags containing biomass). To evaluate the amount of solvent or water to be added to give a pumpable reaction mixture consistency, the water content of the lignocellulose (e.g. hog fuel, chips, knots, and fines) can be determined by periodic off-line sampling or possibly by online means.

Figure 2B:
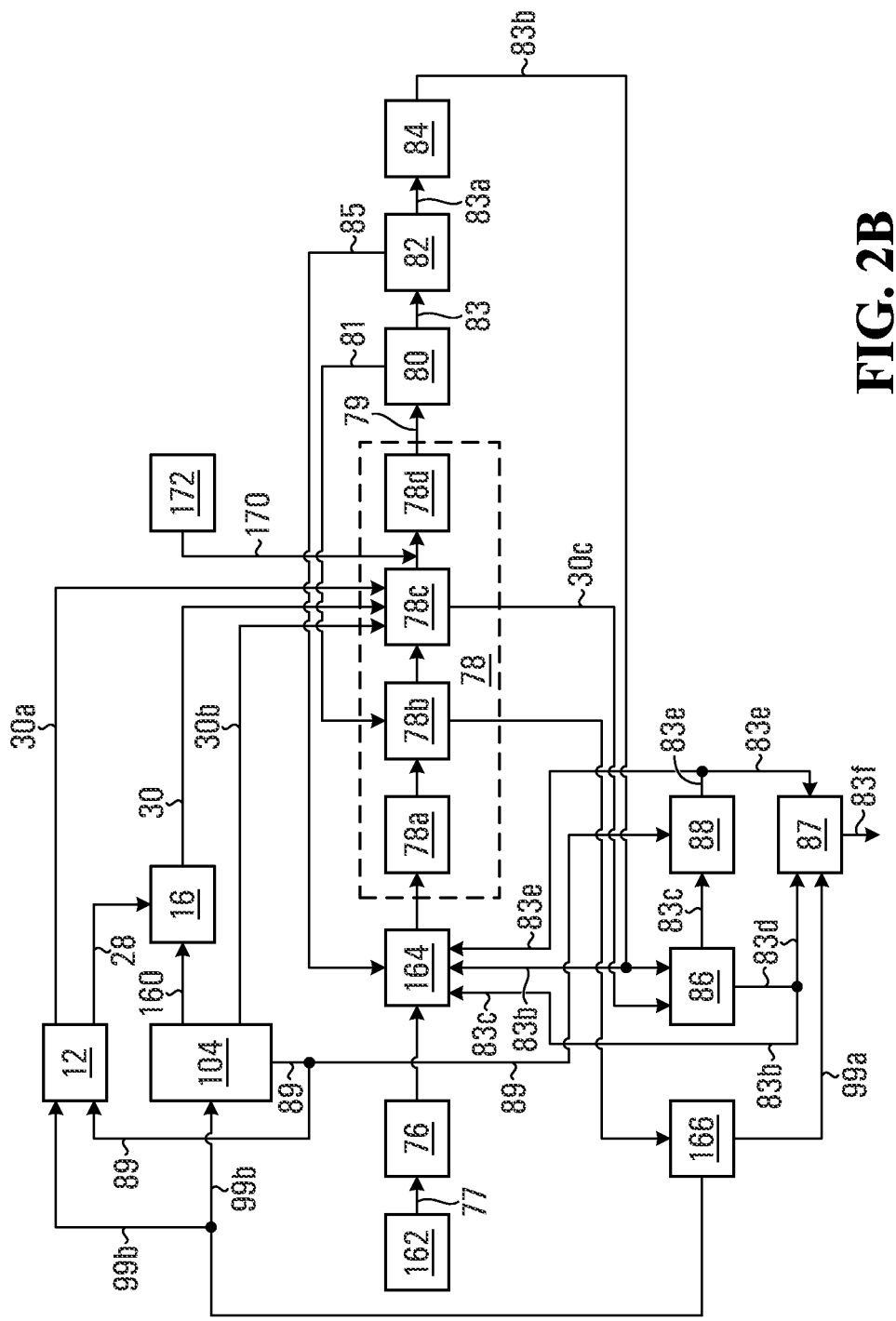
FIG. 2B is a schematic diagram showing a thermochemical conversion subsystem of the system illustrated in FIG. 2A.

Alternatively, referring to FIG. 2B, components of the reaction mixture other than the pulping liquors may be pre-mixed in a pre-mixing tank 162 and conveyed on demand to a mixing tank 76 to be combined with pulping liquors.

Reaction mixture 77 is conveyed to reactor vessel 78 where it is pre-heated and then treated at a reaction temperature and pressure suitable for conversion of all or a portion of the organic matter in the reaction mixture to a product mixture comprising a bio-product and water. Referring to FIG. 2B, reaction mixture 77 may be conveyed to a feed tank 164 prior to being conveyed to reactor vessel 78 itself. In feed tank 164, the reaction mixture may be supplemented with separated water and condensates bio oils produced in the thermochemical conversion process and recycled to the feed tank 164.

Referring still to FIG. 2B, reaction mixture 77 introduced into reactor vessel 78 may initially be pressurized in pressurization module 78a to a pressure from about 150 to about 300 Bar, perhaps from about 150 to about 300 Bar, or from about 180 to about 250 Bar. The pressurized reaction mixture may then be conveyed to pre-heater 50b where it is pre-heated to a temperature of about 150 to about 250° C.

The reaction mixture is then conveyed through a heat exchanger 50c operating off steam conveyed directly from hog fuel boiler 12, recovery boiler 104, or steam 30 from turbine 16, by which it is heated to a final reaction temperature of about 250 to about 400° C., or of about 280 to about 350° C., or of about 300 to about 350° C., or of about 280 to about 320° C. Alternatively, supercritical steam may be injected directly into the reaction mixture immediately before the reactor vessel in order to bring to bring the reaction mixture to a final reaction temperature. This would require the supercritical steam to be at a higher pressure than the reaction mixture and may require a supercritical boiler unit.

In FIG. 2A, the black liquor is added to the reaction mixture in mixing tank 76. However, homogeneous catalyst (for which the kraft liquor inorganic components partly or wholly substitute) is preferably added after the reaction mixture has been raised to reaction temperature and pressure. A dosing pump may be used to inject caustic solution after supercritical steam is added to the reaction mixture. Accordingly, referring to FIG. 2B, pulping liquors (including weak black liquor 44, white liquor 26a, green liquor 118, strong black liquor 98, heavy black liquor 102, tall oil soap 91, tall oil, brownstock wash filtrate 32, brownstock wash water 56, and purchased caustic soda, or any combination thereof, collectively identified as pulping liquors 170) could also be conveyed into the reaction mixture immediately prior to entering reactor vessels 78d, e.g. by injection using a dosing pump 172. This may provide the advantage that the mixing tanks need not come into contact with the corrosive caustic liquors and can be made of cheaper materials. The feed flows may be held constant and fluctuations in the liquor flows compensated for by adding fresh caustic from a secondary tank source. Alternatively, the reaction mixture flow could be varied to compensate for variations in liquor flows.

The flow of organic matter in the reaction mixture and other liquids can be measured by means of mass flow sensors/controllers known to the industry (e.g. Coriolis mass flow sensors for biomass slurries), which provide the effective density of a slurry from which a solids loading can be predicted.

After a period of retention in the reactor vessels 78d, e.g. about 20 to about 30 minutes, product mixture 79 produced in the reactor 78 is then conveyed to depressurizer 80. Foul steam 81 from depressurizer 80 may be conveyed to reactor 78, e.g. pre-heater 50b for use in preheating reaction mixture 77 received in the reactor. Foul steam 81 may be at a pressure of about 5 to about 50 Bar, and preferably about 15 to about 35 Bar. In a particular embodiment, steam 81 will be about 20 Bar at about 212° C. Foul steam 81 also contains non-condensable gases. A mixture of light oils and other chemicals, water, and non-condensable gases 99 may be conveyed to a separator 166. Light oils 99a from separator 166 may be conveyed to hydrotreater 87, whereas non-condensable gases 99b and other vapors may be returned to the pulp mill for burning in a recovery boiler 104, hog fuel boiler 12, or an additional incinerator.

A bio-product and condensates mixture 83 is conveyed from depressurizer 80 to separator 82. Water and condensates 85 may be separated from bio-products and conveyed back to mixing tank 76 as a source of water, whereas combined bio-products 83a and 83b may be conveyed to evaporator 84 and then to distiller 86, respectively. A portion of combined bio-product 83b may be returned to mixing tank 76, or feed tank 164 as depicted in FIG. 2B, for combining into the reaction mixture. Combined bio-produces 83b received in distiller 86 are separated by distillation into a heavy biooil fraction 83c and a distilled biooils fraction 83d. The distiller 86 may be heated by waste steam 30c from heat exchanger 78c. Heavy biooil fraction 83c is conveyed to coker 88.

Water and condensates 85 contain, among other components, dissolved organics such as alkyl phenols and alkyl catechols, ketones, alcohols, especially methanol and ethanol, and, organosulphur compounds. This water, as well as foul condensates 81, also contains inorganic compounds primarily salts of sodium with sulphur containing anions of poorly-defined oxidation state, and carboxylates of carbonic, formic, succinic, methylsuccinic, acetic, glycolic, and lactic acid. The water cannot be recycled infinitely within the thermochemical conversion subsystem because the inorganic components will accumulate and catalytic activity will be decreased. Also, incoming biomass contains water and therefore there is a net influx of water. Therefore the water must be discharged from the thermochemical conversion subsystem.

Water may be conveyed from the thermochemical conversion subsystem to the pulp mill for recovery inorganic components for the pulping process as well has organics for the production of heat in the recovery boiler. Water may be conveyed to the pulp mill after prior biological treatment of organics, adsorption of organics and recovery for addition to the biocrude product stream, or adsorption of organics followed by processing the adsorbate (e.g. cellulose cartridge filters) in the reactor vessel.

To minimize the water treatment necessary, it is desirable to have only the minimum amount of water in the reactor to enable hydrothermal reactions to occur. One option is to use oil as additional reaction mixture component medium. The oil can be recycled oil, and potential oil recycle paths are shown in FIG. 2B, but it can also be oil from other sources, such as tall oil, or even vegetable oils.

Referring again to FIGS. 2A and 2B distilled biooils fraction 83d may be conveyed from distiller 86 to hydrotreater 87 for cracking to produce hydrocarbon liquids 83f. A portion of distilled biooils fraction 83d may be returned to mixing tank 76, or feed tank 164 as depicted in FIG. 2B, for combining into the reaction mixture. Heavy bio oils fraction 83c may be conveyed from distiller 86 to coker 88. Bio-products 83e from coker 88 may be conveyed to hydrotreater 87, whereas biocoke 89 from coker 88 may be conveyed to hog fuel boiler 12 or recovery boiler 104. A portion of bio-products 83e may be returned to mixing tank 76, or feed tank 164 as depicted in FIG. 2B, for combining into the reaction mixture.

EXAMPLES

The invention will now be described with reference to specific examples, which should not be construed as in any way limiting.

In the following Examples, the thermochemical conversion process utilized is also referred to as "Cat-HTR".

Example 1: Materials and Methods

Australian Radiata pine was run with black liquor to establish the catalytic action of black liquor and suitable operating temperatures. In the same manner, hog fuel trials were run alternately using sodium hydroxide and then with black liquor. Finally, mixed feedstocks containing hog fuel, SPF wood chip, and paper sludge were processed with black liquor.

Pre-processing trials were conducted on the feedstocks to prepare them to specifications of the small pilot plant (SPP). Dry-milling of the feedstocks followed by Cat-HTR processing in the small pilot plant led to successful production of bio-crude (bio-oil) from the feedstocks, in particular from a mixture of hog fuel, SPF wood chip, sludge and black liquor.

The resulting bio-crudes had gross calorific values (GCV) on a dry ash free basis in the range of 33-36 MJ/kg. For comparison, diesel fuel has a GCV (or energy content) of about 45 MJ/kg and unprocessed dry wood about 18-21 MJ/kg. Licella has demonstrated that distilled bio-crudes from Radiata pine wood flour with initial energy contents in this range can be successfully hydroprocessed to give hydrocarbons compatible with refinery streams at an advanced stage of processing to finished fuels. It was confirmed in the trials that the alkaline inorganic components of black liquor are capable of substituting for the alkaline catalysts typically used by Licella in order to produce high energy density bio-crudes. That is, as well as supplying liquid phase biomass to the reactors, the black liquor can obviate the need to add additional alkaline catalysts in the Cat-HTR process. The highest proportion of black liquor used in testing was approximately 1 part of dry wood feedstock to 0.65 parts of black liquor (analysis as per table 4). The highest level of black liquor used was determined in this instance by the level of sulphur compatible with the materials of construction of the SPP and the expected levels of hydrogen sulphide in the producer gas, consistent with safe operation of the plant.

Summary of Feedstock Trials

Feedstock Preparation

Feedstocks utilized were: SPF wood chip (spruce-fir-pine wood chip); hog fuel (wood residue including wood chips, bark, and the like); paper sludge; and black liquor Approximately 100 kg on a dry basis of each solid feedstock was obtained. Most types of feedstock required some degree of preparation before processing. Solid materials are processed in as slurries in water or other solvents, and the particle size of the solid materials is of a size suitable for producing a slurry that can be pumped at high pressure. The small pilot plant (SPP), due to its small pump valve orifices, requires a greater degree of comminution of the feedstock than would a commercial facility. For the SPP, specifically, it is preferred to reduce to the maximum particle size to about 150 microns diameter. Both wet and dry grinding have been utilized, and dry grinding has usually been employed for the smaller particle sized required for the SPP.

Solid Feedstock Preparation

Subsequent to the wet-grinding activities, dry grinding of the wood chip, hog fuel and sludge feedstocks was carried out by a contracted firm Aximill, using modified compressed air jet mills, reference http://www.aximill.com. The feedstock is supplied at approximately 10% moisture (however all feedstock mass within this report is quoted on a dry basis). The particle size is reduced to sub 130 micron, typical particle size distribution data is available upon request (however this feedstock is peculiar to the requirements of the SPP and unlikely to be of interests in subsequent large scale testing). The tested feedstock analysis is presented below, including proximate, ultimate, and ash constituent analyses in the feedstock analysis section of this document.

Black Liquor Preparation for Cat-HTR

As received black liquor (per Table 4) was diluted 100% with water by volume. The diluted mixture was filtered through a 250 micron sieve to remove oversize particles and contaminants such as plastic and wood chips etc to be compliant with pump specifications on the small pilot plant. The amount of material removed was a negligible fraction of the overall sample. The filtered, diluted black liquor was then used as a stock liquor for addition at various levels to other feedstocks for Cat-HTR. This stock liquor is referred to as 'stock black liquor'.

Run Summary

A detailed description of individual runs is provided in Example 2. Table 3 below gives a summary of all experiments conducted during the course of this study, irrespective of outcome.

TABLE 2

Properties of Stock Black Liquor

| The properties of this stock black liquor are | 1.14 | SG of stock black liquor (diluted mixture) kg/L |
|---|---|---|
| 1 kg Stock Black Liquor Contains: | 0.439 | L of black liquor (per Table 4) |
| 1 kg Stock Black Liquor Contains: | 0.561 | kg of black liquor (per Table 4) |

TABLE 3

Summary run conditions

| Run ID No. | Feedstock | Liquid Catalyst | Summary | Outcome |
|---|---|---|---|---|
| 20140521 | 8% Licella radiata pine *note1 | 1 kg stock black liquor per dry kg wood | Successful trial on dry ground radiata pine and black liquor | Successful |
| 20140523 | 8% Licella radiata pine *note1 | 1.3 kg stock black liquor per dry kg wood | Successful trial on dry ground radiata pine and a higher concentration of black liquor | Successful |
| 20140716 | 7.8% hog fuel | 12% sodium hydroxide | Successful trial on dry ground hog fuel slurry. | Successful |
| 20140724 | 8% hog fuel | 1.3 kg stock black liquor per dry kg wood | Successful trial on dry ground hog fuel slurry. | Successful |
| 20140731 | 6.4% hog fuel, 1.44% wood, 0.16% sludge | 1.3 kg stock black liquor per dry kg mix | Successful trial on dry ground mixed component slurry. | Successful |
| 20140814 | 6.4% hog fuel, 1.44% wood, 0.16% sludge | 1.3 kg stock black liquor per dry kg mix | Successful trial on dry ground mixed component slurry. | Successful |

Chemical Analysis

Proximate Analysis Methods for Bio-Crude and Feedstocks.

Weigh and heat a sample in a crucible at 900° C., volatile matter and fixed carbon are determined according to AS2434.2. Volatile matter and fixed carbon are stated for feedstocks only.

Solid feedstock and oil product ash yield is performed according to HRL method 1.6. The sample is held at 815° C. in an open crucible until the weight is stable.

The results of a proximate analysis are ash content, volatile mater and fixed carbon which are determined as percentages of the sample mass, on dry basis. Results allow for an estimate of the "reactivity" of feedstocks, and amount of "solids" expected.

Ultimate Analysis

Ultimate analysis is performed by HRL method 1.4 sample in a CHN analyser.

Ultimate analysis is a breakdown of the sample in its most important elements—carbon, hydrogen, nitrogen, sulphur and oxygen. The oxygen content is a key indicator as it is inversely correlated to the energy content of the sample. The Cat-HTR process can be operated in a way to retain or to remove oxygen according to the operating conditions. Depending on the target chemical fractions or purpose of the bio-crude, the remaining oxygen may be reduced at the refinery stage by hydrogenation to obtain the highest energy density; or the oxygen is maintained within the bio-crude as an oxygenated chemical feedstock containing phenols (for resins and plasticisers and chemical precursors of pharmaceuticals). The hydrogen and the carbon are the main contributors to the energy content of the bio-crude. Sulphur is of interest for materials selection on the Cat-HTR plant, it is a factor that influences capital cost of Cat-HTR plant. Sulphur in the bio-crude can be removed, along with oxygen and nitrogen in a hydroprocessing unit of a refinery or a dedicated hydrotreater. Sulphur is measured by HRL method 1.14 in an ICP or sulphur analyser mounted within a furnace. Sulphur levels in the oil product are measured by USEPA method 5050. The gross calorific value is a direct result of the composition.

It represents the energy available from combustion of the sample. Chlorine is measured as high levels of chlorine or chloride have potential to corrode plant steels.

Ash composition is a measure of inorganic components present in the samples, for general feedstock and product quality assessment. Lignocellulosic materials including black liquor contain inorganic compounds, and some of the insoluble inorganics are expected to be carried over to the bio-crude product. Prior to further refining, e.g. by hydroprocessing, the ash should be removed, as some ash components are likely to adversely affect the catalysts used in hydroprocessing. Distillation is the most common way to do this, and a key difference between bio-crudes from Cat-HTR and pyrolysis bio-oils from e.g. fast pyrolysis is that the bio-crudes can be distilled but the pyrolysis oils cannot. This is because pyrolysis oils have high oxygen contents and low stability. Ash content of bio-crude may be removed by a distillation process at the front end of a refinery. Ash content is reported as a percentage on dry basis, the ash composition as reported in this document assumes that the inorganics are in their oxide forms. This assumption may mean that the sum of ash composition may exceed 100% and some other inorganics might not be accounted for.

Solvent Extraction

Solvent extraction is performed on a measured amount of the water phase product using diethyl ether to dissolve and separate recoverable oils from the water phase. Ether extraction produces results quantifying both the ether extractable chemicals and the residues of ether extraction.

Ether extractable chemicals are oils that are lighter fractions including alcohols, ketones, phenols and short chain hydrocarbons. Many of the phenols are used in the flavouring and essence industries. Solvent extraction is used as a rapid method of quantifying these organic components, that are potentially recoverable in a commercial plant, thereby adding to the overall oil yield and possibly representing an additional product stream of interest to the fine chemicals industry.

Residue from the extraction includes soluble ash from the feedstock, catalyst and water soluble (non-ether soluble) organics. The latter group includes glycolic and lactic acids, used respectively in the cosmetics and biopolymers industries. The catalyst can be regenerated, however, as it is inexpensive the choice between regenerating the catalyst and treating and disposing of the brine generated is influenced by site-specific factors. Potassium-based catalysts can also be used, in which case the catalyst residues plus additional potassium from the biomass may find application as fertilizer products.

Method of Ether Extraction

Weigh 100 g of sample.

Acidify to pH around 5, using sulphuric acid.

Add 100 to 150 ml ether.

Shake not stir.

Settle for 10 minutes, watching for separation by density.

Drain water off the bottom.

Pour ether into an evaporator flask, weighed before and after collection of ether extractables.

The ether extraction cycle is performed 3 times, on the same water, using fresh ether each time.

Residues are extracted from the water by drying at 110° C. in air and collecting (weighing) the solids.

There are some water soluble compounds derived from the wood that are not assessed by these methods, e.g. low molecular weight alcohols and ketones such as methanol, ethanol, and acetone. These compounds are known from 1H NMR and GC analysis to be present in significant quantity Cat-HTR liquors when Radiata pine is processed. Based on quantitation from previous studies on Radiata pine, a contribution to the mass balance of 6% of the organic material present in the feedstock has been included in the mass balances in this report.

Water Analysis

In addition to the gravimetric analysis by solvent extraction described above, water samples were analysed by Envirolab Services for a range of water quality parameters.

Example 2: Results

TABLE 4

Feedstock Analysis Results

| | | Radiata Pine | Spruce Pine Fir | Hogfuel | Black Liquor |
|---|---|---|---|---|---|
| Proximate Analysis | Moisture (% wt ar) | 5.7 | 43.8 | 60.0 | 53.9 |
| | Ash (% wt db) | 0.6 | 0.6 | 2.2 | 47.1 |
| | Volatiles (% wt db) | 79.8 | 79.5 | 79.4 | |
| | Fixed C. (% wt db) | 19.7 | 19.9 | 23.5 | |
| Ultimate Analysis | GCV (MJ/kg db) | 20.8 | 18.6 | | |
| | GCV (MJ/kg daf) | 21.0 | 18.7 | | |
| | Carbon (% wt db) | 52.3 | 52.1 | 52.9 | 37.5 |
| | Hydrogen (% wt db) | 6.2 | 6.3 | 6.0 | 1.7 |
| | Nitrogen (% wt db) | 0.06 | 0.21 | 0.25 | <0.01 |
| | Sulphur (% wt db) | 0.01 | 0.01 | 0.02 | 4.77 |
| | Oxygen (% wt db) | 40.8 | 40.8 | 38.7 | 3.2 |
| | Chlorine (%) | | | | 0.21 |
| | Molar H/C Ratio | 1.4 | | | 0.04 |
| Ash Constituents (% oxide in ash) | $SiO_2$ (% wt db) | | 2.3 | 1.1 | |
| | $Al_2O_3$ (% wt db) | | 1.1 | 0.62 | |
| | $Fe_2O_3$ (% wt db) | | 0.69 | 0.28 | |
| | $TiO_2$ (% wt db) | | 0.04 | 0.02 | |
| | $K_2O$ (% wt db) | | 16.3 | 7.6 | |
| | MgO (% wt db) | | 7.9 | 3.2 | |
| | $Na_2O$ (% wt db) | | 0.42 | 0.3 | |
| | CaO (% wt db) | | 33.9 | 46.7 | |
| | $SO_3$ (% wt db) | | 1.2 | 1 | |
| | $P_2O_5$ (% wt db) | | 2.2 | 2.5 | |
| | $Mn_3O_4$ (% wt db) | | 2.3 | 1.5 | |
| | SrO (% wt db) | | 0.12 | 0.24 | |
| | BaO (% wt db) | | 0.3 | 0.6 | |
| | ZnO (% wt db) | | 0.28 | 0.42 | |
| | CuO (% wt db) | | 0.2 | 0.06 | |
| | $Cr_2O_3$ (% wt db) | | 0.04 | 0 | |
| | $Co_3O_4$ (% wt db) | | 0 | 0 | |
| | NiO (% wt db) | | 0.02 | 0 | |
| | $V_2O_5$ (% wt db) | | 0 | 0 | |

Comparison of Feedstocks

Radiata Pine wood flour was used as a benchmark feedstock for biomass Cat-HTR. The SPF woodchip is unsurprisingly quite similar to the Radiata Pine in terms of proximate and ultimate analyses. The Hog Fuel has a higher ash content than either of the foregoing feedstocks, this is likely attributable to higher levels of bark, needles and other contaminants. The ash is dominated by calcium, which is basic under most conditions, and may have a catalytic effect in Cat-HTR. The sludge has a high ash content and the composition of the ash is dominated by calcium, which again may have a catalytic effect in Cat-HTR. The mixed feedstock used in the last two runs listed in table 3 can be expected to be dominated by the hog fuel and black liquor properties that comprise most of the feed.

One subtle but potentially significant difference between runs with sodium hydroxide as catalyst and with black liquor as catalyst is the point at which the catalyst is added into the process. In the SPP sodium hydroxide catalyst is normally injected at high pressure, after preheating of the feedstock slurry and mixing with the steam to heat the slurry to reaction temperature have occurred. In contrast, the black liquor trials have black liquor premixed into the slurry in the atmospheric pressure slurry mixing tank. The slurry and black liquor mixture passes through the main slurry high pressure pump, through the preheaters and through to the steam injection point. There it gains its final temperature for entry into the reactors. A consequence of the different processing approach is that the slurries containing the black liquor can be expected to start reacting earlier in the Cat-HTR process than those where the catalyst is added at a later point.

Trial Results

Tables 5 and 6 display a summary of mass balance data and non-condensable gas compositions.

The mass balances are closed to the extent that 79-107% of the mass of feedstock entering the Cat-HTR reactor during a certain steady state period of operation has been identified in the products collected from the tank in which it was captured (known as T4) or the gas stream venting from it. The exception is the run of 24/07/14 (hog fuel plus black liquor) which was very poorly closed. Typically with radiata pine wood flour runs we expect the mass balance to close in the vicinity of 85-100%. It should be noted that the mass balances are approximate only and are based on a number of simplifications and approximations, for the reason that it is not possible to quantify every component in the complex.

The wider variation in the extent of closure of the mass balance in with the feedstocks is most probably related to the greater complexity of the black liquor's inorganic components and the resulting uncertainty in the water phase composition.

TABLE 5

Summary of experimental trials liquids mass balance

| | Run ID No. | | | | | |
|---|---|---|---|---|---|---|
| | 20140521 | 20140523 | 20140716 | 20140724 | 20140731 | 20140814 |
| | \multicolumn{6}{c}{Feedstock} | | | | | |
| | 8% Licella radiata pine | 8% Licella radiata pine | 7.8% hog fuel | 8% hog fuel | 6.4% hog fuel, 1.44% wood, 0.16% sludge | 6.4% hog fuel, 1.44% wood, 0.16% sludge |
| | \multicolumn{6}{c}{Liquid Catalyst} | | | | | |
| | 1 kg diluted black liquor per dry kg wood | 1.3 kg diluted black liquor per dry kg wood | 12% sodium hydroxide | 1.3 kg diluted black liquor per dry kg wood | 1.3 kg diluted black liquor per dry kg mix | 1.3 kg diluted black liquor per dry kg mix |
| T4 Injection time (mins) | 67 | 71 | 68 | 92 | 83 | 61 |
| Percent solids in feed | 9.96% | 10.49% | 7.8% | 10.5% | 9.9% | 9.7% |
| Percent solids in reactors | 4.0% | 4.2% | 2.9% | 4.3% | 4.0% | 3.5% |
| Solids in feed (kg) | 4.1 | 4.5 | 2.8 | 6.2 | 5.0 | 3.0 |
| Solid product recovered (wet kg) | 1.085 | 1.118 | 0.763 | 1.258 | 1.134 | 0.521 |
| Moisture content of oil (%) | 12.4% | 18.5% | 14.7% | 16.7% | 12.9% | 20.1% |
| Bio crude recovered (dry kg) | 0.951 | 0.912 | 0.651 | 1.048 | 0.988 | 0.416 |
| Bio crude yield (dry) | 23.0% | 20.4% | 23.3% | 17.0% | 19.6% | 13.7% |
| NCG gas measured (m3/hr) | 0.43 | 0.43 | 0.34 | 0.43 | 0.47 | 0.42 |
| NCG density (kg/m3) | 1.59 | 1.55 | 1.23 | 1.60 | 1.60 | 1.52 |
| NCG (kg/hr) | 0.830 | 0.809 | 0.515 | 0.835 | 0.914 | 0.784 |
| Solids in feed (kg/hr) | 3.709 | 3.767 | 2.434 | 4.018 | 3.635 | 2.990 |
| NCG Yield | 22.4% | 21.5% | 21.2% | 20.8% | 25.1% | 26.2% |
| Total feed to T4-NCG (kg) | 103.7 | 104.4 | 93.6 | 141.5 | 124.4 | 85.5 |
| Ether extractable in liquor (%) | 0.48% | 0.56% | 0.394% | 0.402% | 1.440% | 0.574% |
| Ether extractable in liquor (kg) | 0.49 | 0.59 | 0.37 | 0.57 | 1.79 | 0.49 |
| Ether extractable yield | 11.9% | 13.2% | 13.2% | 9.2% | 35.6% | 16.1% |
| Solid residue in liquor (%) | 0.64% | 1.05% | 1.40% | 0.81% | 0.88% | 0.66% |

TABLE 5-continued

Summary of experimental trials liquids mass balance

| | Run ID No. | | | | | |
|---|---|---|---|---|---|---|
| | 20140521 | 20140523 | 20140716 | 20140724 | 20140731 | 20140814 |
| | Feedstock | | | | | |
| | 8% Licella radiata pine | 8% Licella radiata pine | 7.8% hog fuel | 8% hog fuel | 6.4% hog fuel, 1.44% wood, 0.16% sludge | 6.4% hog fuel, 1.44% wood, 0.16% sludge |
| | Liquid Catalyst | | | | | |
| | 1 kg diluted black liquor per dry kg wood | 1.3 kg diluted black liquor per dry kg wood | 12% sodium hydroxide | 1.3 kg diluted black liquor per dry kg wood | 1.3 kg diluted black liquor per dry kg mix | 1.3 kg diluted black liquor per dry kg mix |
| Solid residue in liquor (kg) | 0.66 | 1.09 | 1.31 | 1.15 | 1.10 | 0.56 |
| Solid residue from catalyst (kg) | 0 | 0 | 0.34 | 0.00 | 0.00 | 0.00 |
| Solid residue in liquor yield | 16.0% | 24.5% | 34.9% | 18.7% | 21.8% | 18.4% |
| % black liquor solids in feed | 25.6% | 30.9% | 0.0% | 31.0% | 30.9% | 30.9% |
| % Inorganic material in feed | 12.1% | 14.5% | 0.0% | 14.6% | 15.9% | 15.9% |
| Organic material in feed (kg) | 3.64 | 3.81 | 2.79 | 5.26 | 4.23 | 4.23 |
| Methanol ethanol & acetone yield (kg) | 0.22 | 0.23 | 0.17 | 0.32 | 0.25 | 0.25 |
| Methanol, ethanol & acetone yield (%) | 5.28% | 5.13% | 6.00% | 5.13% | 5.04% | 5.04% |
| Yield Summary | | | | | | |
| Solid oil Yield (dry) | 23.0% | 20.4% | 23.3% | 17.0% | 19.6% | 13.7% |
| NCG Yield | 22.4% | 21.5% | 21.2% | 20.8% | 25.1% | 26.2% |
| Ether extractable yield | 11.9% | 13.2% | 13.2% | 9.2% | 35.6% | 16.1% |
| Solid residue in liquor yield | 16.0% | 24.5% | 34.9% | 18.7% | 21.8% | 18.4% |
| Methanol, ethanol & acetone yield (%) | 5.3% | 5.1% | 6.0% | 5.1% | 5.0% | 5.0% |
| Total | 78.54% | 84.76% | 98.58% | 70.87% | 107.24% | 79.54% |
| Cooler inlet temp | 335 | 335 | 315 | 315 | 310 | 335 |
| Estimated mixing (Reactor inlet) temp | 355 | 355 | 335 | 335 | 330 | 355 |
| Liquor pH | 5.59 | 7.17 | 8.18 | 7.15 | 7.09 | 7.07 |

TABLE 6

Summary of Cat-HTR trials non-condensable gases

| | Run ID No. | Methane | Carbon Monoxide | Hydrogen | Ethylene | Ethane | Propylene | Propane | Carbon Dioxide | H2S (ppm) | HHV (MJ/kg) | NCG Yield |
|---|---|---|---|---|---|---|---|---|---|---|---|---|
| R pine + 1:1 black liquor | 20140521 | 4.51% | 0.11% | 10.11% | 0.43% | 0.69% | 1.84% | 0.37% | 81.68% | 2537 | 3.50 | 22.37% |
| R pine + 1:1.3 black liquor | 20140523 | 5.34% | 0.05% | 12.00% | 0.37% | 0.83% | 1.60% | 0.38% | 79.21% | 2173 | 3.84 | 21.48% |
| Hogfuel + catalyst | 20140716 | 3.69% | 0.01% | 31.24% | 0.36% | 0.58% | 1.04% | 0.38% | 62.71% | <150 | 5.61 | 21.16% |
| Hogfuel + BL | 20140724 | 5.00% | 0.05% | 9.56% | 0.29% | 0.71% | 1.59% | 0.38% | 82.23% | 1779 | 3.40 | 20.79% |
| Full mix | 20140731 | 4.79% | 0.04% | 9.74% | 0.28% | 0.77% | 1.46% | 0.41% | 82.32% | 1749 | 3.33 | 25.15% |
| Full mix higher temp | 20140814 | 5.12% | 0.04% | 13.75% | 0.36% | 0.86% | 1.36% | 0.38% | 77.93% | 2582 | 3.88 | 26.24% |

Bio-Crude Yields

Typical bio-crude yields from a Radiata pine wood flour feedstock in the Small Pilot Plant are mid-to-low twenties percent on a dry wood feed basis. Those yields are lower than obtained in Licella's Larger Pilot Plants which are typically around mid-thirties percent or more.

The main reason for the difference is the lower maximum slurry concentrations that can be pumped in the SPP, and the amount of steam used for heating the slurry to reaction temperature, which is much larger for the SPP than for the LPP. Generally, higher concentrations of biomass in the Cat-HTR reactor (and lower concentrations of water) favour higher yields of bio-crude at the expense of the proportion of the organic material that dissolves in the water phase.

Superficially, conversion of around ⅓ of the feed biomass to bio-crude may like quite a low yield, however, considerable energy densification has occurred in that step by removal of oxygen. More than half of mass of the sugar polymers comprising hemicellulose and cellulose is oxygen. The oxygen is removed mainly as carbon dioxide gas but also as salts of small carboxylic acids such as sodium acetate which dissolve in the water phase. A rule of thumb for the fate of woody biomass in Cat-HTR is that one third of the mass is converted to biocrude, one third to gas, mainly CO2, and one third to water soluble chemicals. The bio-crude yields from the feedstocks are generally in line with those expected from the SPP, with the exception of 14/08/14 run where the amount of bio-crude recovered was low.

The reason for this is unknown, but it is likely that some bio-crude was trapped in the apparatus and not recovered.

Gas Yields & Compositions

Generally, non-condensable gas (NCG) yields are slightly lower for all experiments than typical (30%) for Radiata Pine wood flour under conditions of 12% catalyst loading, 240 bar pressure and 340 degrees. In the case of the radiata pine plus black liquor runs this is likely due to slightly lower gasification activity of the black liquor derived catalysts and to the reduced proportion of cellulose (black liquor contains mostly lignin and hemicellulose as organic components) compared to radiata pine wood flour. In the case of the hog fuel dominated runs the lower NCG make is probably also related to the lower temperature reaction temperatures chosen. The main difference in gas composition between sodium hydroxide catalysed runs and black liquor catalysed runs is that the hydrogen make is lower and the hydrogen sulphide make is higher for the latter systems. The $H_2S$ make for sodium hydroxide catalysed systems with radiata pine feed is essentially negligible. The proportion of $H_2S$ in the gas is not a simple function of black liquor concentration, as can be seen from the first two entries in tables 5 and 6. This is possibly a function of the pH of the aqueous phase. A typical wood+sodium hydroxide catalyst product by Licella produces approximately 20% H2 by volume in the non condensable gas product. The hog fuel+sodium hydroxide run produced a greater fraction of H2 than this, possibly indicating that the ash components in the hog fuel have some catalytic activity in gasification.

Water-Phase Components

The water-soluble components have the greatest uncertainty associated with them, particularly in the case of those runs utilizing black liquor. In the case of radiata pine plus sodium hydroxide catalyst, the dominant water soluble components are acetates, hydrogen carbonates, phenols, ketones, catechols, ethanol and methanol, and humic materials (brown water soluble compounds, insoluble in diethyl ether). In the case of the black liquor as catalyst, the water soluble chemistry is likely to be more complex still.

The Ultimate and Proximate analysis of bio-crude product is tabulated below, providing direct comparison of all successful Cat-HTR trials. Individual runs are described in Table 7.

TABLE 7

Summary of Experimental Trials Bio-Crude Product

| | Description | Radiata Pine BL 20140521 | Radiata Pine BL 20140523 | Hog Fuel + Catalyst 20140716 | Hog Fuel + BL 20140724 | Mixed Feed + BL 20140731 | Mixed Feed + BL 20140814 | Radiata Pine Typical |
|---|---|---|---|---|---|---|---|---|
| Proximate Analysis | Moisture (% wt ar) | 8 | 1.6 | | 6 | 7.5 | 4 | |
| | Ash (% wt db) | 0.5 | 0.4 | 6.6 | 2.8 | 2.6 | 2.0 | |
| | Volatiles (% wt db) | | | | | | | 0.79 |
| | Fixed C (% wt db) | | | | | | | |
| Ultimate Analysis | GCV (MJ/kg db) | 34.8 | 34.2 | 33.9 | 32.6 | 33.0 | 33.0 | |
| | GCV (MJ/kg daf) | 34.97 | 34.34 | 36.29 | 33.50 | 33.89 | 33.66 | 33.50 |
| | Carbon (% wt db) | 73.4 | 80.3 | 76.7 | 75.1 | 79.2 | 77.6 | 33.8 |
| | Hydrogen (% wt db) | 6.5 | 7.2 | 7.2 | 6.6 | 6.4 | 6.9 | |
| | Nitrogen (% wt db) | 0.1 | 0.2 | 0.3 | 0.3 | 0.4 | 0.3 | |
| | Sulphur (% wt, db) | 0.6 | 0.7 | 0.1 | 1.1 | 0.6 | 0.6 | |
| | Oxygen (% wt db) | 18.9 | 13.0 | 9.6 | 12.7 | 10.2 | 12.4 | |
| | Chlorine (%) | | | | | | | |
| | Molar H/C Ratio | | | | | | | |
| Ash Constituents (% oxide in ash) | SiO2 (% wt, db) | 3.6 | 5.4 | 0.8 | 3 | 3.3 | 3.3 | |
| | Al2O3 (% wt db) | 4.4 | 3.9 | 1.7 | 3.7 | 4.9 | 5 | |
| | Fe2O3 (% wt db) | 5.6 | 2.5 | 1.4 | 9.9 | 6.6 | 5.1 | |
| | TiO2 (% wt db) | 0.08 | 0.07 | 0.05 | 0.13 | 0.15 | 0.21 | |
| | K2O (% wt db) | 1.4 | 3.7 | 0.34 | 0.44 | 0.72 | 0.81 | |

TABLE 7-continued

Summary of Experimental Trials Bio-Crude Product

| Description | Radiata Pine BL 20140521 | Radiata Pine BL 20140523 | Hog Fuel + Catalyst 20140716 | Hog Fuel + BL 20140724 | Mixed Feed + BL 20140731 | Mixed Feed + BL 20140814 | Radiata Pine Typical |
|---|---|---|---|---|---|---|---|
| MgO (% wt db) | 1.7 | 2 | 3.7 | 3.7 | 4.8 | 4.8 | |
| Na2O (% wt db) | 13.1 | 27.9 | 7.2 | 3.6 | 5.5 | 6.7 | |
| CaO (% wt db) | 3.2 | 3.7 | 46.6 | 36.2 | 42.1 | 42.4 | |
| SO3 (% wt db) | 19.1 | 38 | 1.1 | 24.3 | 20.6 | 19.9 | |
| P2O5 (% wt db) | 0.6 | 0.51 | 2.5 | 3.6 | 3.5 | 3.5 | |
| Mn3O4 (% wt db) | 0.24 | 0.32 | 1.17 | 1.39 | 0.3 | 0.3 | |
| SrO (% wt db) | <0.01 | <0.01 | 0.17 | 0.17 | 0.6 | 0.5 | |
| BaO (% wt db) | 0.04 | 0.04 | 0.4 | 0.5 | <0.1 | 0.1 | |
| ZnO (% wt db) | 0.2 | 0.16 | 0.31 | 0.56 | <0.1 | <0.1 | |
| CuO (% wt db) | 0.36 | 0.32 | 0.11 | 0.17 | 0.2 | 0.2 | |
| Cr2O3 (% wt db) | 0.16 | 0.07 | 0.02 | 0.02 | 1.7 | 2.3 | |
| Co3O4 (% wt db) | 0 | 0 | <0.1 | <0.1 | <0.1 | <0.1 | |
| NiO (% wt db) | 0.04 | 0.05 | 0.02 | 0.02 | <0.1 | <0.1 | |
| V2O5 (% wt db) | 0.52 | 0.09 | 0 | 0 | 0.5 | 0.6 | |

Radiata Pine Wood Flour with Black Liquor 20140521

Operating Conditions (Wood Flour w/-Black Liquor 20140521)

Table 8 below shows the operating conditions of the mass balance run on Radiata Pine Wood Flour. This run produced the samples of Bio-Crude Oil, syngas and water, that are presented in the next section.

TABLE 8

Cat-HTR Operating Conditions, Radiata Wood Flour 20140521

| | |
|---|---|
| Reactor Temperature | 355° C. |
| Reactor Pressure | 220 to 249 bar |
| Reactor Residence Time | 25 minutes |

Mass Balance (Wood Flour w/-Black Liquor 20140521)

A product mass balance summary of the trial is provided in Table 9 below. 4.1 kg of Stock Black liquor was used in this feedstock slurry (1:1 by mass db).

TABLE 9

Wood Flour Black Liquor Mass Balance 20140521

| | |
|---|---|
| Date | 2014 May 2 |
| Feedstock | 8% Licella radiata pine |
| Liquid Catalyst | 1 kg stock black liquor per dry kg wood |
| T4 injection time (mins) | 67 |
| Percent solids in feed | 9.96% |
| Percent solids in reactors | 4.0% |
| Solids in feed (kg) | 4.1 |
| Solid product recovered (wet kg) | 1.085 |
| Moisture content of oil (%) | 12.4% |

TABLE 9-continued

Wood Flour Black Liquor Mass Balance 20140521

| | |
|---|---|
| B o crude recovered (dry kg) | 0.951 |
| B o crude yield (dry) | 23.0% |
| NCG gas measured (m3/hr) | 0.43 |
| NCG density (kg/m3) | 1.59 |
| NCG (kg/hr) | 0.830 |
| Solids in feed (kg/hr) | 3.709 |
| NCG yield | 22.4% |
| Total feed to T4 - NCG (kg) | 103.7 |
| Ether extractable in liquor (%) | 0.48% |
| Ether extractable in liquor (kg) | 0.49 |
| Ether extractable yield | 11.9% |
| Solid residue in liquor (%) | 0.64% |
| Solid residue in liquor (kg) | 0.66 |
| Solid residue from catalyst (kg) | 0 |
| Solid residue in liquor yield | 16.0% |
| % black liquor solids in feed | 25.6% |
| % inorganic material in feed | 12.1% |
| Organic material in feed (kg) | 3.64 |
| Methanol ethanol & acetone yield | 0.22 |
| Methanol ethanol & acetone yield (%) | 5.28% |
| Yield Summary | |
| Bio crude yield (dry) | 23.0% |
| NCG yield | 22.4% |
| Ether extractable yield | 11.9% |
| Solid residue in liquor yield | 16.0% |

TABLE 9-continued

Wood Flour Black Liquor Mass Balance 20140521

| | |
|---|---|
| Methanol ethanol & acetone yield (%) | 5.3% |
| Total | 78.54% |
| Cooler inlet temp | 335 |
| Estimated mixing (Reactor inlet) temp | 355 |

Notes:
All mass balance data is referenced to the feedstock mass on a dry basis.

Gas Analysis (Wood Flour w/-Black Liquor 20140521)

TABLE 10

Non Condensable Gas Analysis from Radiata Wood Flour 20140521

| Methane | CO | Hydrogen | Ethylene | Ethane | Propylene | Propane | $CO_2$ | $H_2S$ |
|---|---|---|---|---|---|---|---|---|
| 4.51 | 0.11% | 10.11% | 0.43% | 0.43% | 1.84% | 0.37% | 81.7% | 0.25% |

Bio-Crude Analysis of Wood Chip 20140521

TABLE 11

Analysis of Bio-Crude Oil (wood flour w/- black liquor 20140521)

| Description | | Pine BL 20140521 |
|---|---|---|
| Proximate Analysis | Moisture (% wt ar) | 8 |
| | Ash (% wt db) | 0.5 |
| | Volatiles (% wt db) | |
| | Fixed C. (% wt db) | |
| Ultimate Analysis | GCV (% MJ/kg) | 34.8 |
| | Carbon (% wt db) | 73.4 |
| | Hydrogen (% wt db) | 6.5 |
| | Nitrogen (% wt db) | 0.11 |
| | Sulphur (% wt db) | 0.56 |
| | Oxygen (% wt db) | |
| | Chlorine (%) | |
| | Molar H/C Ratio | |
| Ash Constituents (% oxide in ash) | $SiO_2$ (% wt db) | 3.6 |
| | $Al_2O_3$ (% wt db) | 4.4 |
| | $Fe_2O_3$ (% wt db) | 5.6 |
| | $TiO_2$ (% wt db) | 0.08 |
| | $K_2O$ (% wt db) | 1.4 |
| | MgO (% wt db) | 1.7 |
| | $Na_2O$ (% wt db) | 13.1 |
| | CaO (% wt db) | 3.2 |
| | $SO_3$ (% wt db) | 19.1 |
| | $P_2O_5$ (% wt db) | 0.6 |
| | $Mn_3O_4$ (% wt db) | 0.24 |
| | SrO (% wt db) | <0.01 |
| | BaO (% wt db) | 0.04 |
| | ZnO (% wt db) | 0.2 |
| | CuO (% wt db) | 0.36 |
| | $Cr_2O_3$ (% wt db) | 0.16 |
| | $Co_3O_4$ (% wt db) | 0 |
| | NiO (% wt db) | 0.04 |
| | $V_2O_5$ (% wt db) | 0.52 |

The Bio-Crude Oil has a gross calorific value of 35 MJ/kg.

Solvent Extraction of Bio-Crude

Extraction of the oil from wood chip process water with the solvent diethyl ether gave 11.9% extractables as a fraction of the feedstock (dry basis). Total oils recoverable (bio-crude plus ether extractables were 34.9% of the feed mass.

Radiata Pine Wood Flour with Black Liquor 20140523

Operating Conditions (Wood Flour w/-Black Liquor 20140523)

Table 12 below shows the operating conditions of the mass balance run using wood flour w/-black liquor.

TABLE 12

Operating Conditions for Radiata Pine Wood Flour with Black Liquor 20140523

| | |
|---|---|
| Reactor Temperature | 355° C. |
| Reactor Pressure | 224 to 241 bar |
| Reactor Residence Time | 25 minutes |

Mass Balance (Wood Flour w/-Black Liquor 20140523)

This trial was performed using black liquor at a ratio of 7.75 kg of stock black liquor to 150 L of slurry. Slurry contained 8% Radiata pine wood flour db. Stock black liquor to wood ratio is 1:1.3 db.

TABLE 13

Mass Balance wood flour w/- black liquor 20140523

| Date | 2014 May 23 |
|---|---|
| Feedstock | 8% Licella radiata pine |
| Liquid Catalyst | 1.3 kg stock black liquor per dry kg wood |
| T4 Injection time (mins) | 71 |
| Percent Solids in Feed | 10.49% |
| Percent Solids in reactors | 4.2% |
| Solids in feed (kg) | 4.5 |
| Solid product recovered (wet kg) | 1.118 |
| Moisture content of oil (%) | 18.5% |
| Bio crude recovered (dry kg) | 0.912 |
| Bio crude yield (dry) | 20.4% |
| NCG gas measured (m3/hr) | 0.43 |
| NCG density (kg/m3) | 1.55 |
| NCG (kg/hr) | 0.809 |
| Solids in feed (kg/hr) | 3.767 |
| NCG yield | 21.5% |
| Total feed to T4- NCG (kg) | 104.4 |
| Ether extractable in liquor (%) | 0.56% |
| Ether extractable in liquor (kg) | 0.59 |
| Ether extractable yield | 13.2% |
| Solid residue in liquor (%) | 1.05% |
| Solid residue in liquor (kg) | 1.09 |
| Solid residue from catalyst (kg) | 0 |
| Solid residue in liquor yield | 24.5% |
| % black liquor solids in feed | 30.9% |
| % Inorganic material in feed | 14.5% |
| Organic material in feed (kg) | 3.81 |
| Methanol ethanol & acetone yield (kg) | 0.23 |
| Methanol, ethanol & acetone yield (%) | 5.13% |
| Yield Summary | |
| Bio crude yield (dry) | 20.4% |
| NCG yield | 21.5% |
| Esther extractable yield | 13% |
| Solid residue in liquor yield | 25% |
| Methanol, ethanol & acetone yield (%) | 5% |
| Total | 84.76% |
| Cooler inlet temp | 335 |
| Estimated mixing (Reactor inlet) temp | 355 |

Gas Analysis (Wood Flour w/-Black Liquor 20140523)

TABLE 14

Non Condensable Gas Analysis for Radiata Pine Wood Flour with Black Liquor 20140523

| Methane | CO | Hydrogen | Ethylene | Ethane | Propylene | Propane | $CO_2$ | $H_2S$ |
|---|---|---|---|---|---|---|---|---|
| 5.34% | 0.05% | 12.00% | 0.37% | 0.83% | 1.60% | 0.38% | 79.2% | 0.22% |

Bio-Crude Analysis (Wood Flour w/-Black Liquor 20140523)

TABLE 15

Analysis of Bio-Crude Oil

| Description | | Pine BL 20140523 |
|---|---|---|
| Proximate Analysis | Moisture (% wt ar) | 1.6 |
| | Ash (% wt db) | 0.4 |
| | Volatiles (% wt db) | |
| | Fixed C. (% wt db) | |
| Ultimate Analysis | GCV (% MJ/kg) | 34.2 |
| | Carbon (% wt db) | 80.3 |
| | Hydrogen (% wt db) | 7.2 |
| | Nitrogen (% wt db) | 0.18 |
| | Sulphur (% wt db) | 0.68 |
| | Oxygen (% wt db) | 13.0 |
| | Chlorine (%) | |
| | Molar H/C Ratio | |
| Ash Constituents (% oxide in ash) | $SiO_2$ (% wt db) | 5.4 |
| | $Al_2O_3$ (% wt db) | 3.9 |
| | $Fe_2O_3$ (% wt db) | 2.5 |
| | $TiO_2$ (% wt db) | 0.07 |
| | $K_2O$ (% wt db) | 3.7 |
| | $MgO$ (% wt db) | 2 |
| | $Na_2O$ (% wt db) | 27.9 |
| | $CaO$ (% wt db) | 3.7 |
| | $SO_3$ (% wt db) | 38 |
| | $P_2O_5$ (% wt db) | 0.51 |
| | $Mn_3O_4$ (% wt db) | 0.32 |
| | $SrO$ (% wt db) | <0.01 |
| | $BaO$ (% wt db) | 0.04 |
| | $ZnO$ (% wt db) | 0.16 |
| | $CuO$ (% wt db) | 0.32 |
| | $Cr_2O_3$ (% wt db) | 0.07 |
| | $Co_3O_4$ (% wt db) | 0 |

TABLE 15-continued

Analysis of Bio-Crude Oil

| Description | | Pine BL 20140523 |
|---|---|---|
| | NiO (% wt db) | 0.05 |
| | V2O5 (% wt db) | 0.09 |

The Cat-HTR processing temperatures (355° C. to 335° C.) were again within the normal Biomass processing temperatures The ash content of the Bio-Crude Oil was about 0.4%. The Bio-Crude Oil has a gross calorific value of 34.3 MJ/kg.

Solvent Extraction of Bio-Crude (Wood Flour w/-Black Liquor 20140523)

Extraction of the oil from wood chip process water with the solvent diethyl ether gave 13.2% extractables as a fraction of the feedstock (dry basis). Total oils recoverable (bio-crude plus ether extractables) were 33.6% of the feed mass.

Hog Fuel w/-Sodium Hydroxide 20140716

Operating Conditions (Hog Fuel w/-Sodium Hydroxide 20140716)

Table 16 below shows the operating conditions of the mass balance run on 16 Jul. 2014, on Canfor Hog Fuel and sodium hydroxide. This run produced the samples of Bio-Crude Oil, syngas and water, that are presented in the next section.

TABLE 16

Operating Conditions (Hog Fuel w/- Sodium Hydroxide 20140716)

| | |
|---|---|
| Reactor Temperature | 335 to 315° C. |
| Reactor Pressure | 227 bar |
| Reactor Residence Time | 25 minutes |

Mass Balance (Hog Fuel w/-Sodium Hydroxide 20140716)

This trial was performed using sodium hydroxide at a ratio of 11.2% by weight to feedstock db (target ratio was 12%, catalyst injection VSD was at 100% and pump stroke length was not adjustable during the run). Slurry contained 7.8% hog fuel db.

TABLE 17

Mass Balance (Hog Fuel w/- Sodium Hydroxide 20140716)

| | |
|---|---|
| Date | 2014 Jul. 16 |
| Feedstock | 7.8% hog fuel |
| Liquid Catalyst | 12% sodium hydroxide |
| T4 Injection time (mins) | 68 |
| Percent Solids in Feed | 7.8% |
| Percent Solids in reactors | 2.9% |
| Solids in feed (kg) | 2.8 |
| Solid product recovered (wet kg) | 0.763 |
| Moisture content of oil (%) | 14.7% |
| Bio crude recovered (dry kg) | 0.651 |
| Bio crude yield (dry) | 23.3% |
| NCG gas measured (m3/hr) | 0.34 |
| NCG density (kg/m3) | 1.23 |
| NCG (kg/hr) | 0.515 |
| Solids in feed (kg/hr) | 2.434 |
| NCG yield | 21.2% |
| Total feed to T4 - NCG (kg) | 93.6 |
| Ether extractable in liquor (%) | 0.394% |
| Ether extractable in liquor (kg) | 0.37 |
| Ether extractable yield | 13.2% |
| Solid residue in liquor (%) | 1.40% |
| Solid residue in liquor (kg) | 1.31 |
| Solid residue from catalyst (kg) | 0.34 |
| Solid residue in liquor yield | 34.9% |
| % black liquor solids in feed | 0.0% |
| % Inorganic material in feed | 0.0% |
| Organic material in feed (kg) | 2.79 |
| Methanol ethanol & acetone yield (kg) | 16.8% |
| Methanol, ethanol & acetone yield (%) | 6.00% |
| Yield Summary | |
| Bio crude yield (dry) | 23.3% |
| NCG yield | 21.2% |
| Ether extractable yield | 13.2% |
| Solid residue in liquor yield | 34.9% |
| Methanol, ethanol & acetone yield (%) | 6.0% |
| Total | 98.58% |
| Cooler inlet temp | 315 |
| Estimated mixing (Reactor inlet) temp | 335 |

Gas Analysis (Hog Fuel w/-Sodium Hydroxide 20140716)

TABLE 18

Non Condensable Gas Analysis (Hoo Fuel w/-Sodium Hydroxide 20140716)

| Methane | CO | Hydrogen | Ethylene | Ethane | Propylene | Propane | $CO_2$ | $H_2S$ |
|---|---|---|---|---|---|---|---|---|
| 3.69% | 0.01% | 31.24% | 0.36% | 0.58% | 1.04% | 0.38% | 62.7% | 0.00% |

Bio-Crude Analysis (Hog Fuel w/-Sodium Hydroxide 20140716) Data presented in Table 19 below is from the mass balance run.

TABLE 19

Analysis of Bio-Crude Oil (Hog Fule w/- Sodium Hydroxide

| Description | | Hog Fuel + Catalyst 20140716 |
|---|---|---|
| Proximate Analysis | Moisture (% wt ar) | 6.6 |
| | Ash (% wt db) | |
| | Volatiles (% wt db) | |
| | Fixed C. (% wt db) | |
| Ultimate Analysis | GCV (% MJ/kg) | 33.9 |
| | Carbon (% wt db) | 76.7 |
| | Hydrogen (% wt db) | 7.2 |
| | Nitrogen (% wt db) | 0.3 |
| | Sulphur (% wt db) | 0.1 |
| | Oxygen (% wt db) | 9.6 |
| | Chlorine (%) | |
| | Molar H/C Ratio | |
| Ash Constituents (% oxide in ash) | $SiO_2$ (% wt db) | 0.8 |
| | $Al_2O_3$ (% wt db) | 1.7 |
| | $Fe_2O_3$ (% wt db) | 1.4 |
| | $TiO_2$ (% wt db) | 0.05 |
| | $K_2O$ (% wt db) | 0.34 |
| | MgO (% wt db) | 3.7 |
| | $Na_2O$ (% wt db) | 7.2 |
| | CaO (% wt db) | 46.6 |
| | $SO_3$ (% wt db) | 1.1 |
| | $P_2O_5$ (% wt db) | 2.46 |
| | $Mn_3O_4$ (% wt db) | 1.17 |
| | SrO (% wt db) | 0.17 |
| | BaO (% wt db) | 0.4 |
| | ZnO (% wt db) | 0.31 |
| | CuO (% wt db) | 0.11 |
| | $Cr_2O_3$ (% wt db) | 0.02 |
| | $Co_3O_4$ (% wt db) | |
| | NiO (% wt db) | 0.02 |
| | $V_2O_5$ (% wt db) | |

The Cat-HTR processing temperatures for the Hog Fuel Sodium Hydroxide were steady for the most part at 335° C. reactor inlet temperature (variable between 326° C. and 337° C.), pressure was steady for the most part at 271 bar, variable at its lowest to 230 bar.

The ash content of the Bio-Crude Oil was about 6.6%.

The Bio-Crude Oil has a gross calorific value of 36.3 MJ/kg, for comparison purposes diesel is around 45 MJ/kg.

Solvent Extraction of Bio-Crude (Hog Fuel w/-Sodium Hydroxide 20140716)

Extraction of the oil from Hog Fuel Cat-HTR water with the solvent diethyl ether gave 13.2% extractables as a fraction of the feedstock (dry basis). Total oils recoverable (bio-crude plus ether extractables) were 36.5% of the feed mass.

Hog Fuel w/-Black Liquor (20140724)

Operating Conditions (Hog Fuel w/-Black Liquor 20140724)

Table 20 below shows the operating conditions of a mass balance run using Canfor Hog Fuel Black Liquor.

TABLE 19

Operating Conditions (Hop Fuel w/-Black Liquor 20140724)

| Reactor Temperature | 335 to 315° C. |
|---|---|
| Reactor Pressure | 226 to 244 bar |
| Reactor Residence Time | 25 minutes |

Mass Balance (Hog Fuel w/-Black Liquor 20140724)

This trial was performed using black liquor at a ratio of 9.7 kg of stock black liquor to 7.44 kg of hog fuel db. Slurry contained 8.6% Hog Fuel db. Stock black liquor to Hog fuel ratio is 1:1.3 db.

TABLE 21

Mass Balance (Hog Fuel w/-Black Liquor 20140724)

| Date | 2014 Jul. 24 |
|---|---|
| Feedstock | 8% hog fuel |
| Liquid Catalyst | 1.3 kg stock black liquor per dry kg wood |
| T4 Injection time (mins) | 92 |
| Percent Solids in Feed | 10.5% |
| Percent Solids in reactors | 4.3% |
| Solids in feed (kg) | 6.2 |
| Solid product recovered (wet kg) | 1.258 |
| Moisture content of oil (%) | 16.7% |
| Bio crude recovered (dry kg) | 1.048 |
| Bio crude yield (dry) | 17.0% |
| NCG gas measured (m3/hr) | 0.43 |
| NCG density (kg/m3) | 1.60 |
| NCG (kg/hr) | 0.835 |
| Solids in feed (kg/hr) | 4.018 |
| NCG yield | 20.8% |
| Total Feed to T4 - NCG (kg) | 141.5 |
| Ether extractable in liquor (%) | 0.402% |
| Ether extractable in liquor (kg) | 0.57 |
| Ether extractable yield | 9.2% |
| Solid residue in liquor (%) | 0.81% |
| Solid residue in liquor (kg) | 1.15 |
| Solid residue from catalyst (kg) | 0.00 |
| Solid residue in liquor yield | 18.7% |
| % black liquor solids in feed | 31.0% |
| % inorganic material in feed | 14.6% |
| Organic material in feed {kg) | 526.2% |
| Methanol ethanol & acetone yield (kg) | 31.6% |
| Methanol ethanol & acetone yield (%) | 5.13% |
| Yield Summary | |
| Bio crude yield (dry) | 17.0% |
| NCG yield | 20.8% |
| Ether extractable yield | 9.2% |

TABLE 21-continued

Mass Balance (Hog Fuel w/-Black Liquor 20140724)

| | |
|---|---|
| Solid residue in liquor yield | 18.7% |
| Methanol ethanol & acetone yield (%) | 5.1% |
| Total | 70.87% |
| Cooler inlet temp | 315 |
| Estimated mixing (Reactor) temp | 335 |

Gas Analysis (Hog Fuel w/-Black Liquor 20140724)

TABLE 22

Non Condensable Gas Analysis (Hog Fuel w/-Black Liquor 20140724)

| Methane | CO | Hydrogen | Ethylene | Ethane | Propylene | Propane | $CO_2$ | $H_2S$ |
|---|---|---|---|---|---|---|---|---|
| 5.00% | 0.05% | 9.56% | 0.29% | 0.71% | 1.59% | 0.38% | 82.2% | 0.18% |

Bio-Crude Analysis (Hog Fuel w/-Black Liquor 20140724)

Data presented in the Table 23 below is from the mass balance run.

TABLE 23

Analysis of Bio-Crude Oil (Hog Fule w/-Black Liquor 20140724

| Description | | Hog Fuel + BL 20140724 |
|---|---|---|
| Proximate Analysis | Moisture (% wt ar) | 6 |
| | Ash (% wt db) | 2.8 |
| | Volatiles (% wt db) | |
| | Fixed C. (% wt db) | |
| Ultimate Analysis | GCV (% MJ/kg) | 32.6 |
| | Carbon (% wt db) | 75.1 |
| | Hydrogen (% wt db) | 6.6 |
| | Nitrogen (% wt db) | 0.3 |
| | Sulphur (% wt db) | 1.1 |
| | Oxygen (% wt db) | 12.7 |
| | Chlorine (%) | |
| | Molar H/C Ratio | |
| Ash Constituents (% oxide in ash) | SiO2 (% wt db) | 3 |
| | Al2O3 (% wt db) | 3.7 |
| | Fe2O3 (% wt db) | 9.9 |
| | TiO2 (% wt db) | 0.13 |
| | K2O (% wt db) | 0.44 |
| | MgO (% wt db) | 3.7 |
| | Na2O (% wt db) | 3.6 |
| | CaO (% wt db) | 36.2 |
| | SO3 (% wt db) | 24.3 |
| | P2O5 (% wt db) | 3.55 |
| | Mn3O4 (% wt db) | 1.39 |
| | SrO (% wt db) | 0.17 |
| | BaO (% wt db) | 0.5 |
| | ZnO (% wt db) | 0.56 |
| | CuO (% wt db) | 0.17 |
| | Cr2O3 (% wt db) | 0.02 |
| | Co3O4 (% wt db) | <0.1 |
| | NiO (% wt db) | 0.02 |
| | V2O5 (% wt db) | 0 |

The processing temperatures for the Hog Fuel w/-black liquor was essentially steady around 330° C. reactor inlet temperature. Pressure was variable between 226 and 244 bar. The ash content of the Bio-Crude Oil was about 2.8%. The Bio-Crude Oil has a gross calorific value of 32.6 MJ/kg, for comparison purposes diesel is around 45 MJ/kg.

Solvent Extraction of Bio-Crude (Hog Fuel w/-Black Liquor 20140724)

Extraction of the oil from Hog Fuel w/-black liquor process water with the solvent diethyl ether gave 9.2% extractables as a fraction of the feedstock (dry basis). Taking the oil yield as 26.3%.

Mixed Kraft Feedstock Moderate Temperature 20140731

Operating Conditions (Mixed Kraft Feedstocks 20140731)

Table 24 below shows the operating conditions of the mass balance run using Mixed Kraft Feedstock. This trial was at moderate temperature of 321° C.

TABLE 24

| Operating Conditions (Mixed Kraft Feedstocks 20140731) | |
|---|---|
| Reactor Temperature | 335 to 315° C. |
| Reactor Pressure | 250 bar |
| Reactor Residence Time | 25 minutes |

Mass Balance of Canfor Mixed Feedstocks Cat-HTR 20140724

The Mixed Kraft Feedstock mixture is composed from solids:

TABLE 25

Mass Balance (Mixed Kraft Feedstocks 20140731)
The mixed kraft feedstock is composed from solids:

|  | kg to feed tank | % of dry feed |
|---|---|---|
| Hog Fuel | 8.0 | 55.3% |
| Pine | 1.8 | 12.4% |
| Sludge | 0.2 | 1.4% |
| Black liquor solids | 4.5 | 30.9% |
| Black liquor water | 8.5 | |
| Water | 123.5 | |
| Slurry tank contents | | |
| Total solids | 14.5 | |
| Total water | 132.0 | |
| Total to feed tank | 146.5 | |
| % Solids | 9.88% | |

This trial was performed using black liquor at a ratio of 13 kg of stock black liquor to 10 k g of mixed woody feedstocks db. Slurry contained mixed feedstocks to water at 8.1% db. Stock black liquor to mixed dry feedstocks ratio is 1.3:1 db.

TABLE 26

| Mass Balance (Mixed Kraft Feedstocks 20140731) | |
|---|---|
| Date | 2014 Jul. 31 |
| Feedstock | 6.4% hog fuel, 1.44% wood, 0.16% sludge |
| Liquid Catalyst | 1.3 kg stock black liquor per dry kg mix |
| T4 Injection time (mins) | 83 |
| Percent solids in Feed | 9.9% |
| Percent solids in reactors | 4.0% |
| Solids in feed (kg) | 5.0 |
| Solid product recovered (wet kg) | 1.134 |
| Moisture content of oil (%) | 12.9% |
| Bio crude recovered (dry kg) | 0.988 |
| Bio crude yield (dry) | 19.6% |
| NCG gas measured (m3/hr) | 0.47 |
| NCG density (kg/m3) | 1.60 |

TABLE 26-continued

| Mass Balance (Mixed Kraft Feedstocks 20140731) | |
|---|---|
| NCG (kg/hr) | 0.914 |
| Solids in feed (kg/hr) | 3.635 |
| NCG yield | 25.1% |
| Total feed to T4 - NCG (kg) | 124.4 |
| Ether extractable in liquor (%) | 1.440% |
| Ether extractable in liquor (kg) | 1.79 |
| Ether extractable yield | 35.6% |
| Solid residue in liquor (%) | 0.88% |
| Solid residue in liquor (kg) | 1.10 |
| Solid residue from catalyst (kg) | 0.00 |
| Solid residue in liquor yield | 21.8% |
| % black liquor solids in feed | 30.9% |
| % Inorganic material in feed | 15.9% |
| Organic material in feed (kg) | 422.8% |
| Methanol ethanol & acetone yield (kg) | 25.4% |
| Methanol, ethanol & acetone yield (%) | 5.04% |
| Yield Summary | |
| Bio crude yield (dry) | 19.6% |
| NCG yield | 25.1% |
| Ether extractable yield | 35.6% |
| Solid residue in liquor yield | 21.8% |
| Methanol, ethanol & acetone yield (%) | 5.0% |
| Total | 107.24% |
| Cooler inlet temp | 310 |
| Estimated mixinq (Reactor inlet) temp | 330 |

Gas Analysis (Mixed Kraft Feedstocks 20140731)

TABLE 27

Non Condensable Gas Analysis (Mixed Kraft Feedstocks 20140731)

| Methane | CO | Hydrogen | Ethylene | Ethane | Propylene | Propane | $CO_2$ | $H_2S$ |
|---|---|---|---|---|---|---|---|---|
| 4.79% | 0.04% | 9.74% | 0.28% | 0.77% | 1.46% | 0.41% | 82.3% | 0.17% |

Bio-Crude Analysis (Mixed Kraft Feedstocks 20140731)

Data presented in Table 28 below is from the mass balance run.

TABLE 28

Analysis of Rio-Crude Oil (Mixed Kraft Feedstocks 20140731)

| | Description | Mixed Feed + BL 2014 Jul. 31 |
|---|---|---|
| Proximate Analysis | Moisture (% wt ar) | 7.5 |
| | Ash (% wt db) | 2.6 |
| | Volatiles (% wt db) | 0.0 |
| | Fixed C. (% wt db) | 0.0 |

TABLE 28-continued

Analysis of Rio-Crude Oil (Mixed Kraft Feedstocks 20140731)

| Description | | Mixed Feed + BL 2014 Jul. 31 |
|---|---|---|
| Ultimate Analysis | GCV (% MJ/kg) | 33.0 |
| | Carbon (% wt db) | 79.2 |
| | Hydrogen (% wt db) | 6.36 |
| | Nitrogen (% wt db) | 0.38 |
| | Sulphur (% wt db) | 0.58 |
| | Oxygen (% wt db) | 10.18 |
| | Chlorine (%) | |
| | Molar H/C Ratio | |
| Ash Constituent (% oxide in ash) | SiO2 (% wt db) | 3.3 |
| | Al2O3 (% wt db) | 4.9 |
| | Fe2O3 (% wt db) | 6.6 |
| | TiO2 (% wt db) | 0.15 |
| | K2O (% wt db) | 0.72 |
| | MgO (% wt db) | 4.8 |
| | Na2O (% wt db) | 5.5 |
| | CaO (% wt db) | 42.1 |
| | SO3 (% wt db) | 20.6 |
| | P2O5 (% wt db) | 3.5 |
| | Mn3O4 (% wt db) | 0.3 |
| | SrO (% wt db) | 0.6 |
| | BaO (% wt db) | <0.1 |
| | ZnO (% wt db) | <0.1 |
| | CuO (% wt db) | 0.2 |
| | Cr2O3 (% wt db) | 1.7 |
| | Co3O4 (% wt db) | <0.1 |
| | NiO (% wt db) | <0.1 |
| | V2O5 (% wt db) | 0.5 |

The processing temperatures for the Mixed Kraft Feedstocks were held steady within (331-336° C.) were again steady and stabilised at 331° C. The ash content of the Bio-Crude Oil was about 2.6%, The Bio-Crude Oil has a gross calorific value of 33 MJ/kg, for comparison purposes diesel is around 45 MJ/kg.

Solvent Extraction of Bio-Crude (Mixed Kraft Feedstocks 20140731)

Extraction of the oil from Canfor Mixed Feedstocks process water with the solvent diethyl ether gave 35.6% extractables as a fraction of the feedstock (dry basis). Total oils recoverable (biocrude plus ether extractables) were 54.2% of the feed mass.

Mixed Kraft Feedstocks Hiatt Temperature 201407814
Operating Conditions (Mixed Kraft Feedstocks 20140814)

Table 29 below shows the operating conditions of the mass balance run on Mixed Kraft Feedstocks.

TABLE 29

Operating Conditions (Mixed Kraft Feedstocks 20140814)

| | |
|---|---|
| Reactor Temperature | 355 to 335° C. |
| Reactor Pressure | 238 to 250 bar |
| Reactor Residence Time | 25 minutes |

Mass Balance (Mixed Kraft Feedstocks 20140814)
The Mixed Kraft Feedstock mixture is composed from solids:

TABLE 30

Content (Mixed Kraft Feedstocks 20140814)

| | kg to feed tank | % of dry feed |
|---|---|---|
| Hog Fuel | 8.0 | 55.3% |
| Pine | 1.8 | 12.4% |
| Sludge | 0.2 | 1.4% |
| Black liquor solids | 4.5 | 30.9% |
| Black liquor water | 8.5 | |
| Water | 127 | |
| Total solids | 14.5 | |
| Total water | 135.5 | |
| Total to feed tank | 150.0 | |
| % Solids | 9.65% | |

TABLE 31

Mass Balance (Mixed Kraft Feedstocks 20140814)

| | |
|---|---|
| Date | 2014 Aug. 14 |
| Feedstock | 6.4% hog fuel, 1.44% wood, 0.16% sludge |
| Liquid Catalyst | 1.3 kg stock black liquor per dry kg mix |
| T4 Injection time (mins) | 61 |
| Percent solids in Feed | 9.7% |
| Percent solids in reactors | 3.5% |
| Solids in feed (kg) | 3.0 |
| Solid product recovered (wet kg) | 0.521 |
| Moisture content of oil (%) | 20.1% |
| Bio crude recovered (dry kg) | 0.416 |
| Bio crude yield (dry) | 13.7% |
| NCG gas measured (m3/hr) | 0.42 |
| NCG density (kg/m3) | 1.52 |
| NCG (kg/hr) | 0.784 |
| Solids in feed (kg/hr) | 2.990 |
| NCG yield | 26.2% |
| Total feed to T4 - NCG (kg) | 85.5 |
| Ether extractable in liquor (%) | 0.574% |
| Ether extractable in liquor (kg) | 0.49 |
| Ether extractable yield | 16.1% |
| Solid residue in liquor (%) | 0.66% |
| Solid residue in liquor (kg) | 0.56 |
| Solid residue from catalyst (kg) | 0.00 |
| Solid residue in liquor yield | 18.4% |
| % black liquor solids in feed | 30.9% |
| % Inorganic material in feed | 15.9% |
| Organic material in feed (kg) | 422.8% |
| Methanol ethanol & acetone yield (kg) | 25.4% |

TABLE 31-continued

Mass Balance (Mixed Kraft Feedstocks 20140814)

| | |
|---|---|
| Methanol, ethanol & acetone yield (%) | 5.04% |
| Yield Summary | |
| Bio crude yield (dry) | 13.7% |
| NCG yield | 26.2% |
| Ether extractable yield | 16.1% |
| Solid residue in liquor yield | 18.4% |
| Methanol, ethanol & acetone yield (%) | 5.0% |
| Total | 79.54% |
| Cooler inlet temp | 335 |
| Estimated mixing (Reactor inlet) temp | 355 |

The mass balance across the Cat-HTR reactor for the Mixed Kraft Feedstocks trial has significant mass missing. This behaviour might be explained by material retained within the internal pipes on the reactor and cooler.

Gas Analysis (Mixed Kraft Feedstocks 20140814)

TABLE 32

Non Condensable Gas Analysis (Mixed Kraft Feedstocks 20140814)

| Methane | CO | Hydrogen | Ethylene | Ethane | Propylene | Propane | $CO_2$ | $H_2S$ |
|---|---|---|---|---|---|---|---|---|
| 5.12% | 0.04% | 13.75% | 0.36% | 0.86% | 1.36% | 0.38% | 77.9% | 0.26% |

Bio-Crude Analysis (Mixed Kraft Feedstocks 20140814)

Data presented in Table 33 below is from a mass balance run.

TABLE 33

Analysis of Bio-Crude Oil (Mixed Kraft Feedstocks 20140814)

| Description | | Mixed Feed + BL 20140814 |
|---|---|---|
| Proximate Analysis | Moisture (% wt ar) | 4 |
| | Ash (% wt db) | 2.04 |
| | Volatiles (% wt db) | |
| | Fixed C. (% wt db) | |
| Ultimate Analysis | GCV (% MJ/kg) | 33.0 |
| | Carbon (% wt db) | 77.6 |
| | Hydrogen (% wt db) | 6.85 |
| | Nitrogen (% wt db) | 0.32 |
| | Sulphur (% wt db) | 0.57 |
| | Oxygen (% wt db) | 12.4 |
| | Chlorine (%) | |
| | Molar H/C Ratio | |
| Ash Constituent (% oxide in ash) | $SiO_2$ (% wt db) | 3.3 |
| | $Al_2O_3$ (% wt db) | 5 |
| | $Fe_2O_3$ (% wt db) | 5.1 |
| | $TiO_2$ (% wt db) | 0.21 |
| | $K_2O$ (% wt db) | 0.81 |
| | MgO (% wt db) | 4.8 |
| | $Na_2O$ (% wt db) | 6.7 |
| | CaO (% wt db) | 42.4 |
| | $SO_3$ (% wt db) | 19.9 |
| | $P_2O_5$ (% wt db) | 3.5 |
| | $Mn_3O_4$ (% wt db) | 0.3 |
| | SrO (% wt db) | 0.5 |
| | BaO (% wt db) | 0.1 |
| | ZnO (% wt db) | <0.1 |
| | CuO (% wt db) | 0.2 |
| | $Cr_2O_3$ (% wt db) | 2.3 |
| | $Co_3O_4$ (% wt db) | <0.1 |
| | NiO (% wt db) | <0.1 |
| | $V_2O_5$ (% wt db) | 0.6 |

The ash content of the Bio-Crude Oil was about 2%.

The Bio-Crude Oil has a gross calorific value of 33.7 MJ/kg dry basis

Solvent Extraction of Bio-Crude (Mixed Kraft Feedstocks 20140814)

Extraction of the oil from Canfor Mixed Feedstocks process water with the solvent diethyl ether gave 16.1% extractables as a fraction of the feedstock (dry basis). Taking the oil yield (bio-crude plus ether extractables) as 29.8%

Example 3: Discussion

Bio-Crude Quality

Bio-crude quality is most readily assessed in the first instance by means of its Gross Calorific Value (GCV). This is the gross energy contained in the material and is closely related to the oxygen and hydrogen content of the bio-crude. For Radiata pine wood flour with sodium hydroxide catalyst on the SPP, typical GCV of bio-crude is in the range 34-36 MJ/kg dry basis.

The Radiata pine wood flour bio-crude has a low ash content, and therefore dry basis values are similar to dry ash free basis (daf) values. The bio-crudes from hog fuel and black liquor feedstocks have significantly higher ash values, and it is more appropriate to compare these on a daf basis.

In FIG. 1 the GCV on a daf basis is plotted against oxygen content for Bio-crudes prepared in this project and for a historical series of Licella bio-crudes (dry basis) from Radiata Pine. The oxygen content is determined by difference from the ultimate analysis as [100−% C−% H−% S−% N]. As such it is subject to accumulation of systematic and random errors and consequently the error associated with these values is estimated as +/−1-2 percentage points.

The calorific values of the bio-crudes from this study lie in the range within, or very close to, the target band of 34-36 MJ/kg. Upon distillation, the bio-crude distillates can be expected to have an oxygen content close to 11%. The significance of the target is that commercial hydrotreating technologies exist for hydrodeoxygenation (HDO) of oils at around 11% oxygen. Licella's assessment is that the remaining oxygen in the bio-crudes is more efficiently removed by hydrotreating in conventional refinery processes than by other processes. These values demonstrate that the catalytic components in black liquor can effectively substitute for the basic catalyst sodium hydroxide in Cat-HTR applications. The other main heteroatoms present in the bio-crudes are Nitrogen and Sulphur. Both of these elements are higher in the bio-crudes derived from hog-fuel and black liquor than those derived from Radiata pine wood flour. Sulphur is unlikely to present an issue for further upgrading as oil refining processes are designed to accomplish desulphurization. The distribution and nature of the nitrogen content in the bio-crudes will need to be examined post-distillation to assess possible impact on downstream processing. Denitrification steps are well established in oil refining processes.

Aromatic Content

Bio-crudes from Radiata pine wood flour have about 50% of their carbon atoms in an aromatic environment by $^{13}$C NMR spectroscopy. While this does not mean that hydrodeoxygenated bio-crudes will contain 50% aromatics, it is indicative of a high potential to produce aromatic chemicals, for example by catalytic reforming. Bio-crudes based on high proportions of black liquor may be expected to have still higher aromatic contents, however this should be confirmed by testing.

This scenario is commercially interesting because of the increasing influence of shale oils in the US which are relatively low in fractions used to make aromatic chemicals.

Bio-Crude Yields

Bio-crude yields are generally consistent with other feedstocks processed using the SPP, as discussed in Section 9.0. The SPP uses a relatively large amount of supercritical steam to heat the biomass slurry to reaction temperature, and the consequent dilution favours dissolution of bio-crude into the water phase. This is a phenomenon that has been reported by other investigators, for example.

Example 4: Waste Water Sample Analysis

TABLE 34

| Mixed kraft feedstocks trial (20140814) water sample analysis | | |
|---|---|---|
| | | Our Reference |
| | UNITS | 114714-1 |
| | | Your Reference |
| | — | 1 |
| | | Type of Sample |
| VOCs in water | — | Water |
| Date extracted | — | 19 Aug. 2014 |
| Date analysed | — | 22 Aug. 2014 |
| Dichlorodifluoromethane | µg/L | <1,000 |
| Chloromethane | µg/L | <1,000 |
| Vinyl Chloride | µg/L | <1,000 |
| Bromomethane | µg/L | <1,000 |
| Chloroethane | µg/L | <1,000 |
| Trichlorofluoromethane | µg/L | <1,000 |
| 1,1-Dichloroethene | µg/L | <100 |
| Trans-1,2-dichloroethene | µg/L | <100 |
| 1,1-dichloroethene | µg/L | <100 |
| Cis-1,2-dichloroethene | µg/L | <100 |
| Bromochloromethane | µg/L | <100 |
| Chloroform | µg/L | <100 |
| 2,2-dichloropropane | µg/L | <100 |
| 1,2-dichloroethane | µg/L | <100 |
| 1,1,1-trichloroethane | µg/L | <100 |
| 1,1-dichloropropene | µg/L | <100 |
| Cyclohexane | µg/L | <100 |
| Carbon tetrachloride | µg/L | <100 |
| Benzene | µg/L | 180 |
| Dibromomethane | µg/L | <100 |
| 1,2-dichloropropane | µg/L | <100 |
| Trichloroethene | µg/L | <100 |
| Bromodichloromethane | µg/L | <100 |
| Trans-1,3-dichloropropene | µg/L | <100 |
| cis-1,3-dichloropropene | µg/L | <100 |

TABLE 34-continued

Mixed kraft feedstocks trial (20140814) water sample analysis

| | | |
|---|---|---|
| 1,1,2-trichloroethane | µg/L | <100 |
| Toluene | µg/L | 370 |
| 1,3-dichloropropane | µg/L | <100 |
| Dibromochloromethane | µg/L | <100 |
| 1,2-dibromoethane | µg/L | <100 |
| Tetrachloroethene | µg/L | <100 |
| 1,1,1,2-tetrachloroethane | µg/L | <100 |
| Chlorobenzene | µg/L | <100 |
| Ethylbenzene | µg/L | <100 |
| Bromoform | µg/L | <100 |
| m + p-xylene | µg/L | <200 |
| Styrene | µg/L | <100 |
| 1,1,2,2-tetracholorethane | µg/L | <100 |
| o-xylene | µg/L | <100 |
| 1,2,3-trichloropropane | µg/L | <100 |
| Isopropybenzene | µg/L | <100 |

| | UNITS | Our Reference |
|---|---|---|
| | | 114714-1 |
| | Your Reference | |
| | — | 1 |
| | Type of Sample | |
| VOCs in water | — | Water |
| Bromobenzene | µg/L | <100 |
| n-propy l benzene | µg/L | <100 |
| 2-chlorotoluene | µg/L | <100 |
| 4-chlorotoluene | µg/L | <100 |
| 1,3,5-trimethyl benzene | µg/L | <100 |
| Tert-butyl benzene | µg/L | <100 |
| 1,2,4-trimethyl benzene | µg/L | <100 |
| 1,3-dichlorobenzene | µg/L | <100 |
| Sec-butyl benzene | µg/L | <100 |
| 1,4-dichlorobenzene | µg/L | <100 |
| 4-isopropyl toluene | µg/L | <100 |
| 1,2-dichlorobenzene | µg/L | <100 |
| n.butyl benzene | µg/L | <100 |
| 1,2-dibromo-3-Chloropropane | µg/L | <100 |
| 1,2,4-trichlorobenzene | µg/L | <100 |
| Hexachlorobutadiene | µg/L | <100 |
| 1,2,3-trichlorobenzene | µg/L | <100 |
| Surrogate Dibromofluoromel | % | 100 |
| Surrogate toluene-d8 | % | 101 |
| Surrogate 4-BFB | % | 106 |

| | UNITS | Our Reference |
|---|---|---|
| | | 114714-1 |
| | Your Reference | |
| | — | 1 |
| | Type of Sample | |
| vTRH(C6-C10)/BTEXN in Water | — | Water |
| Date extracted | — | 19 Aug. 2014 |
| Date analysed | — | 22 Aug. 2014 |
| $TRHC_6$-$C_9$ | µg/L | 31,000 |
| $TRHC_8$-$C_{10}$ | µg/L | 34,000 |
| $TRHC_6$-$C_{10}$ less BTEX (F1) | µg/L | 33,000 |
| Benzene | µg/L | 180 |
| Toluene | µg/L | 370 |
| Ethylbenzene | µg/L | <100 |
| m + p-xylene | µg/L | <200 |
| o-xylene | µg/L | <100 |
| Naphthalene | µg/L | <100 |
| Surrogate Dibromofluoromethane | % | 100 |
| Surrogate toluene-d8 | % | 101 |
| Surrogate 4-BFB | % | 106 |

TABLE 34-continued

Mixed kraft feedstocks trial (20140814) water sample analysis

| | UNITS | Our Reference | 114714-1 |
|---|---|---|---|
| | | Your Reference | |
| | — | Type of Sample | 1 |
| svTRH(C10-C40) in Water | — | | Water |
| Date extracted | — | | 18 Aug. 2014 |
| Date analysed | — | | 18 Aug. 2014 |
| TRHCio-C14 | µg/L | | 650,000 |
| TRHC15-C213 | µg/L | | 490,000 |
| TRHC2o-Cae | µg/L | | 14,000 |
| TRHCID-Cis | µg/L | | 800,000 |
| TRH > Cio-Cle less | µg/L | | 800,000 |
| Naphthalene (F2) | | | 180,000 |
| TRH > Cia-C34 | µg/L | | 1,800 |
| TRH > C34-Cso | µg/L | | |
| Surrogate o-Terphenyl | % | | |

| | UNITS | Our Reference | 114714-1 |
|---|---|---|---|
| | | Your Reference | |
| | — | Type of Sample | 1 |
| HM in water-total | — | | Water |
| Date prepared | — | | 18 Aug. 2014 |
| Date analysed | — | | 18 Aug. 2014 |
| Arsenic-Total | µg/L | | 45 |
| Cadmium-Total | µg/L | | <0.1 |
| Chromium-Total | µg/L | | 1 |
| Cooper-Total | µg/L | | <1 |
| Lead-Total | µg/L | | <1 |
| Mercury-Total | µg/L | | 0.30 |
| Nickel-Total | µg/L | | <1 |
| Zinc-Total | µg/L | | 44 |

| | UNITS | Our Reference | 114714-1 |
|---|---|---|---|
| | | Your Reference | |
| | — | Type of Sample | 1 |
| Metals in Waters-Acid extractable | — | | Water |
| Date prepared | — | | 18 Aug. 2014 |
| Date analysed | — | | 18 Aug. 2014 |
| Sulfur-Total | mg/L | | 840 |

| | UNITS | Our Reference | 114714-1 |
|---|---|---|---|
| | | Your Reference | |
| | — | Type of Sample | 1 |
| Miscellaneous Inorganics | — | | Water |
| Date prepared | — | | 15 Aug. 2014 |
| Date analysed | — | | 15 Aug. 2014 |
| pH | pH Units | | 7.0 |
| Total Dissolved Solids (gray) | mg/L | | 15,000 |
| BOD | mg/L | | 600 |
| COD | mgO$_2$/L | | 19,000 |
| Total Organic Carbon | mg/L | | 5,900 |

TABLE 34-continued

Mixed kraft feedstocks trial (20140814) water sample analysis

|  | UNITS | Our Reference |
|---|---|---|
|  |  | 114714-1 |
|  |  | Your Reference |
|  | — | 1 |
|  |  | Type of Sample |
| Cations in water-Total | — | Water |
| Date digested | — | 18 Aug. 2014 |
| Date analysed | — | 18 Aug. 2014 |
| Sodium-Total | mg/L | 2,300 |
| Potassium-Total | mg/L | 190 |
| Calcium-Total | mg/L | 16 |
| Magnesium-Total | mg/L | 3.4 |

| Method ID | Methodology Summary |
|---|---|
| Org-013 | Water samples are analysed directly by purge and trap GC-MS. |
| Org-016 | Soil samples are extracted with methanol and spiked into water prior to analysing by purge and trap GC-MS. Water samples are analysed directly by purge and trap GC-MS. F1-(C6-C10)-BTEX as per NEPM Bl. Guideline on Investigation Levels for Soil and Groundwater. |
| Org-003 | Soil samples are extracted with Dichloromethane/Acetone and waters with Dichloromethane and analysed by GC-FD. F2 = (>C10-C16)-Naphthalene as per NEPM B1 Guideline on Investigation Levels for Soil and Groundwater (HSLs Tables 1A (3,4)). Note Naphthalene is determined from the VOC analysis. |
| Metals-022ICP-MS | Determination of various metals by ICP-MS. |
| Metals-021 CV-AAS | Determination of mercury by Cold Vapour AAS |
| Metals-020 ICP-AES | Determination of various metals by ICP-AES. |
| Inorg-001 | pH-Measured using pH meter and electrode in accordance with APHA 22nd ED, 4500-H$^+$. Please note that the results for water analyses are indicative only, as analysis outside of the APHA storage times. |
| Inorg-018 | Total Dissolved Solids-determined gravimetrically. The solids are dried at 180+/−50° C. |
| Inorg-091 | BOD-Analysed in accordance with APHA 22nd ED 5210 D and in house INORG-091. |
| Inorg-067 | Samples are digested in acid with a known excess of potassium dichromate then titrated against ammonium ferrous sulphate in accordance with APHA 22nd ED 5310 B. |
| Inorg-079 | TOC determined using a TOC analyser using the combustion method. DOC is filtered prior to determination. Analysis using APHA 22nd ED 5310 B. |

| QUALITY CONTROL VOCs in water | UNITS | POL | METHOD | Blank | Duplicate SnW | Duplicate results Base II Duplicate II % RPD | Spike SnW | Spike % Recovery |
|---|---|---|---|---|---|---|---|---|
| Date extracted | — |  |  | 19 Aug. 2014 |  |  | LCS-W1 | 19 Aug. 2014 |
| Date analysed | — |  |  | 22 Aug. 2014 |  |  | LCS-W1 | 22 Aug. 2014 |
| Dichlorofluoromethane | μg/L | 10 | Org-013 | <10 | [NT] | [NT] | [NR] | [NR] |
| Chloromethane | μg/L | 10 | Org-013 | <10 | [NT] | [NT] | [NR] | [NR] |
| Vinyl Chloride | μg/L | 10 | Org-013 | <10 | [NT] | [NT] | [NR] | [NR] |
| Bromomethane | μg/L | 10 | Org-013 | <10 | [NT] | [NT] | [NR] | [NR] |
| Chloroethane | μg/L | 10 | Org-013 | <10 | [NT] | [NT] | [NR] | [NR] |
| Trichlorofluoromethane | μg/L | 10 | Org-013 | <10 | [NT] | [NT] | [NR] | [NR] |
| 1,1-Dichloroethane | μg/L | 1 | Org-013 | <1 | [NT] | [NT] | [NR] | [NR] |
| Trans-1,2-dichloroethane | μg/L | 1 | Org-013 | <1 | [NT] | [NT] | [NR] | [NR] |
| 1,1-dichloroethane | μg/L | 1 | Org-013 | <1 | [NT] | [NT] | LCS-W1 | 99% |
| Cis-1,2-dichloroethane | μg/L | 1 | Org-013 | <1 | [NT] | [NT] | [NR] | [NR] |
| Bromochloromethane | μg/L | 1 | Org-013 | <1 | [NT] | [NT] | [NR] | [NR] |
| Chloroform | μg/L | 1 | Org-013 | <1 | [NT] | [NT] | LCS-W1 | 95% |
| 2,2-dichloropropane | μg/L | 1 | Org-013 | <1 | [NT] | [NT] | [NR] | [NR] |
| 1,2-dichloroethane | μg/L | 1 | Org-013 | <1 | [NT] | [NT] | LCS-W1 | 94% |
| 1,1,1-trichloroethane | μg/L | 1 | Org-013 | <1 | [NT] | [NT] | LCS-W1 | 96% |
| 1,1-dichloropropene | μg/L | 1 | Org-013 | <1 | [NT] | [NT] | [NR] | [NR] |
| Cyclohexane | μg/L | 1 | Org-013 | <1 | [NT] | [NT] | [NR] | [NR] |
| Carbon tetrachloride | μg/L | 1 | Org-013 | <1 | [NT] | [NT] | [NR] | [NR] |
| Benzene | μg/L | 1 | Org-013 | <1 | [NT] | [NT] | [NR] | [NR] |
| Dibromomethane | μg/L | 1 | Org-013 | <1 | [NT] | [NT] | [NR] | [NR] |
| 1,2-dichloropropane | μg/L | 1 | Org-013 | <1 | [NT] | [NT] | [NR] | [NR] |
| Trichloroethane | μg/L | 1 | Org-013 | <1 | [NT] | [NT] | LCS-W1 | 92% |
| Bromodichloromethane | μg/L | 1 | Org-013 | <1 | [NT] | [NT] | LCS-W1 | 96% |
| Trans-1,3-dichloropropene | μg/L | 1 | Org-013 | <1 | [NT] | [NT] | [NR] | [NR] |
| cis-1,3-dichloropropene | μg/L | 1 | Org-013 | <1 | [NT] | [NT] | [NR] | [NR] |
| 1,1,2-trichloroethane | μg/L | 1 | Org-013 | <1 | [NT] | [NT] | [NR] | [NR] |
| Toluene | μg/L | 1 | Org-013 | <1 | [NT] | [NT] | [NR] | [NR] |
| 1,3-dichloropropane | μg/L | 1 | Org-013 | <1 | [NT] | [NT] | [NR] | [NR] |
| Dibromochloromethane | μg/L | 1 | Org-013 | <1 | [NT] | [NT] | LCS-W1 | 95% |

TABLE 34-continued

Mixed kraft feedstocks trial (20140814) water sample analysis

| | | | | | | | |
|---|---|---|---|---|---|---|---|
| 1,2-dibromoethane | μg/L | 1 | Org-013 | <1 | [NT] | [NT] | [NR] | [NR] |
| Tetrachloroethane | μg/L | 1 | Org-013 | <1 | [NT] | [NT] | LCS-W1 | 101% |
| 1,1,1,2-tetrachloroethane | μg/L | 1 | Org-013 | <1 | [NT] | [NT] | [NR] | [NR] |
| Chlorobenzene | μg/L | 1 | Org-013 | <1 | [NT] | [NT] | [NR] | [NR] |
| Ethylbenzene | μg/L | 1 | Org-013 | <1 | [NT] | [NT] | [NR] | [NR] |
| Bromoform | μg/L | 1 | Org-013 | <1 | [NT] | [NT] | [NR] | [NR] |
| m + p-xylene | μg/L | 2 | Org-013 | <2 | [NT] | [NT] | [NR] | [NR] |
| Styrene | μg/L | 1 | Org-013 | <1 | [NT] | [NT] | [NR] | [NR] |
| 1,1,2,2-tetrachloroethane | μg/L | 1 | Org-013 | <1 | [NT] | [NT] | [NR] | [NR] |
| o-xylene | μg/L | 1 | Org-013 | <1 | [NT] | [NT] | [NR] | [NR] |
| 1,2,3-trichloropropane | μg/L | 1 | Org-013 | <1 | [NT] | [NT] | [NR] | [NR] |
| Isopropylbenzene | μg/L | 1 | Org-013 | <1 | [NT] | [NT] | [NR] | [NR] |
| Bromobenzene | μg/L | 1 | Org-013 | <1 | [NT] | [NT] | [NR] | [NR] |
| n-propyl benzene | μg/L | 1 | Org-013 | <1 | [NT] | [NT] | [NR] | [NR] |
| 2-chlorotoluene | μg/L | 1 | Org-013 | <1 | [NT] | [NT] | [NR] | [NR] |
| 4-chlorotoluene | μg/L | 1 | Org-013 | <1 | [NT] | [NT] | [NR] | [NR] |
| 1,3,5-trimethylbenzene | μg/L | 1 | Org-013 | <1 | [NT] | [NT] | [NR] | [NR] |
| Tert-butylbenzene | μg/L | 1 | Org-013 | <1 | [NT] | [NT] | [NR] | [NR] |
| 1,2,4-trimethylbenzene | μg/L | 1 | Org-013 | <1 | [NT] | [NT] | [NR] | [NR] |
| 1,3-dichlorobenzene | μg/L | 1 | Org-013 | <1 | [NT] | [NT] | [NR] | [NR] |
| Sec-butyl benzene | μg/L | 1 | Org-013 | <1 | [NT] | [NT] | [NR] | [NR] |
| 1,4-dichlorobenzene | μg/L | 1 | Org-013 | <1 | [NT] | [NT] | [NR] | [NR] |
| 4-isopropyl toluene | μg/L | 1 | Org-013 | <1 | [NT] | [NT] | [NR] | [NR] |
| 1,2-dichlorobenzene | μg/L | 1 | Org-013 | <1 | [NT] | [NT] | [NR] | [NR] |
| n-butyl benzene | μg/L | 1 | Org-013 | <1 | [NT] | [NT] | [NR] | [NR] |
| 1,2-dibromo-3-chloropropane | μg/L | 1 | Org-013 | <1 | [NT] | [NT] | [NR] | [NR] |
| 1,2,4-trichlorobenzene | μg/L | 1 | Org-013 | <1 | [NT] | [NT] | [NR] | [NR] |
| Hexachlorobutadene | μg/L | 1 | Org-013 | <1 | [NT] | [NT] | [NR] | [NR] |
| 1,2,3-trichlorobenzene | μg/L | 1 | Org-013 | <1 | [NT] | [NT] | [NR] | [NR] |
| Surrogate Dibromofluoromethane | % | | Org-013 | 100 | [NT] | [NT] | LCS-W1 | 99% |
| Surrogate toluene = d8 | % | | Org-013 | 99 | [NT] | [NT] | LCS-W1 | 98% |
| Surrogate 4-BFB | % | | Org-013 | 104 | [NT] | [NT] | LCS-W1 | 101% |

| QUALITY CONTROL vTRH(C6-C10/BTEXN in water | UNITS | POL | METHOD | Blank | Duplicate SnW | Duplicate results Base II Duplicate II % RPD | Spike SnW | Spike % Recovery |
|---|---|---|---|---|---|---|---|---|
| Date extracted | — | | | 19 Aug. 2014 | [NT] | [N1] | LCS-W1 | 18 Aug. 2014 |
| Date analysed | — | | | 22 Aug. 2014 | [NT] | [NT] | LCS-W1 | 22 Aug. 2014 |
| TRH $C_6$-$C_9$ | μg/L | 10 | Org-016 | <10 | [NT] | [NT] | LCS-W1 | 107% |
| TRH $C_6$-$C_{10}$ | μg/L | 10 | Org-016 | <10 | [NT] | [NT] | LCS-W1 | 107% |
| Benzene | μg/L | 1 | Org-016 | <1 | [NT] | [NT] | LCS-W1 | 104% |
| Toluene | μg/L | 1 | Org-016 | <1 | [NT] | [NT] | LCS-W1 | 107% |
| Ethylbenzene | μg/L | 1 | Org-016 | <1 | [NT] | [NT] | LCS-W1 | 107% |
| m+p-xylene | μg/L | 2 | Org-016 | <2 | [NT] | [NT] | LCS-W1 | 109% |
| o-xylene | μg/L | 1 | Org-016 | <1 | [NT] | [NT] | LCS-W1 | 110% |
| Naphthalene | μg/L | 1 | Org-013 | <1 | [NT] | [NT] | [NR] | [NR] |
| Surrogate Dibromofluoromethane | % | | Org-016 | 100 | [NT] | [NT] | LCS-W1 | 99% |
| Surrogate toluene = d8 | % | | Org-016 | 99 | [NT] | [NT] | LCS-W1 | 99% |
| Surrogate 4-BFB | % | | Org-016 | 104 | [NT] | [NT] | LCS-W1 | 100% |

| QUALITY CONTROL svTRH(C6-C40/BTEXN in water | UNITS | POL | METHOD | Blank | Duplicate SnW | Duplicate results Base II Duplicate II % RPD | Spike SnW | Spike % Recovery |
|---|---|---|---|---|---|---|---|---|
| Date extracted | — | | | 18 Aug. 2014 | [NT] | [NT] | LCS-W2 | 18 Aug. 2014 |
| Date analysed | — | | | 18 Aug. 2014 | [NT] | [NT] | LCS-W2 | 18 Aug. 2014 |
| TRH $C_{10}$-$C_{14}$ | μg/L | 50 | Org-003 | <50 | [NT] | [NT] | LCS-W2 | 88% |
| TRH $C_{15}$-$C_{28}$ | μg/L | 100 | Org-003 | <100 | [NT] | [NT] | LCS-W2 | 85% |
| TRH $C_{29}$-$C_{36}$ | μg/L | 100 | Org-003 | <100 | [NT] | [NIT] | LCS-W2 | 84% |
| TRH >$C_{10}$-$C_{16}$ | μg/L | 50 | Org-003 | <50 | [NT] | [NT] | LCS-W2 | 83% |
| TRH >$C_{16}$-$C_{34}$ | μg/L | 100 | Org-003 | <100 | [NT] | [NT] | LCS-W2 | 86% |
| TRH >$C_{34}$-$C_{40}$ | μg/L | 100 | Org-003 | <100 | [NT] | [NT] | LCS-W2 | 84% |
| Surrogate o-Terphenyl | % | | Org-003 | 90 | [NT] | [NT] | LCS-W2 | 71% |

TABLE 34-continued

Mixed kraft feedstocks trial (20140814) water sample analysis

| QUALITY CONTROL HM in water-total | UNITS | POL | METHOD | Blank | Duplicate SnW | Duplicate Results Base II Duplicate II % RPD | Spike SnW | Spike % Recovery |
|---|---|---|---|---|---|---|---|---|
| Date prepared | — | | | 18 Aug. 2014 | [NT] | [NT] | LCS-W2 | 18 Aug. 2014 |
| Date analysed | — | | | 18 Aug. 2014 | | | | |
| Arsenic-Total | μg/L | 1 | Metals-022 ICP-MS | <1 | [NT] | [NT] | LCS-W2 | 106% |
| Cadmium-Total | μg/L | 0.1 | Metals-022 ICP-MS | <0.1 | [NT] | [NT] | LCS-W2 | 119% |
| Chromium-Total | μg/L | 1 | Metals-022 ICP-MS | <1 | [NT] | [NT] | LCS-W2 | 110% |
| Copper-Total | μg/L | 1 | Metals-022 ICP-MS | <1 | [NT] | [NT] | LCS-W2 | 91% |
| Lead-Total | μg/L | 1 | Metals-022 ICP-MS | <1 | [NT] | [NT] | LCS-W2 | 117% |
| Mercury-Total | μg/L | 0.05 | Metals-021 CV-AAS | <0.05 | [NT] | [NT] | LCS-W2 | 96% |
| Nickel-Total | μg/L | 1 | Metals-022 ICP-MS | <1 | [NT] | [NT] | LCS-W2 | 103% |
| Zinc-Total | μg/L | 1 | Metals-022 ICP-MS | <1 | [NT] | [NT] | LCS-W2 | 109% |

| QUALITY CONTROL Metals in Waters-Acid extractable | UNITS | POL | METHOD | Blank | Duplicate SnW | Duplicate results Base II Duplicate II % RPD | Spike SnW | Spike % Recovery |
|---|---|---|---|---|---|---|---|---|
| Date prepared | — | | | 18 Aug. 2014 | [NT] | [NT] | LCS-W1 | 18 Aug. 2014 |
| Date analysed | — | | | 18 Aug. 2014 | [NT] | [NT] | LCS-W1 | 19 Aug. 2014 |
| Sulphur-Total | mg/L | 0.5 | Metals-020 ICP-AES | 93 | [NT] | [NT] | LCS-W1 | 93% |

| QUALITY CONTROL Miscellaneous Inorganics | UNITS | POL | METHOD | Blank | Duplicate SnW | Duplicate results Base II Duplicate II % RPD | Spike SnW | Spike % Recovery |
|---|---|---|---|---|---|---|---|---|
| Date prepared | — | | | 15 Aug. 2014 | 114714-1 | 15 Aug. 2014 II | LCS-W1 | 15 Aug. 2014 |
| Date analysed | — | | | 15 Aug. 2014 | 114714-1 | 15 Aug. 2014 | LCS-W1 | 15 Aug. 2014 |
| pH | pH Units | | Inorg-001 | [NT] | 114714-1 | 15 Aug. 2014 II | LCS-W1 | 101% |
| Total Dissolved Solids (gray) | mg/L mg/L | 5 | Inorg-018 | <5 | 114714-1 | 15 Aug. 2014 7.0 II [NT] 15000 II | LCS-W1 | 95% |
| BOD | mg | 5 | Inorg-091 | <5 | 114714-1 | [NT] | LCS-W1 | 84% |
| COD | O2/L | 50 | Inorg-067 | <50 | 114714-1 | 600 II [NT] | LCS-W1 | 84% |
| Total Organic Carbon | mg/L | 1 | Inorg-079 | <1 | 114714-1 | 19000 II 19000 II RPD: 0 5900 II 5800 II RPD: 2 | LCS-W1 | 104% |

| QUALITY CONTROL Cations in water-Total | UNITS | POL | METHOD | Blank | Duplicate SnW | Duplicate results Base II Duplicate II % RPD | Spike SnW | Spike % Recovery |
|---|---|---|---|---|---|---|---|---|
| Date digested | — | | | 18 Aug. 2014 | [NT] | [NT] | LCS-W1 | 18 Aug. 2014 |
| Date analysed | — | | | 18 Aug. 2014 | [NT] | [NT] | LCS-W1 | 18 Aug. 2014 |
| Sodium-Total | mg/L | 0.5 | Metals-020 ICP-AES | <0.5 | [NT] | [NT] | LCS-W1 | 102% |
| Potassium-Total | mg/L | 0.5 | Metals-020 ICP-AES | <0.5 | [NT] | [NT] | LCS-W1 | 97% |
| Calcium-Total | mg/L | 0.5 | Metals-020 ICP-AES | <0.5 | [NT] | [NT] | LCS-W1 | 104% |
| Magnesium-Total | mg/L | 0.5 | Metals-020 ICP-AES | <0.5 | [NT] | [NT] | LCS-W1 | 108% |

TABLE 35

Water Analysis (Radiata Pine Wood Flour w/-Black Liquor 20140523)
Water sample Cat. 1-ITR Trials, data from separate Erly.lrolab Services. reports

| | | Mixed Feedstocks 20140814 | Hog Fuel Sodium Hydroxide 20140716 | Pyrolysed Paper Sludge Black Liquor 2014052g | Radiata Black Liquor 20140523 |
|---|---|---|---|---|---|
| | | \multicolumn{4}{c|}{Our Reference:} | | | |
| | | 114714-1 | 113424-1 | 110678-1 | 110463-1 |
| | | \multicolumn{4}{c|}{Your Reference} | | | |
| | | 20140814 | 20140716 | 20140528 | 20140523 |
| | | \multicolumn{4}{c|}{Type of sample} | | | |
| | | Water | Water | Water | Water |
| | | \multicolumn{4}{c|}{date extracted} | | | |
| | | 19 Aug. 2014 | 23 Jul. 2014 | 29 May 2014 | 28 May 2014 |
| | | \multicolumn{4}{c|}{date analysed} | | | |
| VOCs in water | Units | 22 Aug. 2014 | 23 Jul. 2014 | 30 May 2014 | 29 May 2014 |
| Dichlorodifluoromethane | µg/L | <1,000 | <1,000 | <5,000 | <1,000 |
| Chloromethane | µg/L | <1,000 | <1,000 | <5,000 | <1,000 |
| Vinyl Chloride | µg/L | <1,000 | <1,000 | <5,000 | <1,000 |
| Bromomethane | µg/L | <1,000 | <1,000 | <5,000 | <1,000 |
| Chloroethane | µg/L | <1,000 | <1,000 | <5,000 | <1,000 |
| Trichlorofluoromethane | µg/L | <1000 | <1,000 | <5,000 | <1,000 |
| 1,1-Dichloroethene | µg/L | <100 | <100 | <500 | <100 |
| Trans-1,2-dichloroethene | µg/L | <100 | <100 | <500 | <100 |
| 1,1-dichloroethane | µg/L | <100 | <100 | <500 | <100 |
| Cis-1,2-dichloroethene | µg/L | <100 | <100 | <500 | <100 |
| Bromochloromethane | µg/L | <100 | <100 | <500 | <100 |
| Chloroform | µg/L | <100 | <100 | <500 | <100 |
| 2,2-dichioropropane | µg/L | <100 | <100 | <500 | <100 |
| 1,2-dichloroethane | µg/L | <100 | <100 | <500 | <100 |
| 1,1,1-trichloroethane | µg/L | <100 | <100 | <500 | <100 |
| 1,1-dichloropropene | µg/L | <100 | <100 | <500 | <100 |
| Cyclohexane | µg/L | <100 | <100 | <500 | <100 |
| Carbon tetrachloride | µg/L | <100 | <100 | <500 | <100 |
| Benzene | µg/L | <180 | 340 | <500 | 340 |
| Dibromomethane | µg/L | <100 | <100 | <500 | <100 |
| 1,2-dichloropropane | µg/L | <100 | <100 | <500 | <100 |
| Trichloroethene | µg/L | <MO | <100 | <500 | <100 |
| Bromodichloromethane | µg/L | <100 | <100 | <500 | <100 |
| Trans-1,3-dichloropropene | µg/L | <100 | <100 | <500 | <100 |
| cis-1,3-dichloropropene | µg/L | <100 | <100 | <500 | <100 |
| 1,1,2-trichioroethane | µg/L | <100 | <100 | <500 | <100 |
| Toluene | µg/L | 370 | 890 | 810 | 680 |
| 1,3-dichloropropane | µg/L | <100 | <100 | <500 | <100 |
| Dibromochloromethane | µg/L | <100 | <100 | <500 | <100 |
| 1,2-dibromoethane | µg/L | <100 | <100 | <500 | <100 |
| Tetrachloroethene | µg/L | <100 | <100 | <500 | <100 |
| 1,1,1,2-tetrachloroethane | µg/L | <100 | <100 | <500 | <100 |
| Chlorobenzene | µg/L | <100 | <100 | <500 | <100 |
| Ethylbenzene | µg/L | <100 | <120 | <500 | <130 |
| Bromoform | µg/L | <100 | <100 | <500 | <100 |
| m + p-xylene | µg/L | 200 | <200 | <1000 | <200 |
| Styrene | µg/L | <100 | <100 | <500 | <100 |
| 1,1,2,2-tetracholrethane | µg/L | <100 | <100 | <500 | <100 |
| o-xylene | µg/L | <100 | <120 | <500 | <100 |
| 1,2,3-trichloropropane | µg/L | <100 | <100 | <500 | <100 |
| Isopropybenzene | µg/L | <100 | <100 | <500 | <100 |
| | | \multicolumn{4}{c|}{Our Reference:} | | | |
| | | 114714-1 | 113424-1 | 110678-1 | 110463-1 |
| | | \multicolumn{4}{c|}{Your Reference} | | | |
| | | 20148014 | 20140716 | 20140528 | 20140523 |
| | | \multicolumn{4}{c|}{Type of sample} | | | |
| VOCs in water | | Water | Water | Water | Water |
| Bromobenzene | µg/L | <100 | <100 | <500 | <100 |
| n-propyl I benzene | µg/L | <100 | <100 | <500 | <100 |
| 2-chlorotoluene | µg/L | <100 | <100 | <500 | <100 |
| 4-chlonloluene | µg/L | <100 | <100 | <500 | <100 |

TABLE 35-continued

Water Analysis (Radiata Pine Wood Flour w/-Black Liquor 20140523)
Water sample Cat. 1-ITR Trials, data from separate Erly.lrolab Services. reports

| | | | | | |
|---|---|---|---|---|---|
| 1,3,5-trimethyl benzene | µg/L | <100 | <100 | <500 | <100 |
| Tert-butyl benzene | µg/L | <100 | <100 | <500 | <100 |
| 1,2,4-trimethyl benzene | µg/L | <100 | <100 | <500 | <100 |
| 1,3-dichlorobenzene | µg/L | <100 | <100 | <500 | <100 |
| Sec-butyl benzene | µg/L | <100 | <100 | <500 | <100 |
| 1,4-dichlorobenzene | µg/L | <100 | <100 | <500 | <100 |
| 4-isopropyl toluene | µg/L | <100 | <100 | <500 | <100 |
| 1,2-dichlorobenzene | µg/L | <100 | <100 | <500 | <100 |
| n.butyl benzene | µg/L | <100 | <100 | <500 | <100 |
| 1,2-dibromo-3-chloropropane | µg/L | <100 | <100 | <500 | <100 |
| 1,2,4-trichlorobenzene | µg/L | <100 | <100 | <500 | <100 |
| Hexachlorobutadiene | µg/L | <100 | <100 | <500 | <100 |
| 1,2,3-trichlorobenzene | µg/L | <100 | <100 | <500 | <100 |
| Surrogate Dibromofluoromel | µg/L | 100% | 106% | 112% | 105% |
| Surrogate toluene-d8 | µg/L | 101% | 105% | 100% | 100% |
| Suncgate4-BFB | µg/L | 106% | 95% | 100% | 99% |

| | | Mixed Feedstocks 20140814 | Hog Fuel Sodium Hydroxide 20140716 | Pyrolysed Paper Sludge Black Liquor 20140528 | Radiata Black Liquor 20140523 |
|---|---|---|---|---|---|
| | Our Reference: | 114714-1 | 113424-1 | 110678-1 | 110463-1 |
| | Your Reference | 20140814 | 20140716 | 20140528 | 20140523 |
| | Type of sample | Water | Water | Water | Water |
| | Date extracted | 19 Aug. 2014 | 23 Jul. 2014 | 29 May 2014 | 28 May 2014 |
| vTRH(C6-C10)/BTEXN in Water | Units / Date analysed | 22 Aug. 2014 | 23 Jul. 2014 | 30 May 2014 | 29 May 2014 |
| TRH C6-C9 | µg/L | 31,000 | 42,000 | 26,000 | 33,000 |
| TRH C6-C10 | µg/L | 34,000 | 50,000 | 27,000 | 36,000 |
| TRH C6-C10 less BTEX (F1) | µg/L | 33,000 | 49,000 | 26,000 | 35,000 |
| Benzene | µg/L | 180 | 430 | <500 | 340 |
| Toluene | µg/L | 370 | 890 | 810 | 680 |
| Ethylbenzene | µg/L | <100 | 120 | <500 | 130 |
| m + p-xylene | µg/L | <200 | <200 | <1000 | <200 |
| o-xylene | µg/L | <100 | 120 | <500 | <100 |
| Naphthalene | µg/L | <100 | <100 | <501 | <100 |
| Surrogate Dibromofluoromethane | µg/L | 100% | 106% | 112% | 105% |
| Surrogate toluene-d8 | µg/L | 101% | 105% | 100% | 100% |
| Surrogate 4-BFB | µg/L | 106% | 95% | 100% | 99% |

| | | | Our Reference: | | |
|---|---|---|---|---|---|
| | | 114714-1 | 113424-1 | Water 110678-1 | 110463-1 |
| | Your Reference | 20140814 | 20140716 | 20140528 | 20140523 |
| | Type of sample | Water | Water | Water | Water |
| | Date extracted | 18 Aug. 2014 | 24 Jul. 2014 | 30 May 2014 | 28 May 2014 |
| svTRH (C10-C40) in Water | Date analysed | 19 Aug. 2014 | 24 Jul. 2014 | 31 May 2014 | 29 May 2014 |
| TRH C10-C14 | µg/L | 650,000 | 430,000 | 25,000 | 860,000 |
| TRH C15-C26 | µg/L | 490.000 | 190000 | 160,000 | 510,000 |
| TRH C29-C36 | µg/L | 14,000 | 6,600 | 16,000 | 18,000 |
| TRH >C10-C16 | µg/L | 800,000 | 450,000 | 260,000 | 860,000 |
| TRH >C10-C16 less Naphthalene | (F2) | 800,000 | 450,000 | 260,000 | 860,000 |
| TRH >C16-C34 | µg/L | 180,000 | 91,000 | 120,000 | 260,000 |
| TRH >C34-C40 | µg/L | 1,800 | <1,000 | 4,800 | 5,300 |
| Surrogate o-Terphenyl | % | # | # | # | # |

TABLE 35-continued

Water Analysis (Radiata Pine Wood Flour w/-Black Liquor 20140523)
Water sample Cat. 1-ITR Trials, data from separate Erly.lrolab Services. reports

|  |  | Our Reference: | | | |
|---|---|---|---|---|---|
|  |  | 114714-1 | 113424-1 | 110678-1 | 110463-1 |
|  |  | | Your Reference | | |
|  |  | 20140814 | 20140716 | 20140528 | 20140523 |
|  |  | | Type of sample | | |
|  |  | Water | Water | Water | Water |
|  |  | | Date prepared | | |
|  |  | 18 Aug. 2014 | 23 Jul. 2014 | 30 May 2014 | 27 May 2014 |
|  |  | | Date analysed | | |
| HM in water-total |  | 18 Aug. 2014 | 23 Jul. 2014 | 30 May 2014 | 27 May 2014 |
| Arsenic-Total | µg/L | 45 | 2 | 29 | 27 |
| Cadmium-Total | µg/L | 0.1 | <01 | 5.7 | <0.1 |
| Chromium-Total | µg/L | 1 | 1 | 110 | <1 |
| Copper-Total | µg/L | 1 | <1 | 180 | 1 |
| Lead-Total | µg/L | 1 | <1 | 40 | <1 |
| Mercury-Total | µg/L | 0.3 | 0.06 | 1 | 0.58 |
| Nickel-Total | µg/L | 1 | <1 | 97 | <1 |
| Zinc-Total | µg/L | 44 | 8 | 1,100 | 14 |
|  |  | Our Reference: | | | |
|  |  | 114714-1 | 113424-1 | 110678-1 | 110463-1 |
|  |  | | Your Reference | | |
|  |  | 20140814 | 20140715 | 20140528 | 20140523 |
|  |  | | Type of sample | | |
|  |  | Water | Water | Water | Water |
|  |  | | Date prepared | | |
|  |  | 18 Aug. 2014 | 23 Jul. 2014 | 30 May 2014 | 27 May 2014 |
|  |  | | Date analysed | | |
| Metals in Waters-Acid extractable |  | 18 Aug. 2014 | 23 Jul. 2014 | 30 May 2014 | 27 May 2014 |
| Sulfur-Total | mg/L | 840 | 6.3 | 26 | 150 |
|  |  | Our Reference: | | | |
|  |  | 114114-1 | 113424-1 | 110678-1 | 110463-1 |
|  |  | | Your Reference | | |
|  |  | 20140214 | 20140716 | 20140522 | 20140523 |
|  |  | | Type of sample | | |
|  |  | Water | Water | Water | Water |
|  |  | | Date prepared | | |
|  |  | 15 Mar. 2014 | 22 Jul. 2014 | 29 May 2014 | 26 May 2014 |
|  |  | | Date analysed | | |
| Miscellaneous Inorganics |  | 15 Mar. 2014 | 22 Jul. 2014 | 29 May 2014 | 26 May 2014 |
| pH | pH Units | 7 | 7.8 | 9.7 | 6.3 |
| BOD |  | 15,00 | 630 | 26,000 | 9,800 |
| Total Dissolved Solids (by calc) m | mg/L | 600 | 7,200 | 6,900 | 11,000 |
| COO | mg O2/L | 19,000 | 18,000 | 50,000 | 24,000 |
| Total Organic Carbon | mg/L | 5,900 | 6,500 | 17,000 | 6,600 |

TABLE 35-continued

Water Analysis (Radiata Pine Wood Flour w/-Black Liquor 20140523)
Water sample Cat. 1-ITR Trials, data from separate Erly.lrolab Services. reports

| | | Our Reference: | | | |
|---|---|---|---|---|---|
| | | 114714-1 | 113424-1 | 110678-1 | 110463-1 |
| | | | Your Reference | | |
| | | 20140814 | 20140716 | 20140528 | 20140523 |
| | | | Type of sample | | |
| | | 18 Aug. 2014 | Water | Water | Water |
| | | | Date digested | | |
| | | 18 Aug. 2014 | 23 Jul. 2014 | 30 May 2014 | 27 May 2014 |
| | | | Date analysed | | |
| Cations in water-Total | | 18 Aug. 2015 | 23 Jul. 2014 | 30 May 2014 | 27 May 2014 |
| Sodium-Total | mg/L | 2,300 | 5,200 | 5,500 | 2,100 |
| Potassium-Total | mg/L | 190 | 54 | 16 | 150 |
| Calcium-Total | mg/L | 16 | <0.5 | 680 | 3,8 |
| Magnesium-Total | mg/L | 3.4 | 1.6 | 270 | 2.5 |

TABLE 36

Water Analysis (Radiate Pine Wood Flour w/- Black Liquor 20140523)
Water sample Cat.1-ITR Trials, data from separate Erly.lrolab Services. reports

| | | Mixed Feedstocks 20140814 | Hog Fuel Sodium Hydroxide 20140716 | Pyrolysed Paper Sludge Black Liquor 20140528 | Radiata Black Liquor 20140523 |
|---|---|---|---|---|---|
| VOCs in water | | | | | |
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| date extracted | | 19 Aug. 2014 | 23 Jul. 2014 | 29 May 2014 | 28 May 2014 |
| date analysed | Units | 22 Aug. 2014 | 23 Jul. 2014 | 30 May 2014 | 29 May 2014 |
| Dichlorodifluoromethane | µg/L | <1,000 | <1,000 | <5,000 | <1,000 |
| Chloromethane | µg/L | <1,000 | <1,000 | <5,000 | <1,000 |
| Vinyl Chloride | µg/L | <1,000 | <1,000 | <5,000 | <1,000 |
| Bromomethane | µg/L | <1,000 | <1,000 | <5,000 | <1,000 |
| Chloroethane | µg/L | <1,000 | <1,000 | <5,000 | <1,000 |
| Trichlorofluoromethane | µg/L | <1000 | <1,000 | <5,000 | <1,000 |
| 1,1- Dichloroethane | µg/L | <100 | <100 | <500 | <100 |
| Trans-1,2-dichloroethene | µg/L | <100 | <100 | <500 | <100 |
| 1,1- dichloroethane | µg/L | <100 | <100 | <500 | <100 |
| Cis-1,2-dichloroethene | µg/L | <100 | <100 | <500 | <100 |
| Bromochloromethane | µg/L | <100 | <100 | <500 | <100 |
| Chloroform | µg/L | <100 | <100 | <500 | <100 |
| 2,2-dichloropropane | µg/L | <100 | <100 | <500 | <100 |
| 1,2-dichioroethane | µg/L | <100 | <100 | <500 | <100 |
| 1,1,1-trichloroethane | µg/L | <100 | <100 | <500 | <100 |
| 1,1-dichloropropene | µg/L | <100 | <100 | <500 | <100 |
| Cyclohexane | µg/L | <100 | <100 | <500 | <100 |
| Carbon tetrachloride | µg/L | <100 | <100 | <500 | <100 |
| Benzene | µg/L | <180 | 340 | <500 | 340 |
| Dibromomethane | µg/L | <100 | <100 | <500 | <100 |
| 1,2-dichloropropane | µg/L | <100 | <100 | <500 | <100 |
| Trichloroethene | µg/L | <100 | <100 | <500 | <100 |
| Bromodichloromethane | µg/L | <100 | <100 | <500 | <100 |
| Trans-1,3-dichloropropene | µg/L | <100 | <100 | <500 | <100 |
| cis-1,3-dichloropropene | µg/L | <100 | <100 | <500 | <100 |
| 1,1,2-trichloroethane | µg/L | <100 | <100 | <500 | <100 |
| Toluene | µg/L | 370 | 890 | 810 | 680 |
| 1,3-dichloropropane | µg/L | <100 | <100 | <500 | <100 |
| Dibromochloromethane | µg/L | <100 | <100 | <500 | <100 |
| 1,2-dibromoethane | µg/L | <100 | <100 | <500 | <100 |
| Tetrachloroethene | µg/L | <100 | <100 | <500 | <100 |
| 1,1,1,2-tetrachloroethane | µg/L | <100 | <100 | <500 | <100 |
| Chlorobenzene | µg/L | <100 | <100 | <500 | <100 |
| Ethylbenzene | µg/L | <100 | <120 | <500 | <130 |

TABLE 36-continued

Water Analysis (Radiate Pine Wood Flour w/- Black Liquor 20140523)
Water sample Cat.1-ITR Trials, data from separate Erly.Irolab Services. reports

|  |  | Mixed Feedstocks 20140814 | Hog Fuel Sodium Hydroxide 20140716 | Pyrolysed Paper Sludge Black Liquor 20140528 | Radiata Black Liquor 20140523 |
|---|---|---|---|---|---|
| Bromoform | μg/L | <100 | <100 | <500 | <100 |
| m + p-xylene | μg/L | 200 | <200 | <1000 | <200 |
| Styrene | μg/L | <100 | <100 | <500 | <100 |
| 1,1,2,2-tetracholorethane | μg/L | <100 | <100 | <500 | <100 |
| o-xylene | μg/L | <100 | <120 | <500 | <100 |
| 1,2,3-trichloropropane | μg/L | <100 | <100 | <500 | <100 |
| Isopropybenzene | μg/L | <100 | <100 | <500 | <100 |

VOCs in water

|  |  |  |  |  |  |
|---|---|---|---|---|---|
| Our Reference: |  | 114714-1 | 113424-1 | 110678-1 | 110463-1 |
| Your Reference |  | 20148014 | 20140716 | 20140528 | 20140523 |
| Type of sample |  | Water | Water | Water | Water |
| Bromobenzene | μg/L | <100 | <100 | <500 | <100 |
| n-propyl benzene | μg/L | <100 | <100 | <500 | <100 |
| 2-chiorotoluene | μg/L | <100 | <100 | <500 | <100 |
| 4-chbrotoluene | μg/L | <100 | <100 | <500 | <100 |
| 1,3,5-trimethyl benzene | μg/L | <100 | <100 | <500 | <100 |
| Tert-butyl benzene | μg/L | <100 | <100 | <500 | <100 |
| 1,2,4-trimethyl benzene | μg/L | <100 | <100 | <500 | <100 |
| 1,3-dichlorobenzene | μg/L | <100 | <100 | <500 | <100 |
| Sec-butyl benzene | μg/L | <100 | <100 | <500 | <100 |
| 1,4-dichlorobenzene | μg/L | <100 | <100 | <500 | <100 |
| 4-isopropyl toluene | μg/L | <100 | <100 | <500 | <100 |
| 1,2-dichlorobenzene | μg/L | <100 | <100 | <500 | <100 |
| n-butyl benzene | μg/L | <100 | <100 | <500 | <100 |
| 1,2-dibromo-3-chloropropane | μg/L | <100 | <100 | <500 | <100 |
| 1,2,4-trichlorobenzene | μg/L | <100 | <100 | <500 | <100 |
| Hexachlorobutadiene | μg/L | <100 | <100 | <500 | <100 |
| 1,2,3-trichlorobenzene | μg/L | <100 | <100 | <500 | <100 |
| Surrogate Dibromofluoromethane | μg/L | 100% | 106% | 112% | 105% |
| Surrogate toluene-d8 | μg/L | 101% | 105% | 100% | 100% |
| Surrogate 4-BFB | μg/L | 106% | 95% | 100% | 99% |

|  |  | Mixed Feedstocks 20140814 | Hog Sod Fuel um Hydroxide 20140716 | Pyrolysed Paper Sludge Black Liquor 20140528 | Radiata Black Liquor 20140523 |
|---|---|---|---|---|---| vTRH(C6-C10)/BTEXN in Water

|  | Units |  |  |  |  |
|---|---|---|---|---|---|
| Our Reference: |  | 114714-1 | 113424-1 | 110678-1 | 110463-1 |
| Your Reference |  | 2014 Aug. 14 | 2014 Jul. 16 | 2014 May 28 | 2014 May 23 |
| Type of sample |  | Water | Water | Water | Water |
| Date extracted |  | 19 Aug. 2014 | 23 Jul. 2014 | 29 May 2014 | 28 May 2014 |
| Date analysed |  | 22 Aug. 2014 | 23 Jul. 2014 | 30 May 2014 | 29 May 2014 |
| TRH C6-C9 | μg/L | 31,000 | 42,000 | 26,000 | 33,000 |
| TRH C6-C10 | μg/L | 34,000 | 50,000 | 27,000 | 36,000 |
| TRH C6-C10 less BTEX (F1) | μg/L | 33,000 | 49,000 | 26,000 | 35,000 |
| Benzene | μg/L | 180 | 430 | <500 | 340 |
| Toluene | μg/L | 370 | 890 | 810 | 680 |
| Ethylbenzene | μg/L | <100 | 120 | <500 | 130 |
| m + p-xylene | μg/L | <200 | <200 | <1000 | <200 |
| o-xylene | μg/L | <100 | 120 | <500 | <100 |
| Naphthalene | μg/L | <100 | <100 | <501 | <100 |
| Surrogate Dibromofluoromethane | μg/L | 100% | 106% | 112% | 105% |
| Surrogate toluene-d8 | μg/L | 101% | 105% | 100% | 100% |
| Surrogate 4-BFB | μg/L | 106% | 95% | 100% | 99% | svTRH (C10-C40) in Water

|  |  |  |  | Water |  |
|---|---|---|---|---|---|
| Our Reference: |  | 114714-1 | 113424-1 | 110678-1 | 110463-1 |
| Your Reference |  | 20140814 | 20140716 | 20140528 | 20140523 |
| Type of sample |  | Water | Water | Water | Water |
| Date extracted |  | 18 Aug. 2014 | 24 Jul. 2014 | 30 May 2014 | 28 May 2014 |
| Date analysed |  | 19 Aug. 2014 | 24 Jul. 2014 | 31 May 2014 | 29 May 2014 |
| TRH C10-C14 | μg/L | 650,000 | 430,000 | 25,000 | 860,000 |
| TRH C15-C26 | μg/L | 490.000 | 190,000 | 160,000 | 510,000 |

TABLE 36-continued

Water Analysis (Radiate Pine Wood Flour w/- Black Liquor 20140523)
Water sample Cat.1-ITR Trials, data from separate Erly.Irolab Services. reports

|  |  | Mixed Feedstocks 20140814 | Hog Fuel Sodium Hydroxide 20140716 | Pyrolysed Paper Sludge Black Liquor 20140528 | Radiata Black Liquor 20140523 |
|---|---|---|---|---|---|
| TRH C29-C36 | μg/L | 14,000 | 6,600 | 16,000 | 18,000 |
| TRH >010-C16 | μg/L | 800,000 | 450,000 | 260,000 | 860,000 |
| TRH >010-C16 less Naphthalene (F2) |  | 800,000 | 450,000 | 260,000 | 860,000 |
| TRH >C16-C34 | μg/L | 180,000 | 91,000 | 120,000 | 260,000 |
| TRH >C34-C40 | μg/L | 1,800 | <1,000 | 4,800 | 5,300 |
| Surrogate o-Terphenyl | % | # | # | # | # |
| HM in water-total |  |  |  |  |  |
|  |  |  |  |  |  |
| Our Reference: |  | 114714-1 | 113424-1 | 110678-1 | 110463-1 |
| Your Reference |  | 20140814 | 20140716 | 20140528 | 20140523 |
| Type of sample |  | Water | Water | Water | Water |
| Date prepared |  | 18 Aug. 2014 | 23 Jul. 2014 | 30 May 2014 | 27 May 2014 |
| Date analysed |  | 18 Aug. 2014 | 23 Jul. 2014 | 30 May 2014 | 27 May 2014 |
| Arsenic-Total | μg/L | 45 | 2 | 29 | 27 |
| Cadmium-Total | μg/L | 0.1 | <01 | 57 | <0.1 |
| Chromium-Total | μg/L | 1 | 1 | 110 | <1 |
| Copper-Total | μg/L | 1 | <1 | 180 | 1 |
| Lead-Total | μg/L | 1 | <1 | 40 | <1 |
| Mercury-Total | μg/L | 0.3 | 0.06 | 1 | 0.58 |
| Nickel-Total | μg/L | 1 | <1 | 97 | <1 |
| Zinc-Total | μg/L | 44 | 8 | 1,100 | 14 |
| Metals in Waters - Acid extractable |  |  |  |  |  |
|  |  |  |  |  |  |
| Our Reference: |  | 114714-1 | 113424-1 | 110678-1 | 110463-1 |
| Your Reference |  | 20140814 | 20140716 | 20140528 | 20140523 |
| Type of sample |  | Water | Water | Water | Water |
| Date prepared |  | 18 Aug. 2014 | 23 Jul. 2014 | 30 May 2014 | 27 May 2014 |
| Date analysed |  | 18 Aug. 2014 | 23 Jul. 2014 | 30 May 2014 | 27 May 2014 |
| Sulfur -Total | mg/L | 840 | 6.3 | 26 | 150 |
| Miscellaneous Inorganics |  |  |  |  |  |
|  |  |  |  |  |  |
| Our Reference: |  | 144714-1 | 113424-1 | 110678-1 | 110463-1 |
| Your Reference |  | 20140814 | 20140716 | 20140528 | 20140523 |
| Type of sample |  | Water | Water | Water | Water |
| Date prepared |  | 15 Aug. 2014 | 22 Jul. 2014 | 29 May 2014 | 26 May 2014 |
| Date analysed |  | 15 Aug. 2014 | 22 Jul. 2014 | 29 May 2014 | 26 May 2014 |
| pH | pH Units | 7 | 7.8 | 9.7 | 6.3 |
| BOD |  | 15,00 | 630 | 26,000 | 9,800 |
| Total Dissolved Solids (by calc) mg | mg/L | 600 | 7,200 | 6,900 | 11,000 |
| COD | mg O2/L | 19,000 | 18,000 | 50,000 | 24,000 |
| Total Organic Carbon | mg/L | 5,900 | 6,500 | 17,000 | 6,600 |
| Cations in water -Total |  |  |  |  |  |
|  |  |  |  |  |  |
| Our Reference: |  | 114714-1 | 113424-1 | 110678-1 | 110463-1 |
| Your Reference |  | 20140814 | 20140716 | 20140528 | 20140523 |
| Type of sample |  | Aug. 18, 2014 | Water | Water | Water |
| Date digested |  | 18 Aug. 2014 | 23 Jul. 2014 | 30 May 2014 | 27 May 2014 |
| Date analysed |  | 18 Aug. 2014 | 23 Jul. 2014 | 30 May 2014 | 27 May 2014 |
| Sodium-Total | mg/L | 2,300 | 5,200 | 5,500 | 2,100 |
| Potassium-Total | mg/L | 190 | 54 | 16 | 150 |
| Calcium-Total | mg/L | 16 | <0.5 | 680 | 3,8 |
| Magnesium-Total | mg/L | 3.4 | 1.6 | 270 | 2.5 |

TABLE 37

Feedstock Comparison

| | | Proximate Analysis | | | | Ultimate Analysis | | | | | | |
|---|---|---|---|---|---|---|---|---|---|---|---|---|
| Run # | Description | Moisture (% wt ar) | Ash (% wt db) | Volatiles (% wt db) | Fixed C. (% wt db) | GCV (MJ/kg db) | Carbon (% wt db) | Hydrogen (% wt db) | Nitrogen (% wt db) | Sulphur (% wt db) | Oxygen (% wt db) | Chlorine (%) | Molar H/C Ratio |
|  | radiata pine 150 um | 9 | 0.50 | 79.30 | 20.20 | 21.30 | 52.50 | 6.10 | <0.01 | 0.02 | 40.88 | n/a | 1.38 |
| 1 | SPF wood | 43.8 | 0.6 | 79.5 | 19.9 | 18.6 | 52.1 | 6.3 | 0.21 |  | 40.8 |  | 1.45 |
|  | Hog Fuel | 60.0 | 2.2 | 74.4 | 23.5 | 22.8 | 52.9 | 6.0 | 0.25 |  | 38.7 |  | 1.36 |
| 2, 3 | Black liquor | 53.9 | 47.07 |  |  |  | 37.53 | 1.67 | <0.01 | 4.77 | 3.23 | 0.21 | 0.53 |

TABLE 37-continued

Feedstock Comparison

| | | Proximate Analysis | | | | Ultimate Analysis | | | | | | |
|---|---|---|---|---|---|---|---|---|---|---|---|---|
| Run # | Description | Moisture (% wt ar) | Ash (% wt db) | Volatiles (% wt db) | Fixed C. (% wt db) | GCV (MJ/kg db) | Carbon (% wt db) | Hydrogen (% wt db) | Nitrogen (% wt db) | Sulphur (% wt db) | Oxygen (% wt db) | Chlorine (%) | Molar H/C Ratio |
| | Sludge, as received | 6.4 | 9.7 | 80.4 | 10.0 | 13.82 | 42.8 | 5.7 | 0.23 | | 41.57 | | 1.60 |

TABLE 38

Additional information on Radiata pine wood
Biochemical Composition

| Cellulose (% wt db) | Hemicell. (% wt db) | Lignin (% wt db) | Extractives (% wt db) |
|---|---|---|---|
| 47.03 | 10.39 | 35.96 | 6.47 |

TABLE 39

Feedstock Comparison

Ash Constituents

| Run # | Description | SiO2 (% wt db) | Al2O3 (% wt db) | Fe2O3 (% wt db) | TiO2 (% wt db) | K2O (% wt db) | MgO (% wt db) | Na2O (% wt db) | CaO (% wt db) |
|---|---|---|---|---|---|---|---|---|---|
| | radiata pine 150 um | 16.10 | 3.10 | 1.60 | 0.14 | 13.30 | 9.80 | 1.60 | 25.70 |
| 1 | SPF wood | 2.3 | 1.1 | 0.69 | 0.04 | 16.3 | 7.9 | 0.42 | 33.9 |
| | Hog Fuel | 1.1 | 0.62 | 0.28 | 0.02 | 7.6 | 3.2 | 0.30 | 46.7 |
| | Sludge, as received | 9.8 | 1.1 | 1.2 | 0.08 | 0.30 | 11.8 | 2.8 | 40.4 |
| 4 | Pyrolysed sludge | | | | | | | | |

Ash Constituents

| Run # | Description | SO3 (% wt db) | P2O5 (% wt db) | Mn3O4 (% wt db) | SrO (% wt db) | BaO (% wt db) | ZnO (% wt db) | V2O5 (% wt db) |
|---|---|---|---|---|---|---|---|---|
| | radiata pine 150 um | 13.10 | 6.60 | 1.40 | 0.11 | 0.07 | 0.20 | <0.01 |
| 1 | SPF wood | 1.2 | 2.2 | 2.3 | 0.12 | 0.30 | 0.28 | 0.00 |
| | Hog Fuel | 1.0 | 2.5 | 1.5 | 0.24 | 0.60 | 0.42 | 0.00 |
| | Sludge, as received | 2.4 | 0.41 | 0.38 | 0.05 | 0.06 | 0.05 | 0.00 |
| 4 | Pyrolysed sludge | | | | | | | | mg/kg as received basis

| Run # | Description | Na | K | Fe | Ca | Mg | V | Si | P | S |
|---|---|---|---|---|---|---|---|---|---|---|
| 3 | Black Liquor | 61900 | 5310 | 8 | 35 | 35 | <1 | 100 | 15 | 22400 | mg/kg as received basis

| Run # | Description | Ni | Mn | Cr | Cu | Se | Zn | Ba | As | Al |
|---|---|---|---|---|---|---|---|---|---|---|
| 3 | Black Liquor | <1 | 26 | 1 | <1 | <1 | 2 | 1 | <1 | 8 |

TABLE 40

Biocrude Comparison

| | Wt %, dry basis | | | | | GCV dry basis | Wt %, dry ash free basis | | | | | GCV daf basis |
|---|---|---|---|---|---|---|---|---|---|---|---|---|
| Description | Ash | C | H | N | S | O | MJ/kg | C | H | N | S | O | MJ/kg |
| Hog fuel + catalyst | 6.2 | 76.7 | 7.2 | 0.3 | 0.1 | 9.5 | 33.9 | 81.8 | 7.7 | 0.3 | 0.1 | 10.2 | 36.1 |
| Hog fuel + Black liquor | 2.8 | 70.6 | 7.3 | 0.3 | 0.7 | 18.3 | 32.6 | 72.6 | 7.5 | 0.3 | 0.7 | 18.9 | 33.5 |
| Mixed feed + Black liquor 1 | 2.4 | 73.3 | 7.2 | 0.4 | 0.7 | 16.1 | 33.0 | 75.1 | 7.4 | 0.4 | 0.7 | 16.5 | 33.8 |

TABLE 40-continued

Biocrude Comparison

| Description | Wt %, dry basis | | | | | GCV dry basis | Wt %, dry ash free basis | | | | | GCV daf basis |
|---|---|---|---|---|---|---|---|---|---|---|---|---|
| | Ash | C | H | N | S | O | MJ/kg | C | H | N | S | O | MJ/kg |
| Mixed feed + Black liquor 2 | 2.0 | 74.5 | 7.3 | 0.3 | 0.7 | 15.3 | 33.0 | 76.0 | 7.4 | 0.3 | 0.7 | 15.6 | 33.7 |
| Radiata pine biocrude - typical | 0.8 | 78.3 | 7.0 | 0.1 | 0.02 | 13.8 | 34.0 | 78.9 | 7.1 | 0.1 | 0.02 | 13.9 | 34.3 |
| Radiata Pine + Black liquor biocrude | 0.4 | 79.0 | 7.3 | 0.2 | 0.7 | 13.0 | 34.3 | 79.3 | 7.3 | 0.2 | 0.7 | 12.5 | 34.4 |

TABLE 41

Biocrude Comparison-Ash

| Run # | Sample Description | % oxide in ash | | | | | | | | | |
|---|---|---|---|---|---|---|---|---|---|---|---|
| | | SiO2 | Al2O3 | Fe2O3 | TiO2 | K2O | MgO | Na2O | CaO | SO3 | P2O5 |
| 1 | SPF wood biocrude | — | — | — | — | — | — | — | — | — | — |
| 2 | Black liquor biocrude #1 | 3.6 | 4.4 | 5.6 | 0.08 | 1.4 | 17 | 13.1 | 3.2 | 19.1 | 0.60 |
| 3 | Black liquor biocrude #2 | 5.4 | 3.9 | 2.5 | 0.07 | 3.7 | 2.0 | 27.9 | 3.1 | 38.0 | 0.51 |
| 4 | Paper sludge oily product | 10.4 | 082 | 1.8 | 0.14 | 0.06 | 8.6 | 30 | 73.5 | 0.48 | 0.34 |
| 5 | Hog fuel + catalyst | 0.8 | 1.7 | 1.4 | 0.05 | 0.34 | 3.7 | 7.2 | 46.6 | 1.1 | 2.459 |
| 6 | Hog fuel + Black liquor | 3 | 3.7 | 9.9 | 0.13 | 0.44 | 3.7 | 3.6 | 36.2 | 24.3 | 3.55 |
| 7 | Mixed feed + Black liquor 1 | | | | | | | | | | |
| 8 | Mixed feed + Black liquor 2 | | | | | | | | | | |
| | Radiata pine biocrude | 36.10 | 13.10 | 11.60 | 0.80 | 1.30 | 3.60 | 7.90 | 11.70 | 1.60 | 1.70 |

| Run # | Sample Description | % oxide in ash | | | | | | | | |
|---|---|---|---|---|---|---|---|---|---|---|
| | | BaO | SrO | CuO | MnO | Cr2O3 | ZnO | V2O5 | Co3O4 | NiO |
| 1 | SPF wood biocrude | — | — | — | — | — | — | — | — | — |
| 2 | Black liquor biocrude #1 | 0.04 | <0.01 | 0.36 | 0.24 | 0.16 | 0.20 | 0.52 | 0.00 | 0.04 |
| 3 | Black liquor biocrude #2 | 0.04 | 0.00 | 0.32 | 0.32 | 0.07 | 0.16 | 0.09 | 0.00 | 0.05 |
| 4 | Paper sludge oily product | 0.07 | 0.07 | 0.03 | 0.38 | 0.03 | 0.04 | <0.01 | <0.01 | 0.01 |
| 5 | Hog fuel + catayst | 1.17 | 0.17 | 0.4 | 0.31 | 0.11 | 0.02 | 0 | 0.02 | 0 |
| 6 | Hog fuel + Black liquor | 1.39 | 0.17 | 0.5 | 0.56 | 0.17 | 0.02 | 0 | 0.02 | 0 |
| 7 | Mixed feed + Black liquor 1 | | | | | | | | | |
| 8 | Mixed feed + Black liquor 2 | | | | | | | | | |
| | Radiata pine biocrude | 0.21 | 0.05 | | 0.42 | | 0.18 | 0.07 | | |

TABLE 42

Analysis of WEAK BLACK LIQUOR

| | Mill A | Mill B | Mill C | Mill D |
|---|---|---|---|---|
| Total Solids, % | 15.4 | 147 | 14.4 | 15.5 |
| Density, g/ml | 1.08 | 1.09 | 1.08 | NM |
| Hydroxide (OH) | 1090(7080) | 2510(17100) | 2240(15600) | 470(3020) |
| Carbonate (CO) | 5930(38500) | 7910(53800) | 6450(44800) | 8750(56500) |
| Sulphate (SO$_4$) | 4720(30600) | 3290(22400) | 3730(25900) | 5020(32400) |
| Total Sulphur (S) | 7500(48700) | 6220(42300) | 7070(49100) | 6830(44100) |
| Chloride (Cl) | 1270(8230) | 8340(56800) | 700(4850) | 3590(23200) |
| Aluminum (Al) | 5.5(36) | 5.0(34) | 1.9(13) | 11(70) |
| Calcium (Ca) | 30(200) | 49(330) | 72(500) | 58(370) |
| Chromium (Cr) | 0.5(3.0) | 0.2(1.5) | ND | 0.2(1.5) |
| Iron (Fe) | 16(100) | 9.3(63) | 3.5(24) | 7.3(47) |
| Lead (Pb) | 0.04(0.3) | 0.4(2.5) | 1.4(9.7) | 3.6(23) |
| Magnesium (Mg) | 11(69) | 19(130) | 33(230) | 24(160) |
| Manganese (Mn) | 7.7(50) | 12(79) | 0.8(5.6) | 6.4(41) |
| Phosphorous (PO$_4^-$) | NM | 11(73) | 8.7(60) | 13(85) |
| Potassium (K) | 1630(10600) | 2430(16500) | 5520(38300) | 1990(12800) |
| Total Silica (Si) | 37(240) | 30(200) | 88(610) | 94(610) |
| Sodium (Na) | 24600(160000) | 34100(232000) | 26800(186000) | 30500(197000) |
| Zinc (Zn) | 16(100) | 1.2(8.2) | 3.2(22) | 1.0(6.3) |

( ) = concentration mg/kg of dry solids

TABLE 43

Analysis of HEAVY BLACK LIQUOR

| | Mill A | Mill B | Mill C | Mill D |
|---|---|---|---|---|
| Total Solids, % | 15.4 | 66.1 | 70.2 | 70 |
| Density, g/m at 20 C | 1.38 | 1.4 | 1.076 | NM |
| Hydroxide (OH) | 3210(5270) | 5750(8690) | 14900(21200) | 5980(8540) |
| Carbonate ($CO_3$) | 25500(41800) | 35100(53100) | 30900(44000) | 38800(55400) |
| Sulphate ($SO_4$) | 32300(53100) | 26700(40300) | 19700(28000) | 41400(59100) |
| Total Sulphur (S) | 32700(53800) | 32800(49600) | 34900(49700) | 34000(48500) |
| Chloride (Cl) | 6160(10100) | 20800(31500) | 3540(5040) | 20400(29200) |
| Aluminum (Al) | 20(32) | 80(1 | 14(20) | 56(79) |
| Calcium (Ca) | 110(180) | 120(190) | 340(480) | 260(370) |
| Chromium (Cr) | 1.9(3.2) | 1.0(1.5) | ND | 1.1(1 |
| Iron (Fe) | 65(110) | 48(7 | 20(28) | 36(51) |
| Lead (Pb) | 0.1(0.2) | 1.7(2 | 6.8(9. | 16(23) |
| Magnesium (Mg) | 44(72) | 110(160) | 170(250) | 96(140) |
| Manganese (Mn) | 33(54) | 46(6 | 44(6.3) | 30(43) |
| Phosphorous ($PO_4$—P) | NM | 29(4 | 59(84) | 39(5 |
| Potassium (K) | 7520(12300) | 12300(18500) | 23500(33500) | 9950(14200) |
| Total Silica (Si) | 150(250) | 110(170) | 690(9 | 430(620) |
| Sodium (Na) | 107000(176000) | 156000(236000) | 131000(186000) | 128000(183000) |
| Zinc (Zn) | 62(100) | 7.2(11) | 16(23) | 7.2(10) |

( ) = concentration mg/kg of dry solids

TABLE 44

Analysis of RAW UNCLARIFIED GREEN LIQUOR

| | Mill A | Mill B | Mill C | Mill D |
|---|---|---|---|---|
| Density, g/ml | 1.17 | 1.25 | 1.17 | NM |
| Suspended Solids, ppm | NM | NM | 830 | 1080 |
| Sulfite ($SO_3$) | NM | NM | 12500 | NM |
| Thiosulphate ($S_2O_3$) | 2300 | 2810 | 3430 | NM |
| Sulphate ($SO_4$) | 4950 | 11800 | 8300 | 5390 |
| Total Sulphur (S) | 19200 | 18200 | 18600 | 15700 |
| Chloride (Cl) | 3150 | 21100 | 1850 | 8290 |
| Aluminum (Al) | 7.3 | 22 | 3.8 | 28 |
| Calcium (Ca) | 68 | 100 | 140 | 100 |
| Chromium (Cr) | 0.9 | 0.8 | 0.9 | 0.5 |
| Iron (Fe) | 22 | 58 | 11 | 43 |
| Lead (Pb) | 0.4 | 0.2 | 2.1 | 5.9 |
| Magnesium (Mg) | 12 | 69 | 130 | 42 |
| Manganese (Mn) | 8.2 | 28 | 2.1 | 13 |
| Phosphorous ($PO_4$—P) | NM | 19 | 7.4 | 0.3 |
| Potassium (K) | 4390 | 6930 | 14300 | 4000 |
| Total Silica (Si) | 77 | 63 | 180 | 210 |
| Sodium (Na) | 63500 | 94700 | 68300 | 78100 |
| Zinc (Zn) | 24 | 2.1 | 7 | 1.7 |

TABLE 45

Analysis of CLARIFIED GREEN LIQUOR

| | Mill A | Mill B | Mill C | Mill D |
|---|---|---|---|---|
| Active Alkali, g/L as $Na_2O$ | 45 | 46 | 39 | 41 |
| Effective Alkali, g/L as $Na_2O$ | 26 | 270 | 24 | 27 |
| Total Titratable Alkali, g/L as $Na_2O$ | 111 | 120 | 111 | 111 |
| Density, g/ml | 1.17 | 1.25 | 1.17 | NM |
| Suspended Solids, ppm | 19 | NM | 110 | 320 |
| Sulfite ($SO_3$) | NM | NM | 440 | NM |
| Thiosulphate ($S_2O_3$) | NM | NM | 3320 | NM |
| Sulphate ($SO_4$) | 6040 | 8990 | 4180 | 5330 |
| Total Sulphur (S) | 19200 | 18200 | 15300 | 16000 |
| Chloride (Cl) | 3380 | 21000 | 1820 | 8530 |
| Aluminum (Al) | 7.7 | 8.4 | 1.3 | 18 |
| Calcium (Ca) | 23 | 6.7 | 7.2 | 28 |
| Chromium (Cr) | 0.6 | 0.1 | 0.6 | 0.4 |
| Iron (Fe) | 11 | 6.5 | 4.9 | 7 |
| Lead (Pb) | 0.2 | 0.1 | 1.6 | 6.2 |
| Magnesium (Mg) | 2.5 | 4 | 7.7 | 16 |
| Manganese (Mn) | 2.8 | 2.4 | 0.3 | 5.5 |
| Phosphorous ($PO_4$—P) | NM | 19 | 5.6 | 0.3 |
| Potassium (K) | 4640 | 6900 | 12400 | 4260 |
| Total Silica (Si) | 64 | 63 | 100 | 230 |
| Sodium (Na) | 76800 | 90400 | 61000 | 31400 |
| Zinc (Zn) | 1.4 | 1.2 | 2.6 | 1 |

TABLE 46

Analysis of WHITE LIQUOR

| | Mill A | Mill B | Mill C | Mill D |
|---|---|---|---|---|
| Active Alkali, g/L as $Na_2O$ | 93 | 83 | 102 | 95 |
| Effective Alkali, g/L as $Na_2O$ | 75 | 70 | 87 | 81 |
| Total Titratable Alkali, g/L as $Na_2O$ | 107 | 98 | 116 | 116 |
| Density, g/ml | 1.15 | 1.23 | 1.16 | NM |
| Suspended Solids, ppm | 500 | NM | 23 | NM |
| Sulfite ($SO_3$) | 370 | 130 | 320 | 230 |
| Thiosulphate ($S_2O_3$) | 4170 | 5230 | 3890 | 3620 |
| Sulphate ($SO_4$) | 6240 | 7680 | 5440 | 6600 |
| Total Sulphur (S) | 20100 | 19100 | 16000 | 16600 |
| Chloride (Cl) | 4090 | 22100 | 1910 | 8860 |
| Aluminum (Al) | 12 | 10 | 4.3 | 15 |
| Calcium (Ca) | 13 | 10 | 3.2 | 5.5 |
| Chromium (Cr) | 0.4 | 0.4 | 0.7 | 0.3 |
| Iron (Fe) | 13 | 16 | 7.3 | 5.8 |
| Lead (Pb) | 0.1 | 0.6 | 1.8 | 4.5 |
| Magnesium (Mg) | 1.1 | 2.8 | 0.8 | 0.4 |
| Manganese (Mn) | 2.7 | 5.4 | 0.3 | 4.5 |
| Phosphorous ($PO_4$_ P) | NM | 9.6 | 11 | 10 |
| Potassium (K) | 4700 | 6430 | 8600 | 4730 |
| Total Silica (Si) | 87 | 100 | 120 | 170 |
| Sodium (Na) | 76200 | 97800 | 58000 | 72500 |
| Zinc (Zn) | 1.4 | 8.2 | 1.4 | 1.2 |

Example 5. Integrated Kraft Pulp Mill and Thermochemical Conversion Plant

A thermochemical conversion subsystem as described herein that consumes 571 tonnes per day (tpd) of dry organic matter feedstock is integrated with a 1,000 tpd kraft pulp mill.

The recovery boiler of a 1,000 tpd kraft pulp mill will burn about 1,750 tpd of black liquor solids, approximately 60% to 66% (i.e. approximately 1050 tpd to 1150 tpd) of which is organic matter. Accordingly, the thermochemical conversion subsystem consuming 571 tpd of organic matter feedstock can reduce the amount of black liquor solids burned in the recovery boiler by as much as 50% to 57%.

In a particular embodiment, 0.30 kg of dry black liquor solids per kg of biomass (171 tpd of dry black liquor solids) is used in the thermochemical conversion subsystem consuming 571 tpd organic matter feedstock. The organic matter feedstock provided to the thermochemical conversion subsystem is provided in a ratio of 78 kg hog fuel:20 kg wood chips:2 k sludge:30 kg dry black liquor solids (approximately 20 kg of which black liquor solids is organic matter). According to such an embodiment, approximately 17% of the organic matter feedstock is provided by black liquor solids, or about 95 to 103 tpd. Thus, such embodiment can reduce the amount of black liquor solids burned in the recovery boiler of the 1,000 tpd Kraft mill by as much as 8.3% to 9.5%.

The 1,000 tpd Kraft mill may also recover about 65 tpd to about 132 tpd of tall oil soap depending on the source of the chip furnish, of which approximately 60% to 65% is dry organic matter (i.e. about 39 tpd to about 86 tpd). Thus, approximately 7% to 15% of the organic matter feedstock could be provided in the form of tall oil soap and thus significantly reduce the cost of processing tall oil soap to tall oil.

A 1,000 tpd Kraft mill also produces as much as 6 to 12 tpd of methanol in the form of condensates, and thus can provide approximately 1 to 2% of the organic matter required for the thermochemical conversion subsystem. The condensate streams also contain a number of other organics (including ethanol, methyl ethyl ketone, TRS, etc.) which could provide an additional 0.5 to 2% of the required organic matter.

The reaction mixture in the thermochemical conversion subsystem may be around 9-20% by weight, and thus the thermochemical conversion system may utilize approximately 6334.4 tpd of water. This represents 6.3 tonnes or m³/tonne of pulp for a 1,000 tpd mill. Part of the process water used in the thermochemical conversion subsystem may be recycled within the subsystem to reduce heating requirements. However, a portion of this process water can be returned to places in the pulp mill that typically utilize condensates, thereby substituting for the condensates that are directed from the pulp mill to the thermochemical conversion subsystem. For example, a typical Kraft mill will use over 30 m³/tonne of water in the bleach plant, 10 m³/tonne in brown stock washing, and 2-4 m³/tonne of fresh water in recausticization.

Operation

While specific embodiments of the invention have been described and illustrated, such embodiments should be considered illustrative of the invention only and not as limiting the invention as construed in accordance with the accompanying claims.

What is claimed is:

1. An integrated Kraft pulp mill and thermochemical conversion system, the system comprising:
   a Kraft pulp mill comprising a digester for digesting a lignocellulosic material with white liquor to produce pulp and black liquors;
   a thermochemical conversion subsystem comprising:
      at least one mixing tank configured to receive: (i) black pulping liquors from the pulp mill; and (ii) organic matter feedstock from another source, independent of the pulp mill; and (iii) water to produce a reaction mixture, wherein the organic matter feedstock is other than a pulping liquor;
      a reactor vessel configured to treat the reaction mixture, which is received from the mixing tank at a reaction temperature and pressure suitable for conversion of all or a portion of said organic matter feedstock which is other than pulping liquor, as well as the black pulping liquors, in the reaction mixture into a product mixture comprising a bioproduct and an aqueous stream containing both organic and inorganic compounds; and
      a depressurizer for depressurizing product mixture received from the reactor vessel; and
   one or more conveyors for conveying the pulping liquors from the pulp mill to the mixing tank.

2. The system of claim 1, wherein the pulp mill further comprises an evaporator for concentrating weak black liquor received from the digester to produce strong black liquor and condensates.

3. The system of claim 2, wherein the condensates are organics-enriched condensates, wherein the organics-enriched condensates include methanol, ethanol, an organic and/or reduced sulphur species, or any combination thereof.

4. The system of claim 3, wherein the organic or reduced sulphur species includes methyl mercaptan, hydrogen sulphide, dimethyl mercaptan, dimethyl disulfide or a combination thereof.

5. The system of claim 2, wherein the one or more conveyors include a weak liquor conveyor for conveying the weak liquor to the mixing tank, a strong black liquor conveyor for conveying strong black liquor from the evaporators to the mixing tank, a heavy black liquor conveyor for conveying heavy black liquor from a concentrator to the mixing tank, or both.

6. The system of claim 2, wherein a portion of the black liquors are entrained in tall oil soap that collects at a surface of the weak black liquor, and wherein the system further comprises a tall oil soap conveyor for conveying tall oil soap skimmed from the surface of the weak black liquor to the mixing tank.

7. The system of any claim 1, further comprising at least one water conveyor for conveying water from at least one source of water in the pulp mill to the mixing tank, wherein the at least one source of water in the pulp mill includes:
   mill water;
   weak filtrate from brownstock washing;
   bleaching effluent;
   clean condensates;
   dirty condensates;
   foul condensates;
   combined condensates;
   stripper condensates;
   digester condensates;
   evaporator condensates;
   or any combination thereof.

8. The system of any claim 1, further comprising at least one steam conveyor for conveying steam from at least one steam source associated with the pulp mill to the reactor vessel.

9. The system of claim 8, wherein steam from the at least one steam source associated with the pulp mill is conveyed to the reactor vessel or a feedstock slurry indirectly via at least one heat exchanger.

10. The system of claim 8, wherein the at least one steam source is
a hog fuel boiler;
a recovery boiler;
a package boiler;
a blow tank;
a turbine;
a condensing turbine;
flash steam from the thermochemical reactor; or
any combination thereof.

11. The system of any claim 1, further comprising a steam conduit for conducting steam from the depressurizer to the pulp mill.

12. The system of any claim 1, further comprising at least one organic matter conveyor for conveying the organic matter from at least one organic matter source in the pulp mill to the mixing tank to form at least a portion of the reaction mixture.

13. The system of claim 12, wherein the at least one organic matter source is
weak black liquor;
strong black liquor;
condensates;
tall oil soap;
crude sulphate turpentine;
knots;
screening rejects;
black liquor fiber rejects;
primary sludge from the wastewater treatment system;
secondary sludge from a wastewater treatment plant;
hog fuel;
wood chips;
sawdust;
ground wood meal;
or any combination thereof.

14. The system of claim 1, further comprising:
(i) one or more detectors for detecting the rate at which the mixing tank receives the black liquors, organic matter, condensates, or any combination thereof from the pulp mill; and
(ii) an adjustor for adjusting the rate at which organic matter is added to the mixing tank and the reactor vessel in response to a change in the detected rate at which the mixing tank receives the black liquors, the organic matter, the condensates, or any combination thereof from the pulp mill.

15. The system of claim 1, further comprising:
(i) at least one aqueous stream conveyor for conveying an aqueous stream from the thermochemical conversion subsystem to the pulp mill; and/or
(ii) at least one ash conveyor for conveying ash from at least one ash source in the pulp mill to the mixing tank, wherein the at least one ash source is hog fuel boiler ash, fly ash, or both; and/or
(iii) a dregs conveyor for conveying dregs from green liquor clarifier to the mixing tank for reduction of solids buildup in the bioproduct reactor vessel; and/or
(iv) a non-condensible gas (NCG) conveyor for conveying NCG from the depressurizer to a recovery boiler, a lime kiln, a hog fuel boiler, an NCG incinerator, or any combination thereof, for recovery or destruction of sulphur in the NCG.

16. The system of claim 1, further comprising:
a chlor-alkali plant for provision of caustic and chlorine for digestion and/or bleaching and hydrogen to a hydrotreater in the thermochemical conversion system;
a sodium chlorate plant for provision of chlorine dioxide to a bleaching plant of the pulp mill and hydrogen to the hydrotreater of the thermochemical conversion system;
a hydrogen peroxide plant for supplying hydrogen to the hydrotreater of the thermochemical conversion system; or
any combination thereof.

17. The system of claim 1, wherein the reaction temperature is between 300° C. and 400° C.

18. The system of claim 1, wherein the reaction pressure between 180 bar and 350 bar.

19. The system of claim 1, wherein the thermochemical conversion subsystem further comprises:
a separator for separating the aqueous stream containing organic and inorganic compounds from the bioproduct; and
a conveyor for conveying the separated aqueous stream to the pulp mill via a device for removal of the organics from the separated aqueous stream.

20. The system of claim 19, wherein the device for removal of the organics from the separated aqueous stream an air or steam stripper, a distillation column, or a combination thereof.

* * * * *